United States Patent
Ochsner et al.

(10) Patent No.: US 10,370,669 B2
(45) Date of Patent: Aug. 6, 2019

(54) NUCLEIC ACID COMPOUNDS FOR BINDING GROWTH DIFFERENTIATION FACTOR 8

(71) Applicant: SOMALOGIC, INC., Boulder, CO (US)

(72) Inventors: Urs Ochsner, Boulder, CO (US); Louis Green, Boulder, CO (US); Nebojsa Janjic, Boulder, CO (US)

(73) Assignee: SomaLogic, Inc., Boulder, CO (US)

( * ) Notice: Subject to any disclaimer, the term of this patent is extended or adjusted under 35 U.S.C. 154(b) by 0 days.

(21) Appl. No.: 15/545,755

(22) PCT Filed: Feb. 5, 2016

(86) PCT No.: PCT/US2016/016712
§ 371 (c)(1),
(2) Date: Jul. 24, 2017

(87) PCT Pub. No.: WO2016/130414
PCT Pub. Date: Aug. 18, 2016

(65) Prior Publication Data
US 2018/0016581 A1 Jan. 18, 2018

Related U.S. Application Data

(60) Provisional application No. 62/113,866, filed on Feb. 9, 2015.

(51) Int. Cl.
*C12N 15/115* (2010.01)
*G01N 33/53* (2006.01)
*G01N 33/74* (2006.01)

(52) U.S. Cl.
CPC ....... *C12N 15/115* (2013.01); *G01N 33/5308* (2013.01); *G01N 33/74* (2013.01); *C12N 2310/16* (2013.01); *C12N 2310/321* (2013.01); *C12N 2310/322* (2013.01); *G01N 2333/475* (2013.01)

(58) Field of Classification Search
CPC .... C07K 14/71; C07K 14/495; A61K 38/179; A61K 38/00
USPC ...... 435/6.1, 6.11, 91.1, 91.31, 455; 514/44; 536/23.1
See application file for complete search history.

(56) References Cited

U.S. PATENT DOCUMENTS

2016/0287667 A1* 10/2016 Wagers .............. A61K 38/1875
2018/0009872 A1* 1/2018 Sherman ................ C07K 14/71

FOREIGN PATENT DOCUMENTS

| WO | 2008030706 A2 | 3/2008 | |
|---|---|---|---|
| WO | 2008119571 A2 | 10/2008 | |
| WO | WO-2008119571 A2 * | 10/2008 | ......... A61K 31/7088 |

OTHER PUBLICATIONS

McPherron et al, Immunol. Endocr. Metab. Agents Med. Chem., vol. 10, No. 4, pp. 217-231. (Year: 2010).*
Loffredo et al, Cell, vol. 153, pp. 828-839. (Year: 2013).*
Yoshida et al., "Quantitative and sensitive protein detection strategies based on aptamers," Proteomics—Clinical Applications, vol. 6, No. 11-12, Dec. 8, 2012, pp. 574-580.
International Search Report and Written Opinion issued in PCT/US2016/016712, dated Apr. 25, 2016, 14 pages.

* cited by examiner

*Primary Examiner* — Jane J Zara
(74) *Attorney, Agent, or Firm* — McNeill Baur PLLC

(57) ABSTRACT

Described herein are aptamers capable of binding to growth differentiation factor 8 (GDF8) protein; compositions comprising a GDF8 binding aptamer; and methods of making and using the same.

23 Claims, 4 Drawing Sheets
Specification includes a Sequence Listing.

FIG. 3

SEQUENCE LISTING

<160> NUMBER OF SEQ ID NOS: 63

<210> SEQ ID NO 1
<211> LENGTH: 31
<212> TYPE: DNA
<213> ORGANISM: Artificial Sequence
<220> FEATURE:
<223> OTHER INFORMATION: Synthetic: aptamer that binds GDF8
<220> FEATURE:
<221> NAME/KEY: misc_feature
<222> LOCATION: (2)..(3)
<223> OTHER INFORMATION: n is a C-5 modified pyrimidine
<220> FEATURE:
<221> NAME/KEY: misc_feature
<222> LOCATION: (5)..(5)
<223> OTHER INFORMATION: may not be present
<220> FEATURE:
<221> NAME/KEY: misc_feature
<222> LOCATION: (7)..(7)
<223> OTHER INFORMATION: n is a or C-5 modified pyrimidine
<220> FEATURE:
<221> NAME/KEY: misc_feature
<222> LOCATION: (8)..(8)
<223> OTHER INFORMATION: may not be present
<220> FEATURE:
<221> NAME/KEY: misc_feature
<222> LOCATION: (10)..(10)
<223> OTHER INFORMATION: n is a C-5 modified pyrimidine
<220> FEATURE:
<221> NAME/KEY: misc_feature
<222> LOCATION: (11)..(11)
<223> OTHER INFORMATION: may not be present
<220> FEATURE:
<221> NAME/KEY: misc_feature
<222> LOCATION: (12)..(12)
<223> OTHER INFORMATION: n is C-5 modified pyrimidine or c
<220> FEATURE:

```
<221> NAME/KEY: misc_feature
<222> LOCATION: (14)..(14)
<223> OTHER INFORMATION: n, if present, is C-5 modified pyrimidine
<220> FEATURE:
<221> NAME/KEY: misc_feature
<222> LOCATION: (15)..(16)
<223> OTHER INFORMATION: n is C-5 modified pyrimidine
<220> FEATURE:
<221> NAME/KEY: misc_feature
<222> LOCATION: (17)..(17)
<223> OTHER INFORMATION: n is C-5 modified pyrimidine or c
<220> FEATURE:
<221> NAME/KEY: misc_feature
<222> LOCATION: (18)..(18)
<223> OTHER INFORMATION: may not be present
<220> FEATURE:
<221> NAME/KEY: misc_feature
<222> LOCATION: (20)..(20)
<223> OTHER INFORMATION: may not be present
<220> FEATURE:
<221> NAME/KEY: misc_feature
<222> LOCATION: (21)..(21)
<223> OTHER INFORMATION: n is C-5 modified pyrimidine or c
<220> FEATURE:
<221> NAME/KEY: misc_feature
<222> LOCATION: (22)..(22)
<223> OTHER INFORMATION: n is g or C-5 modified pyrimidine
<220> FEATURE:
<221> NAME/KEY: misc_feature
<222> LOCATION: (23)..(23)
<223> OTHER INFORMATION: n, if present, is C-5 modified pyrimidine
<220> FEATURE:
<221> NAME/KEY: misc_feature
<222> LOCATION: (26)..(26)
<223> OTHER INFORMATION: n, if present, is C-5 modified pyrimidine or c
<220> FEATURE:
<221> NAME/KEY: misc_feature
<222> LOCATION: (27)..(27)
<223> OTHER INFORMATION: n is C-5 modified pyrimidine
<220> FEATURE:
<221> NAME/KEY: misc_feature
<222> LOCATION: (29)..(29)
<223> OTHER INFORMATION: n is C-5 modified pyrimidine or c
<220> FEATURE:
<221> NAME/KEY: misc_feature
<222> LOCATION: (30)..(30)
<223> OTHER INFORMATION: n is a or C-5 modified pyrimidine
<220> FEATURE:
<221> NAME/KEY: misc_feature
<222> LOCATION: (31)..(31)
<223> OTHER INFORMATION: n is g, a or C-5 modified pyrimidine

<400> SEQUENCE: 1
gnnrcrnggn cncnnnnarc nnnagnncnn n                              31

<210> SEQ ID NO 2
<211> LENGTH: 32
<212> TYPE: DNA
<213> ORGANISM: Artificial Sequence
<220> FEATURE:
<223> OTHER INFORMATION: Synthetic: aptamer that binds GDF8
<220> FEATURE:
<221> NAME/KEY: misc_feature
<222> LOCATION: (1)..(1)
<223> OTHER INFORMATION: n is C-5 modified pyrimidine or c
<220> FEATURE:
<221> NAME/KEY: misc_feature
<222> LOCATION: (3)..(4)
<223> OTHER INFORMATION: n is a C-5 modified pyrimidine
<220> FEATURE:
<221> NAME/KEY: misc_feature
<222> LOCATION: (6)..(6)
<223> OTHER INFORMATION: may not be present
<220> FEATURE:
<221> NAME/KEY: misc_feature
<222> LOCATION: (8)..(8)
<223> OTHER INFORMATION: n is a or C-5 modified pyrimidine
```

```
<220> FEATURE:
<221> NAME/KEY: misc_feature
<222> LOCATION: (9)..(9)
<223> OTHER INFORMATION: may not be present
<220> FEATURE:
<221> NAME/KEY: misc_feature
<222> LOCATION: (11)..(11)
<223> OTHER INFORMATION: n is a C-5 modified pyrimidine
<220> FEATURE:
<221> NAME/KEY: misc_feature
<222> LOCATION: (12)..(12)
<223> OTHER INFORMATION: may not be present
<220> FEATURE:
<221> NAME/KEY: misc_feature
<222> LOCATION: (13)..(13)
<223> OTHER INFORMATION: n is C-5 modified pyrimidine or c
<220> FEATURE:
<221> NAME/KEY: misc_feature
<222> LOCATION: (15)..(15)
<223> OTHER INFORMATION: n, if present, is C-5 modified pyrimidine
<220> FEATURE:
<221> NAME/KEY: misc_feature
<222> LOCATION: (16)..(17)
<223> OTHER INFORMATION: n is C-5 modified pyrimidine
<220> FEATURE:
<221> NAME/KEY: misc_feature
<222> LOCATION: (18)..(18)
<223> OTHER INFORMATION: n is C-5 modified pyrimidine or c
<220> FEATURE:
<221> NAME/KEY: misc_feature
<222> LOCATION: (19)..(19)
<223> OTHER INFORMATION: may not be present
<220> FEATURE:
<221> NAME/KEY: misc_feature
<222> LOCATION: (21)..(21)
<223> OTHER INFORMATION: may not be present
<220> FEATURE:
<221> NAME/KEY: misc_feature
<222> LOCATION: (22)..(22)
<223> OTHER INFORMATION: n is C-5 modified pyrimidine or c
<220> FEATURE:
<221> NAME/KEY: misc_feature
<222> LOCATION: (23)..(23)
<223> OTHER INFORMATION: n is g or C-5 modified pyrimidine
<220> FEATURE:
<221> NAME/KEY: misc_feature
<222> LOCATION: (24)..(24)
<223> OTHER INFORMATION: n, if present, is C-5 modified pyrimidine
<220> FEATURE:
<221> NAME/KEY: misc_feature
<222> LOCATION: (27)..(27)
<223> OTHER INFORMATION: n, if present, is C-5 modified pyrimidine or c
<220> FEATURE:
<221> NAME/KEY: misc_feature
<222> LOCATION: (28)..(28)
<223> OTHER INFORMATION: n is C-5 modified pyrimidine
<220> FEATURE:
<221> NAME/KEY: misc_feature
<222> LOCATION: (30)..(30)
<223> OTHER INFORMATION: n is C-5 modified pyrimidine or c
<220> FEATURE:
<221> NAME/KEY: misc_feature
<222> LOCATION: (31)..(31)
<223> OTHER INFORMATION: n is a or C-5 modified pyrimidine
<220> FEATURE:
<221> NAME/KEY: misc_feature
<222> LOCATION: (32)..(32)
<223> OTHER INFORMATION: n is g, a or C-5 modified pyrimidine

<400> SEQUENCE: 2
ngnnrcrngg ncncnnnnar cnnnagnncn nn                                    32

<210> SEQ ID NO 3
<211> LENGTH: 24
<212> TYPE: DNA
<213> ORGANISM: Artificial Sequence
<220> FEATURE:
```

```
<223> OTHER INFORMATION: Synthetic: aptamer that binds GDF8
<220> FEATURE:
<221> NAME/KEY: misc_feature
<222> LOCATION: (1)..(1)
<223> OTHER INFORMATION: n is a C-5 modified pyrimidine
<220> FEATURE:
<221> NAME/KEY: misc_feature
<222> LOCATION: (3)..(4)
<223> OTHER INFORMATION: n is a C-5 modified pyrimidine
<220> FEATURE:
<221> NAME/KEY: misc_feature
<222> LOCATION: (7)..(7)
<223> OTHER INFORMATION: n is a or a C-5 modified pyrimidine
<220> FEATURE:
<221> NAME/KEY: misc_feature
<222> LOCATION: (9)..(9)
<223> OTHER INFORMATION: n is a C-5 modified pyrimidine
<220> FEATURE:
<221> NAME/KEY: misc_feature
<222> LOCATION: (10)..(10)
<223> OTHER INFORMATION: n is C-5 modified pyrimidine or c
<220> FEATURE:
<221> NAME/KEY: misc_feature
<222> LOCATION: (12)..(13)
<223> OTHER INFORMATION: n is a C-5 modified pyrimidine
<220> FEATURE:
<221> NAME/KEY: misc_feature
<222> LOCATION: (14)..(14)
<223> OTHER INFORMATION: n is a C-5 modified pyrimidine or c
<220> FEATURE:
<221> NAME/KEY: misc_feature
<222> LOCATION: (16)..(16)
<223> OTHER INFORMATION: n is a C-5 modified pyrimidine
<220> FEATURE:
<221> NAME/KEY: misc_feature
<222> LOCATION: (20)..(20)
<223> OTHER INFORMATION: n is a C-5 modified pyrimidine
<220> FEATURE:
<221> NAME/KEY: misc_feature
<222> LOCATION: (22)..(22)
<223> OTHER INFORMATION: n is a C-5 modified pyrimidine
<220> FEATURE:
<221> NAME/KEY: misc_feature
<222> LOCATION: (24)..(24)
<223> OTHER INFORMATION: n is g, a or C-5 modified pyrimidine

<400> SEQUENCE: 3
ngnnagngnn cnnnangagn cnan                                            24

<210> SEQ ID NO 4
<211> LENGTH: 23
<212> TYPE: DNA
<213> ORGANISM: Artificial Sequence
<220> FEATURE:
<223> OTHER INFORMATION: Synthetic: aptamer that binds GDF8
<220> FEATURE:
<221> NAME/KEY: misc_feature
<222> LOCATION: (2)..(3)
<223> OTHER INFORMATION: n is a C-5 modified pyrimidine
<220> FEATURE:
<221> NAME/KEY: misc_feature
<222> LOCATION: (8)..(8)
<223> OTHER INFORMATION: n is a C-5 modified pyrimidine
<220> FEATURE:
<221> NAME/KEY: misc_feature
<222> LOCATION: (11)..(13)
<223> OTHER INFORMATION: n is a C-5 modified pyrimidine
<220> FEATURE:
<221> NAME/KEY: misc_feature
<222> LOCATION: (15)..(15)
<223> OTHER INFORMATION: n is a C-5 modified pyrimidine
<220> FEATURE:
<221> NAME/KEY: misc_feature
<222> LOCATION: (19)..(19)
<223> OTHER INFORMATION: n is a C-5 modified pyrimidine
<220> FEATURE:
<221> NAME/KEY: misc_feature
```

```
<222> LOCATION: (21)..(21)
<223> OTHER INFORMATION: n is a C-5 modified pyrimidine

<400> SEQUENCE: 4
gnnagagncc nnnangagnc nag                                              23

<210> SEQ ID NO 5
<211> LENGTH: 50
<212> TYPE: DNA
<213> ORGANISM: Artificial Sequence
<220> FEATURE:
<223> OTHER INFORMATION: Synthetic: 14583-49_3
<220> FEATURE:
<221> NAME/KEY: misc_feature
<222> LOCATION: (7)..(7)
<223> OTHER INFORMATION: n is TrpdU
<220> FEATURE:
<221> NAME/KEY: misc_feature
<222> LOCATION: (14)..(15)
<223> OTHER INFORMATION: n is TrpdU
<220> FEATURE:
<221> NAME/KEY: misc_feature
<222> LOCATION: (18)..(18)
<223> OTHER INFORMATION: n is TrpdU
<220> FEATURE:
<221> NAME/KEY: misc_feature
<222> LOCATION: (20)..(21)
<223> OTHER INFORMATION: n is TrpdU
<220> FEATURE:
<221> NAME/KEY: misc_feature
<222> LOCATION: (26)..(26)
<223> OTHER INFORMATION: n is TrpdU
<220> FEATURE:
<221> NAME/KEY: misc_feature
<222> LOCATION: (29)..(31)
<223> OTHER INFORMATION: n is TrpdU
<220> FEATURE:
<221> NAME/KEY: misc_feature
<222> LOCATION: (33)..(33)
<223> OTHER INFORMATION: n is TrpdU
<220> FEATURE:
<221> NAME/KEY: misc_feature
<222> LOCATION: (37)..(37)
<223> OTHER INFORMATION: n is TrpdU
<220> FEATURE:
<221> NAME/KEY: misc_feature
<222> LOCATION: (39)..(39)
<223> OTHER INFORMATION: n is TrpdU

<400> SEQUENCE: 5
ctctganacg gccnnagngn nagagnccnn nangagncna gaccacaaca                 50

<210> SEQ ID NO 6
<211> LENGTH: 48
<212> TYPE: DNA
<213> ORGANISM: Artificial Sequence
<220> FEATURE:
<223> OTHER INFORMATION: Synthetic: 14583-49_4
<220> FEATURE:
<221> NAME/KEY: misc_feature
<222> LOCATION: (5)..(5)
<223> OTHER INFORMATION: n is TrpdU
<220> FEATURE:
<221> NAME/KEY: misc_feature
<222> LOCATION: (12)..(13)
<223> OTHER INFORMATION: n is TrpdU
<220> FEATURE:
<221> NAME/KEY: misc_feature
<222> LOCATION: (16)..(16)
<223> OTHER INFORMATION: n is TrpdU
<220> FEATURE:
<221> NAME/KEY: misc_feature
<222> LOCATION: (18)..(19)
<223> OTHER INFORMATION: n is TrpdU
<220> FEATURE:
```

```
<221> NAME/KEY: misc_feature
<222> LOCATION: (24)..(24)
<223> OTHER INFORMATION: n is TrpdU
<220> FEATURE:
<221> NAME/KEY: misc_feature
<222> LOCATION: (27)..(29)
<223> OTHER INFORMATION: n is TrpdU
<220> FEATURE:
<221> NAME/KEY: misc_feature
<222> LOCATION: (31)..(31)
<223> OTHER INFORMATION: n is TrpdU
<220> FEATURE:
<221> NAME/KEY: misc_feature
<222> LOCATION: (35)..(35)
<223> OTHER INFORMATION: n is TrpdU
<220> FEATURE:
<221> NAME/KEY: misc_feature
<222> LOCATION: (37)..(37)
<223> OTHER INFORMATION: n is TrpdU

<400> SEQUENCE: 6
ctganacggc cnnagngnna gagnccnnna ngagncnaga ccacaaca          48

<210> SEQ ID NO 7
<211> LENGTH: 46
<212> TYPE: DNA
<213> ORGANISM: Artificial Sequence
<220> FEATURE:
<223> OTHER INFORMATION: Synthetic: 14583-49_5
<220> FEATURE:
<221> NAME/KEY: misc_feature
<222> LOCATION: (3)..(3)
<223> OTHER INFORMATION: n is TrpdU
<220> FEATURE:
<221> NAME/KEY: misc_feature
<222> LOCATION: (10)..(11)
<223> OTHER INFORMATION: n is TrpdU
<220> FEATURE:
<221> NAME/KEY: misc_feature
<222> LOCATION: (14)..(14)
<223> OTHER INFORMATION: n is TrpdU
<220> FEATURE:
<221> NAME/KEY: misc_feature
<222> LOCATION: (16)..(17)
<223> OTHER INFORMATION: n is TrpdU
<220> FEATURE:
<221> NAME/KEY: misc_feature
<222> LOCATION: (22)..(22)
<223> OTHER INFORMATION: n is TrpdU
<220> FEATURE:
<221> NAME/KEY: misc_feature
<222> LOCATION: (25)..(27)
<223> OTHER INFORMATION: n is TrpdU
<220> FEATURE:
<221> NAME/KEY: misc_feature
<222> LOCATION: (29)..(29)
<223> OTHER INFORMATION: n is TrpdU
<220> FEATURE:
<221> NAME/KEY: misc_feature
<222> LOCATION: (33)..(33)
<223> OTHER INFORMATION: n is TrpdU
<220> FEATURE:
<221> NAME/KEY: misc_feature
<222> LOCATION: (35)..(35)
<223> OTHER INFORMATION: n is TrpdU

<400> SEQUENCE: 7
ganacggccn nagngnnaga gnccnnnang agncnagacc acaaca            46

<210> SEQ ID NO 8
<211> LENGTH: 44
<212> TYPE: DNA
<213> ORGANISM: Artificial Sequence
<220> FEATURE:
<223> OTHER INFORMATION: Synthetic: 14583-49_6
```

```
<220> FEATURE:
<221> NAME/KEY: misc_feature
<222> LOCATION: (1)..(1)
<223> OTHER INFORMATION: n is TrpdU
<220> FEATURE:
<221> NAME/KEY: misc_feature
<222> LOCATION: (8)..(9)
<223> OTHER INFORMATION: n is TrpdU
<220> FEATURE:
<221> NAME/KEY: misc_feature
<222> LOCATION: (12)..(12)
<223> OTHER INFORMATION: n is TrpdU
<220> FEATURE:
<221> NAME/KEY: misc_feature
<222> LOCATION: (14)..(15)
<223> OTHER INFORMATION: n is TrpdU
<220> FEATURE:
<221> NAME/KEY: misc_feature
<222> LOCATION: (20)..(20)
<223> OTHER INFORMATION: n is TrpdU
<220> FEATURE:
<221> NAME/KEY: misc_feature
<222> LOCATION: (23)..(25)
<223> OTHER INFORMATION: n is TrpdU
<220> FEATURE:
<221> NAME/KEY: misc_feature
<222> LOCATION: (27)..(27)
<223> OTHER INFORMATION: n is TrpdU
<220> FEATURE:
<221> NAME/KEY: misc_feature
<222> LOCATION: (31)..(31)
<223> OTHER INFORMATION: n is TrpdU
<220> FEATURE:
<221> NAME/KEY: misc_feature
<222> LOCATION: (33)..(33)
<223> OTHER INFORMATION: n is TrpdU

<400> SEQUENCE: 8
nacggccnna gngnnagagn ccnnnangag ncnagaccac aaca            44

<210> SEQ ID NO 9
<211> LENGTH: 42
<212> TYPE: DNA
<213> ORGANISM: Artificial Sequence
<220> FEATURE:
<223> OTHER INFORMATION: Synthetic: 14583-49_7
<220> FEATURE:
<221> NAME/KEY: misc_feature
<222> LOCATION: (6)..(7)
<223> OTHER INFORMATION: n is TrpdU
<220> FEATURE:
<221> NAME/KEY: misc_feature
<222> LOCATION: (10)..(10)
<223> OTHER INFORMATION: n is TrpdU
<220> FEATURE:
<221> NAME/KEY: misc_feature
<222> LOCATION: (12)..(13)
<223> OTHER INFORMATION: n is TrpdU
<220> FEATURE:
<221> NAME/KEY: misc_feature
<222> LOCATION: (18)..(18)
<223> OTHER INFORMATION: n is TrpdU
<220> FEATURE:
<221> NAME/KEY: misc_feature
<222> LOCATION: (21)..(23)
<223> OTHER INFORMATION: n is TrpdU
<220> FEATURE:
<221> NAME/KEY: misc_feature
<222> LOCATION: (25)..(25)
<223> OTHER INFORMATION: n is TrpdU
<220> FEATURE:
<221> NAME/KEY: misc_feature
<222> LOCATION: (29)..(29)
<223> OTHER INFORMATION: n is TrpdU
<220> FEATURE:
<221> NAME/KEY: misc_feature
<222> LOCATION: (31)..(31)
```

```
<223> OTHER INFORMATION: n is TrpdU

<400> SEQUENCE: 9
cggccnnagn gnnagagncc nnnangagnc nagaccacaa ca                              42

<210> SEQ ID NO 10
<211> LENGTH: 40
<212> TYPE: DNA
<213> ORGANISM: Artificial Sequence
<220> FEATURE:
<223> OTHER INFORMATION: Synthetic: 14583-49_8
<220> FEATURE:
<221> NAME/KEY: misc_feature
<222> LOCATION: (4)..(5)
<223> OTHER INFORMATION: n is TrpdU
<220> FEATURE:
<221> NAME/KEY: misc_feature
<222> LOCATION: (8)..(8)
<223> OTHER INFORMATION: n is TrpdU
<220> FEATURE:
<221> NAME/KEY: misc_feature
<222> LOCATION: (10)..(11)
<223> OTHER INFORMATION: n is TrpdU
<220> FEATURE:
<221> NAME/KEY: misc_feature
<222> LOCATION: (16)..(16)
<223> OTHER INFORMATION: n is TrpdU
<220> FEATURE:
<221> NAME/KEY: misc_feature
<222> LOCATION: (19)..(21)
<223> OTHER INFORMATION: n is TrpdU
<220> FEATURE:
<221> NAME/KEY: misc_feature
<222> LOCATION: (23)..(23)
<223> OTHER INFORMATION: n is TrpdU
<220> FEATURE:
<221> NAME/KEY: misc_feature
<222> LOCATION: (27)..(27)
<223> OTHER INFORMATION: n is TrpdU
<220> FEATURE:
<221> NAME/KEY: misc_feature
<222> LOCATION: (29)..(29)
<223> OTHER INFORMATION: n is TrpdU

<400> SEQUENCE: 10
gccnnagngn nagagnccnn nangagncna gaccacaaca                                 40

<210> SEQ ID NO 11
<211> LENGTH: 38
<212> TYPE: DNA
<213> ORGANISM: Artificial Sequence
<220> FEATURE:
<223> OTHER INFORMATION: Synthetic: 14583-49_9
<220> FEATURE:
<221> NAME/KEY: misc_feature
<222> LOCATION: (2)..(3)
<223> OTHER INFORMATION: n is TrpdU
<220> FEATURE:
<221> NAME/KEY: misc_feature
<222> LOCATION: (6)..(6)
<223> OTHER INFORMATION: n is TrpdU
<220> FEATURE:
<221> NAME/KEY: misc_feature
<222> LOCATION: (8)..(9)
<223> OTHER INFORMATION: n is TrpdU
<220> FEATURE:
<221> NAME/KEY: misc_feature
<222> LOCATION: (14)..(14)
<223> OTHER INFORMATION: n is TrpdU
<220> FEATURE:
<221> NAME/KEY: misc_feature
<222> LOCATION: (17)..(19)
<223> OTHER INFORMATION: n is TrpdU
<220> FEATURE:
<221> NAME/KEY: misc_feature
```

```
<222> LOCATION: (21)..(21)
<223> OTHER INFORMATION: n is TrpdU
<220> FEATURE:
<221> NAME/KEY: misc_feature
<222> LOCATION: (25)..(25)
<223> OTHER INFORMATION: n is TrpdU
<220> FEATURE:
<221> NAME/KEY: misc_feature
<222> LOCATION: (27)..(27)
<223> OTHER INFORMATION: n is TrpdU

<400> SEQUENCE: 11
cnnagngnna gagnccnnna ngagncnaga ccacaaca                    38

<210> SEQ ID NO 12
<211> LENGTH: 36
<212> TYPE: DNA
<213> ORGANISM: Artificial Sequence
<220> FEATURE:
<223> OTHER INFORMATION: Synthetic: 14583-49_10
<220> FEATURE:
<221> NAME/KEY: misc_feature
<222> LOCATION: (1)..(1)
<223> OTHER INFORMATION: n is TrpdU
<220> FEATURE:
<221> NAME/KEY: misc_feature
<222> LOCATION: (4)..(4)
<223> OTHER INFORMATION: n is TrpdU
<220> FEATURE:
<221> NAME/KEY: misc_feature
<222> LOCATION: (6)..(7)
<223> OTHER INFORMATION: n is TrpdU
<220> FEATURE:
<221> NAME/KEY: misc_feature
<222> LOCATION: (12)..(12)
<223> OTHER INFORMATION: n is TrpdU
<220> FEATURE:
<221> NAME/KEY: misc_feature
<222> LOCATION: (15)..(17)
<223> OTHER INFORMATION: n is TrpdU
<220> FEATURE:
<221> NAME/KEY: misc_feature
<222> LOCATION: (19)..(19)
<223> OTHER INFORMATION: n is TrpdU
<220> FEATURE:
<221> NAME/KEY: misc_feature
<222> LOCATION: (23)..(23)
<223> OTHER INFORMATION: n is TrpdU
<220> FEATURE:
<221> NAME/KEY: misc_feature
<222> LOCATION: (25)..(25)
<223> OTHER INFORMATION: n is TrpdU

<400> SEQUENCE: 12
nagngnnaga gnccnnnang agncnagacc acaaca                      36

<210> SEQ ID NO 13
<211> LENGTH: 34
<212> TYPE: DNA
<213> ORGANISM: Artificial Sequence
<220> FEATURE:
<223> OTHER INFORMATION: Synthetic: 14583-49_11
<220> FEATURE:
<221> NAME/KEY: misc_feature
<222> LOCATION: (2)..(2)
<223> OTHER INFORMATION: n is TrpdU
<220> FEATURE:
<221> NAME/KEY: misc_feature
<222> LOCATION: (4)..(5)
<223> OTHER INFORMATION: n is TrpdU
<220> FEATURE:
<221> NAME/KEY: misc_feature
<222> LOCATION: (10)..(10)
<223> OTHER INFORMATION: n is TrpdU
<220> FEATURE:
```

```
<221> NAME/KEY: misc_feature
<222> LOCATION: (13)..(15)
<223> OTHER INFORMATION: n is TrpdU
<220> FEATURE:
<221> NAME/KEY: misc_feature
<222> LOCATION: (17)..(17)
<223> OTHER INFORMATION: n is TrpdU
<220> FEATURE:
<221> NAME/KEY: misc_feature
<222> LOCATION: (21)..(21)
<223> OTHER INFORMATION: n is TrpdU
<220> FEATURE:
<221> NAME/KEY: misc_feature
<222> LOCATION: (23)..(23)
<223> OTHER INFORMATION: n is TrpdU

<400> SEQUENCE: 13
gngnnagagn ccnnnangag ncnagaccac aaca                                     34

<210> SEQ ID NO 14
<211> LENGTH: 32
<212> TYPE: DNA
<213> ORGANISM: Artificial Sequence
<220> FEATURE:
<223> OTHER INFORMATION: Synthetic: 14583-49_12
<220> FEATURE:
<221> NAME/KEY: misc_feature
<222> LOCATION: (2)..(3)
<223> OTHER INFORMATION: n is TrpdU
<220> FEATURE:
<221> NAME/KEY: misc_feature
<222> LOCATION: (8)..(8)
<223> OTHER INFORMATION: n is TrpdU
<220> FEATURE:
<221> NAME/KEY: misc_feature
<222> LOCATION: (11)..(13)
<223> OTHER INFORMATION: n is TrpdU
<220> FEATURE:
<221> NAME/KEY: misc_feature
<222> LOCATION: (15)..(15)
<223> OTHER INFORMATION: n is TrpdU
<220> FEATURE:
<221> NAME/KEY: misc_feature
<222> LOCATION: (19)..(19)
<223> OTHER INFORMATION: n is TrpdU
<220> FEATURE:
<221> NAME/KEY: misc_feature
<222> LOCATION: (21)..(21)
<223> OTHER INFORMATION: n is TrpdU

<400> SEQUENCE: 14
gnnagagncc nnnangagnc nagaccacaa ca                                       32

<210> SEQ ID NO 15
<211> LENGTH: 30
<212> TYPE: DNA
<213> ORGANISM: Artificial Sequence
<220> FEATURE:
<223> OTHER INFORMATION: Synthetic: 14583-49_13
<220> FEATURE:
<221> NAME/KEY: misc_feature
<222> LOCATION: (1)..(1)
<223> OTHER INFORMATION: n is TrpdU
<220> FEATURE:
<221> NAME/KEY: misc_feature
<222> LOCATION: (6)..(6)
<223> OTHER INFORMATION: n is TrpdU
<220> FEATURE:
<221> NAME/KEY: misc_feature
<222> LOCATION: (9)..(11)
<223> OTHER INFORMATION: n is TrpdU
<220> FEATURE:
<221> NAME/KEY: misc_feature
<222> LOCATION: (13)..(13)
<223> OTHER INFORMATION: n is TrpdU
```

```
<220> FEATURE:
<221> NAME/KEY: misc_feature
<222> LOCATION: (17)..(17)
<223> OTHER INFORMATION: n is TrpdU
<220> FEATURE:
<221> NAME/KEY: misc_feature
<222> LOCATION: (19)..(19)
<223> OTHER INFORMATION: n is TrpdU

<400> SEQUENCE: 15
nagagnccnn nangagncna gaccacaaca                              30

<210> SEQ ID NO 16
<211> LENGTH: 48
<212> TYPE: DNA
<213> ORGANISM: Artificial Sequence
<220> FEATURE:
<223> OTHER INFORMATION: Synthetic: 14583-49_14
<220> FEATURE:
<221> NAME/KEY: misc_feature
<222> LOCATION: (7)..(7)
<223> OTHER INFORMATION: n is TrpdU
<220> FEATURE:
<221> NAME/KEY: misc_feature
<222> LOCATION: (14)..(15)
<223> OTHER INFORMATION: n is TrpdU
<220> FEATURE:
<221> NAME/KEY: misc_feature
<222> LOCATION: (18)..(18)
<223> OTHER INFORMATION: n is TrpdU
<220> FEATURE:
<221> NAME/KEY: misc_feature
<222> LOCATION: (20)..(21)
<223> OTHER INFORMATION: n is TrpdU
<220> FEATURE:
<221> NAME/KEY: misc_feature
<222> LOCATION: (26)..(26)
<223> OTHER INFORMATION: n is TrpdU
<220> FEATURE:
<221> NAME/KEY: misc_feature
<222> LOCATION: (29)..(31)
<223> OTHER INFORMATION: n is TrpdU
<220> FEATURE:
<221> NAME/KEY: misc_feature
<222> LOCATION: (33)..(33)
<223> OTHER INFORMATION: n is TrpdU
<220> FEATURE:
<221> NAME/KEY: misc_feature
<222> LOCATION: (37)..(37)
<223> OTHER INFORMATION: n is TrpdU
<220> FEATURE:
<221> NAME/KEY: misc_feature
<222> LOCATION: (39)..(39)
<223> OTHER INFORMATION: n is TrpdU

<400> SEQUENCE: 16
ctctganacg gccnnagngn nagagnccnn nangagncna gaccacaa           48

<210> SEQ ID NO 17
<211> LENGTH: 46
<212> TYPE: DNA
<213> ORGANISM: Artificial Sequence
<220> FEATURE:
<223> OTHER INFORMATION: Synthetic: 14583-49_15
<220> FEATURE:
<221> NAME/KEY: misc_feature
<222> LOCATION: (7)..(7)
<223> OTHER INFORMATION: n is TrpdU
<220> FEATURE:
<221> NAME/KEY: misc_feature
<222> LOCATION: (14)..(15)
<223> OTHER INFORMATION: n is TrpdU
<220> FEATURE:
<221> NAME/KEY: misc_feature
<222> LOCATION: (18)..(18)
```

```
<223> OTHER INFORMATION: n is TrpdU
<220> FEATURE:
<221> NAME/KEY: misc_feature
<222> LOCATION: (20)..(21)
<223> OTHER INFORMATION: n is TrpdU
<220> FEATURE:
<221> NAME/KEY: misc_feature
<222> LOCATION: (26)..(26)
<223> OTHER INFORMATION: n is TrpdU
<220> FEATURE:
<221> NAME/KEY: misc_feature
<222> LOCATION: (29)..(31)
<223> OTHER INFORMATION: n is TrpdU
<220> FEATURE:
<221> NAME/KEY: misc_feature
<222> LOCATION: (33)..(33)
<223> OTHER INFORMATION: n is TrpdU
<220> FEATURE:
<221> NAME/KEY: misc_feature
<222> LOCATION: (37)..(37)
<223> OTHER INFORMATION: n is TrpdU
<220> FEATURE:
<221> NAME/KEY: misc_feature
<222> LOCATION: (39)..(39)
<223> OTHER INFORMATION: n is TrpdU

<400> SEQUENCE: 17
ctctganacg gccnnagngn nagagnccnn nangagncna gaccac                46

<210> SEQ ID NO 18
<211> LENGTH: 44
<212> TYPE: DNA
<213> ORGANISM: Artificial Sequence
<220> FEATURE:
<223> OTHER INFORMATION: Synthetic: 14583-49_16
<220> FEATURE:
<221> NAME/KEY: misc_feature
<222> LOCATION: (7)..(7)
<223> OTHER INFORMATION: n is TrpdU
<220> FEATURE:
<221> NAME/KEY: misc_feature
<222> LOCATION: (14)..(15)
<223> OTHER INFORMATION: n is TrpdU
<220> FEATURE:
<221> NAME/KEY: misc_feature
<222> LOCATION: (18)..(18)
<223> OTHER INFORMATION: n is TrpdU
<220> FEATURE:
<221> NAME/KEY: misc_feature
<222> LOCATION: (20)..(21)
<223> OTHER INFORMATION: n is TrpdU
<220> FEATURE:
<221> NAME/KEY: misc_feature
<222> LOCATION: (26)..(26)
<223> OTHER INFORMATION: n is TrpdU
<220> FEATURE:
<221> NAME/KEY: misc_feature
<222> LOCATION: (29)..(31)
<223> OTHER INFORMATION: n is TrpdU
<220> FEATURE:
<221> NAME/KEY: misc_feature
<222> LOCATION: (33)..(33)
<223> OTHER INFORMATION: n is TrpdU
<220> FEATURE:
<221> NAME/KEY: misc_feature
<222> LOCATION: (37)..(37)
<223> OTHER INFORMATION: n is TrpdU
<220> FEATURE:
<221> NAME/KEY: misc_feature
<222> LOCATION: (39)..(39)
<223> OTHER INFORMATION: n is TrpdU

<400> SEQUENCE: 18
ctctganacg gccnnagngn nagagnccnn nangagncna gacc                  44
```

-continued

```
<210> SEQ ID NO 19
<211> LENGTH: 42
<212> TYPE: DNA
<213> ORGANISM: Artificial Sequence
<220> FEATURE:
<223> OTHER INFORMATION: Synthetic: 14583-49_17
<220> FEATURE:
<221> NAME/KEY: misc_feature
<222> LOCATION: (7)..(7)
<223> OTHER INFORMATION: n is TrpdU
<220> FEATURE:
<221> NAME/KEY: misc_feature
<222> LOCATION: (14)..(15)
<223> OTHER INFORMATION: n is TrpdU
<220> FEATURE:
<221> NAME/KEY: misc_feature
<222> LOCATION: (18)..(18)
<223> OTHER INFORMATION: n is TrpdU
<220> FEATURE:
<221> NAME/KEY: misc_feature
<222> LOCATION: (20)..(21)
<223> OTHER INFORMATION: n is TrpdU
<220> FEATURE:
<221> NAME/KEY: misc_feature
<222> LOCATION: (26)..(26)
<223> OTHER INFORMATION: n is TrpdU
<220> FEATURE:
<221> NAME/KEY: misc_feature
<222> LOCATION: (29)..(31)
<223> OTHER INFORMATION: n is TrpdU
<220> FEATURE:
<221> NAME/KEY: misc_feature
<222> LOCATION: (33)..(33)
<223> OTHER INFORMATION: n is TrpdU
<220> FEATURE:
<221> NAME/KEY: misc_feature
<222> LOCATION: (37)..(37)
<223> OTHER INFORMATION: n is TrpdU
<220> FEATURE:
<221> NAME/KEY: misc_feature
<222> LOCATION: (39)..(39)
<223> OTHER INFORMATION: n is TrpdU

<400> SEQUENCE: 19
ctctganacg gccnnagngn nagagnccnn nangagncna ga                          42

<210> SEQ ID NO 20
<211> LENGTH: 40
<212> TYPE: DNA
<213> ORGANISM: Artificial Sequence
<220> FEATURE:
<223> OTHER INFORMATION: Synthetic: 14583-49_18
<220> FEATURE:
<221> NAME/KEY: misc_feature
<222> LOCATION: (7)..(7)
<223> OTHER INFORMATION: n is TrpdU
<220> FEATURE:
<221> NAME/KEY: misc_feature
<222> LOCATION: (14)..(15)
<223> OTHER INFORMATION: n is TrpdU
<220> FEATURE:
<221> NAME/KEY: misc_feature
<222> LOCATION: (18)..(18)
<223> OTHER INFORMATION: n is TrpdU
<220> FEATURE:
<221> NAME/KEY: misc_feature
<222> LOCATION: (20)..(21)
<223> OTHER INFORMATION: n is TrpdU
<220> FEATURE:
<221> NAME/KEY: misc_feature
<222> LOCATION: (26)..(26)
<223> OTHER INFORMATION: n is TrpdU
<220> FEATURE:
<221> NAME/KEY: misc_feature
<222> LOCATION: (29)..(31)
<223> OTHER INFORMATION: n is TrpdU
<220> FEATURE:
```

```
<221> NAME/KEY: misc_feature
<222> LOCATION: (33)..(33)
<223> OTHER INFORMATION: n is TrpdU
<220> FEATURE:
<221> NAME/KEY: misc_feature
<222> LOCATION: (37)..(37)
<223> OTHER INFORMATION: n is TrpdU
<220> FEATURE:
<221> NAME/KEY: misc_feature
<222> LOCATION: (39)..(39)
<223> OTHER INFORMATION: n is TrpdU

<400> SEQUENCE: 20
ctctganacg gccnnagngn nagagnccnn nangagncna                              40

<210> SEQ ID NO 21
<211> LENGTH: 38
<212> TYPE: DNA
<213> ORGANISM: Artificial Sequence
<220> FEATURE:
<223> OTHER INFORMATION: Synthetic: 14583-49_19
<220> FEATURE:
<221> NAME/KEY: misc_feature
<222> LOCATION: (7)..(7)
<223> OTHER INFORMATION: n is TrpdU
<220> FEATURE:
<221> NAME/KEY: misc_feature
<222> LOCATION: (14)..(15)
<223> OTHER INFORMATION: n is TrpdU
<220> FEATURE:
<221> NAME/KEY: misc_feature
<222> LOCATION: (18)..(18)
<223> OTHER INFORMATION: n is TrpdU
<220> FEATURE:
<221> NAME/KEY: misc_feature
<222> LOCATION: (20)..(21)
<223> OTHER INFORMATION: n is TrpdU
<220> FEATURE:
<221> NAME/KEY: misc_feature
<222> LOCATION: (26)..(26)
<223> OTHER INFORMATION: n is TrpdU
<220> FEATURE:
<221> NAME/KEY: misc_feature
<222> LOCATION: (29)..(31)
<223> OTHER INFORMATION: n is TrpdU
<220> FEATURE:
<221> NAME/KEY: misc_feature
<222> LOCATION: (33)..(33)
<223> OTHER INFORMATION: n is TrpdU
<220> FEATURE:
<221> NAME/KEY: misc_feature
<222> LOCATION: (37)..(37)
<223> OTHER INFORMATION: n is TrpdU

<400> SEQUENCE: 21
ctctganacg gccnnagngn nagagnccnn nangagnc                                38

<210> SEQ ID NO 22
<211> LENGTH: 36
<212> TYPE: DNA
<213> ORGANISM: Artificial Sequence
<220> FEATURE:
<223> OTHER INFORMATION: Synthetic: 14583-49_20
<220> FEATURE:
<221> NAME/KEY: misc_feature
<222> LOCATION: (7)..(7)
<223> OTHER INFORMATION: n is TrpdU
<220> FEATURE:
<221> NAME/KEY: misc_feature
<222> LOCATION: (14)..(15)
<223> OTHER INFORMATION: n is TrpdU
<220> FEATURE:
<221> NAME/KEY: misc_feature
<222> LOCATION: (18)..(18)
<223> OTHER INFORMATION: n is TrpdU
```

```
<220> FEATURE:
<221> NAME/KEY: misc_feature
<222> LOCATION: (20)..(21)
<223> OTHER INFORMATION: n is TrpdU
<220> FEATURE:
<221> NAME/KEY: misc_feature
<222> LOCATION: (26)..(26)
<223> OTHER INFORMATION: n is TrpdU
<220> FEATURE:
<221> NAME/KEY: misc_feature
<222> LOCATION: (29)..(31)
<223> OTHER INFORMATION: n is TrpdU
<220> FEATURE:
<221> NAME/KEY: misc_feature
<222> LOCATION: (33)..(33)
<223> OTHER INFORMATION: n is TrpdU

<400> SEQUENCE: 22
ctctganacg gccnnagngn nagagnccnn nangag                                    36

<210> SEQ ID NO 23
<211> LENGTH: 34
<212> TYPE: DNA
<213> ORGANISM: Artificial Sequence
<220> FEATURE:
<223> OTHER INFORMATION: Synthetic: 14583-49_21
<220> FEATURE:
<221> NAME/KEY: misc_feature
<222> LOCATION: (7)..(7)
<223> OTHER INFORMATION: n is TrpdU
<220> FEATURE:
<221> NAME/KEY: misc_feature
<222> LOCATION: (14)..(15)
<223> OTHER INFORMATION: n is TrpdU
<220> FEATURE:
<221> NAME/KEY: misc_feature
<222> LOCATION: (18)..(18)
<223> OTHER INFORMATION: n is TrpdU
<220> FEATURE:
<221> NAME/KEY: misc_feature
<222> LOCATION: (20)..(21)
<223> OTHER INFORMATION: n is TrpdU
<220> FEATURE:
<221> NAME/KEY: misc_feature
<222> LOCATION: (26)..(26)
<223> OTHER INFORMATION: n is TrpdU
<220> FEATURE:
<221> NAME/KEY: misc_feature
<222> LOCATION: (29)..(31)
<223> OTHER INFORMATION: n is TrpdU
<220> FEATURE:
<221> NAME/KEY: misc_feature
<222> LOCATION: (33)..(33)
<223> OTHER INFORMATION: n is TrpdU

<400> SEQUENCE: 23
ctctganacg gccnnagngn nagagnccnn nang                                      34

<210> SEQ ID NO 24
<211> LENGTH: 32
<212> TYPE: DNA
<213> ORGANISM: Artificial Sequence
<220> FEATURE:
<223> OTHER INFORMATION: Synthetic: 14583-49_22
<220> FEATURE:
<221> NAME/KEY: misc_feature
<222> LOCATION: (7)..(7)
<223> OTHER INFORMATION: n is TrpdU
<220> FEATURE:
<221> NAME/KEY: misc_feature
<222> LOCATION: (14)..(15)
<223> OTHER INFORMATION: n is TrpdU
<220> FEATURE:
<221> NAME/KEY: misc_feature
<222> LOCATION: (18)..(18)
```

```
<223> OTHER INFORMATION: n is TrpdU
<220> FEATURE:
<221> NAME/KEY: misc_feature
<222> LOCATION: (20)..(21)
<223> OTHER INFORMATION: n is TrpdU
<220> FEATURE:
<221> NAME/KEY: misc_feature
<222> LOCATION: (26)..(26)
<223> OTHER INFORMATION: n is TrpdU
<220> FEATURE:
<221> NAME/KEY: misc_feature
<222> LOCATION: (29)..(31)
<223> OTHER INFORMATION: n is TrpdU

<400> SEQUENCE: 24
ctctganacg gccnnagngn nagagnccnn na                                    32

<210> SEQ ID NO 25
<211> LENGTH: 30
<212> TYPE: DNA
<213> ORGANISM: Artificial Sequence
<220> FEATURE:
<223> OTHER INFORMATION: Synthetic: 14583-49_23
<220> FEATURE:
<221> NAME/KEY: misc_feature
<222> LOCATION: (7)..(7)
<223> OTHER INFORMATION: n is TrpdU
<220> FEATURE:
<221> NAME/KEY: misc_feature
<222> LOCATION: (14)..(15)
<223> OTHER INFORMATION: n is TrpdU
<220> FEATURE:
<221> NAME/KEY: misc_feature
<222> LOCATION: (18)..(18)
<223> OTHER INFORMATION: n is TrpdU
<220> FEATURE:
<221> NAME/KEY: misc_feature
<222> LOCATION: (20)..(21)
<223> OTHER INFORMATION: n is TrpdU
<220> FEATURE:
<221> NAME/KEY: misc_feature
<222> LOCATION: (26)..(26)
<223> OTHER INFORMATION: n is TrpdU
<220> FEATURE:
<221> NAME/KEY: misc_feature
<222> LOCATION: (29)..(30)
<223> OTHER INFORMATION: n is TrpdU

<400> SEQUENCE: 25
ctctganacg gccnnagngn nagagnccnn                                       30

<210> SEQ ID NO 26
<211> LENGTH: 26
<212> TYPE: DNA
<213> ORGANISM: Artificial Sequence
<220> FEATURE:
<223> OTHER INFORMATION: Synthetic: 14583-49_24
<220> FEATURE:
<221> NAME/KEY: misc_feature
<222> LOCATION: (2)..(2)
<223> OTHER INFORMATION: n is TrpdU
<220> FEATURE:
<221> NAME/KEY: misc_feature
<222> LOCATION: (4)..(5)
<223> OTHER INFORMATION: n is TrpdU
<220> FEATURE:
<221> NAME/KEY: misc_feature
<222> LOCATION: (10)..(10)
<223> OTHER INFORMATION: n is TrpdU
<220> FEATURE:
<221> NAME/KEY: misc_feature
<222> LOCATION: (13)..(15)
<223> OTHER INFORMATION: n is TrpdU
<220> FEATURE:
<221> NAME/KEY: misc_feature
```

```
<222> LOCATION: (17)..(17)
<223> OTHER INFORMATION: n is TrpdU
<220> FEATURE:
<221> NAME/KEY: misc_feature
<222> LOCATION: (21)..(21)
<223> OTHER INFORMATION: n is TrpdU
<220> FEATURE:
<221> NAME/KEY: misc_feature
<222> LOCATION: (23)..(23)
<223> OTHER INFORMATION: n is TrpdU

<400> SEQUENCE: 26
gngnnagagn ccnnnangag ncnaga                                    26

<210> SEQ ID NO 27
<211> LENGTH: 25
<212> TYPE: DNA
<213> ORGANISM: Artificial Sequence
<220> FEATURE:
<223> OTHER INFORMATION: Synthetic: 14583-49_25
<220> FEATURE:
<221> NAME/KEY: misc_feature
<222> LOCATION: (1)..(1)
<223> OTHER INFORMATION: n is TrpdU
<220> FEATURE:
<221> NAME/KEY: misc_feature
<222> LOCATION: (3)..(4)
<223> OTHER INFORMATION: n is TrpdU
<220> FEATURE:
<221> NAME/KEY: misc_feature
<222> LOCATION: (9)..(9)
<223> OTHER INFORMATION: n is TrpdU
<220> FEATURE:
<221> NAME/KEY: misc_feature
<222> LOCATION: (12)..(14)
<223> OTHER INFORMATION: n is TrpdU
<220> FEATURE:
<221> NAME/KEY: misc_feature
<222> LOCATION: (16)..(16)
<223> OTHER INFORMATION: n is TrpdU
<220> FEATURE:
<221> NAME/KEY: misc_feature
<222> LOCATION: (20)..(20)
<223> OTHER INFORMATION: n is TrpdU
<220> FEATURE:
<221> NAME/KEY: misc_feature
<222> LOCATION: (22)..(22)
<223> OTHER INFORMATION: n is TrpdU

<400> SEQUENCE: 27
ngnnagagnc cnnnangagn cnaga                                     25

<210> SEQ ID NO 28
<211> LENGTH: 24
<212> TYPE: DNA
<213> ORGANISM: Artificial Sequence
<220> FEATURE:
<223> OTHER INFORMATION: Synthetic: 14583-49_26
<220> FEATURE:
<221> NAME/KEY: misc_feature
<222> LOCATION: (2)..(3)
<223> OTHER INFORMATION: n is TrpdU
<220> FEATURE:
<221> NAME/KEY: misc_feature
<222> LOCATION: (8)..(8)
<223> OTHER INFORMATION: n is TrpdU
<220> FEATURE:
<221> NAME/KEY: misc_feature
<222> LOCATION: (11)..(13)
<223> OTHER INFORMATION: n is TrpdU
<220> FEATURE:
<221> NAME/KEY: misc_feature
<222> LOCATION: (15)..(15)
<223> OTHER INFORMATION: n is TrpdU
<220> FEATURE:
```

```
<221> NAME/KEY: misc_feature
<222> LOCATION: (19)..(19)
<223> OTHER INFORMATION: n is TrpdU
<220> FEATURE:
<221> NAME/KEY: misc_feature
<222> LOCATION: (21)..(21)
<223> OTHER INFORMATION: n is TrpdU

<400> SEQUENCE: 28
gnnagagncc nnnangagnc naga                                              24

<210> SEQ ID NO 29
<211> LENGTH: 23
<212> TYPE: DNA
<213> ORGANISM: Artificial Sequence
<220> FEATURE:
<223> OTHER INFORMATION: Synthetic: 14583-49_27
<220> FEATURE:
<221> NAME/KEY: misc_feature
<222> LOCATION: (1)..(2)
<223> OTHER INFORMATION: n is TrpdU
<220> FEATURE:
<221> NAME/KEY: misc_feature
<222> LOCATION: (7)..(7)
<223> OTHER INFORMATION: n is TrpdU
<220> FEATURE:
<221> NAME/KEY: misc_feature
<222> LOCATION: (10)..(12)
<223> OTHER INFORMATION: n is TrpdU
<220> FEATURE:
<221> NAME/KEY: misc_feature
<222> LOCATION: (14)..(14)
<223> OTHER INFORMATION: n is TrpdU
<220> FEATURE:
<221> NAME/KEY: misc_feature
<222> LOCATION: (18)..(18)
<223> OTHER INFORMATION: n is TrpdU
<220> FEATURE:
<221> NAME/KEY: misc_feature
<222> LOCATION: (20)..(20)
<223> OTHER INFORMATION: n is TrpdU

<400> SEQUENCE: 29
nnagagnccn nnangagncn aga                                               23

<210> SEQ ID NO 30
<211> LENGTH: 25
<212> TYPE: DNA
<213> ORGANISM: Artificial Sequence
<220> FEATURE:
<223> OTHER INFORMATION: Synthetic: 14583-49_28
<220> FEATURE:
<221> NAME/KEY: misc_feature
<222> LOCATION: (2)..(2)
<223> OTHER INFORMATION: n is TrpdU
<220> FEATURE:
<221> NAME/KEY: misc_feature
<222> LOCATION: (4)..(5)
<223> OTHER INFORMATION: n is TrpdU
<220> FEATURE:
<221> NAME/KEY: misc_feature
<222> LOCATION: (10)..(10)
<223> OTHER INFORMATION: n is TrpdU
<220> FEATURE:
<221> NAME/KEY: misc_feature
<222> LOCATION: (13)..(15)
<223> OTHER INFORMATION: n is TrpdU
<220> FEATURE:
<221> NAME/KEY: misc_feature
<222> LOCATION: (17)..(17)
<223> OTHER INFORMATION: n is TrpdU
<220> FEATURE:
<221> NAME/KEY: misc_feature
<222> LOCATION: (21)..(21)
<223> OTHER INFORMATION: n is TrpdU
```

<220> FEATURE:
<221> NAME/KEY: misc_feature
<222> LOCATION: (23)..(23)
<223> OTHER INFORMATION: n is TrpdU

<400> SEQUENCE: 30
gngnnagagn ccnnnangag ncnag                                              25

<210> SEQ ID NO 31
<211> LENGTH: 24
<212> TYPE: DNA
<213> ORGANISM: Artificial Sequence
<220> FEATURE:
<223> OTHER INFORMATION: Synthetic: 14583-49_29
<220> FEATURE:
<221> NAME/KEY: misc_feature
<222> LOCATION: (1)..(1)
<223> OTHER INFORMATION: n is TrpdU
<220> FEATURE:
<221> NAME/KEY: misc_feature
<222> LOCATION: (3)..(4)
<223> OTHER INFORMATION: n is TrpdU
<220> FEATURE:
<221> NAME/KEY: misc_feature
<222> LOCATION: (9)..(9)
<223> OTHER INFORMATION: n is TrpdU
<220> FEATURE:
<221> NAME/KEY: misc_feature
<222> LOCATION: (12)..(14)
<223> OTHER INFORMATION: n is TrpdU
<220> FEATURE:
<221> NAME/KEY: misc_feature
<222> LOCATION: (16)..(16)
<223> OTHER INFORMATION: n is TrpdU
<220> FEATURE:
<221> NAME/KEY: misc_feature
<222> LOCATION: (20)..(20)
<223> OTHER INFORMATION: n is TrpdU
<220> FEATURE:
<221> NAME/KEY: misc_feature
<222> LOCATION: (22)..(22)
<223> OTHER INFORMATION: n is TrpdU

<400> SEQUENCE: 31
ngnnagagnc cnnnangagn cnag                                               24

<210> SEQ ID NO 32
<211> LENGTH: 23
<212> TYPE: DNA
<213> ORGANISM: Artificial Sequence
<220> FEATURE:
<223> OTHER INFORMATION: Synthetic: 14583-49_30
<220> FEATURE:
<221> NAME/KEY: misc_feature
<222> LOCATION: (2)..(3)
<223> OTHER INFORMATION: n is TrpdU
<220> FEATURE:
<221> NAME/KEY: misc_feature
<222> LOCATION: (8)..(8)
<223> OTHER INFORMATION: n is TrpdU
<220> FEATURE:
<221> NAME/KEY: misc_feature
<222> LOCATION: (11)..(13)
<223> OTHER INFORMATION: n is TrpdU
<220> FEATURE:
<221> NAME/KEY: misc_feature
<222> LOCATION: (15)..(15)
<223> OTHER INFORMATION: n is TrpdU
<220> FEATURE:
<221> NAME/KEY: misc_feature
<222> LOCATION: (19)..(19)
<223> OTHER INFORMATION: n is TrpdU
<220> FEATURE:
<221> NAME/KEY: misc_feature
<222> LOCATION: (21)..(21)

```
<223> OTHER INFORMATION: n is TrpdU

<400> SEQUENCE: 32
gnnagagncc nnnangagnc nag                                              23

<210> SEQ ID NO 33
<211> LENGTH: 22
<212> TYPE: DNA
<213> ORGANISM: Artificial Sequence
<220> FEATURE:
<223> OTHER INFORMATION: Synthetic: 14583-49_31
<220> FEATURE:
<221> NAME/KEY: misc_feature
<222> LOCATION: (1)..(2)
<223> OTHER INFORMATION: n is TrpdU
<220> FEATURE:
<221> NAME/KEY: misc_feature
<222> LOCATION: (7)..(7)
<223> OTHER INFORMATION: n is TrpdU
<220> FEATURE:
<221> NAME/KEY: misc_feature
<222> LOCATION: (10)..(12)
<223> OTHER INFORMATION: n is TrpdU
<220> FEATURE:
<221> NAME/KEY: misc_feature
<222> LOCATION: (14)..(14)
<223> OTHER INFORMATION: n is TrpdU
<220> FEATURE:
<221> NAME/KEY: misc_feature
<222> LOCATION: (18)..(18)
<223> OTHER INFORMATION: n is TrpdU
<220> FEATURE:
<221> NAME/KEY: misc_feature
<222> LOCATION: (20)..(20)
<223> OTHER INFORMATION: n is TrpdU

<400> SEQUENCE: 33
nnagagnccn nnangagncn ag                                               22

<210> SEQ ID NO 34
<211> LENGTH: 40
<212> TYPE: DNA
<213> ORGANISM: Artificial Sequence
<220> FEATURE:
<223> OTHER INFORMATION: Synthetic: Aptamer Nucleotide Sequence
<220> FEATURE:
<221> NAME/KEY: misc_feature
<222> LOCATION: (2)..(2)
<223> OTHER INFORMATION: n is TrpdU
<220> FEATURE:
<221> NAME/KEY: misc_feature
<222> LOCATION: (9)..(10)
<223> OTHER INFORMATION: n is TrpdU
<220> FEATURE:
<221> NAME/KEY: misc_feature
<222> LOCATION: (13)..(13)
<223> OTHER INFORMATION: n is TrpdU
<220> FEATURE:
<221> NAME/KEY: misc_feature
<222> LOCATION: (15)..(16)
<223> OTHER INFORMATION: n is TrpdU
<220> FEATURE:
<221> NAME/KEY: misc_feature
<222> LOCATION: (21)..(21)
<223> OTHER INFORMATION: n is TrpdU
<220> FEATURE:
<221> NAME/KEY: misc_feature
<222> LOCATION: (24)..(26)
<223> OTHER INFORMATION: n is TrpdU
<220> FEATURE:
<221> NAME/KEY: misc_feature
<222> LOCATION: (28)..(28)
<223> OTHER INFORMATION: n is TrpdU
<220> FEATURE:
<221> NAME/KEY: misc_feature
```

<222> LOCATION: (32)..(32)
<223> OTHER INFORMATION: n is TrpdU
<220> FEATURE:
<221> NAME/KEY: misc_feature
<222> LOCATION: (34)..(34)
<223> OTHER INFORMATION: n is TrpdU

<400> SEQUENCE: 34
anacggccnn agngnnagag nccnnnanga gncnagacca                40

<210> SEQ ID NO 35
<211> LENGTH: 40
<212> TYPE: DNA
<213> ORGANISM: Artificial Sequence
<220> FEATURE:
<223> OTHER INFORMATION: Synthetic: Aptamer Nucleotide Sequence
<220> FEATURE:
<221> NAME/KEY: misc_feature
<222> LOCATION: (2)..(2)
<223> OTHER INFORMATION: n is TrpdU
<220> FEATURE:
<221> NAME/KEY: misc_feature
<222> LOCATION: (7)..(7)
<223> OTHER INFORMATION: n is TrpdU
<220> FEATURE:
<221> NAME/KEY: misc_feature
<222> LOCATION: (9)..(10)
<223> OTHER INFORMATION: n is TrpdU
<220> FEATURE:
<221> NAME/KEY: misc_feature
<222> LOCATION: (13)..(13)
<223> OTHER INFORMATION: n is TrpdU
<220> FEATURE:
<221> NAME/KEY: misc_feature
<222> LOCATION: (15)..(16)
<223> OTHER INFORMATION: n is TrpdU
<220> FEATURE:
<221> NAME/KEY: misc_feature
<222> LOCATION: (19)..(19)
<223> OTHER INFORMATION: n is TrpdU
<220> FEATURE:
<221> NAME/KEY: misc_feature
<222> LOCATION: (21)..(22)
<223> OTHER INFORMATION: n is TrpdU
<220> FEATURE:
<221> NAME/KEY: misc_feature
<222> LOCATION: (24)..(26)
<223> OTHER INFORMATION: n is TrpdU
<220> FEATURE:
<221> NAME/KEY: misc_feature
<222> LOCATION: (28)..(28)
<223> OTHER INFORMATION: n is TrpdU
<220> FEATURE:
<221> NAME/KEY: misc_feature
<222> LOCATION: (32)..(32)
<223> OTHER INFORMATION: n is TrpdU
<220> FEATURE:
<221> NAME/KEY: misc_feature
<222> LOCATION: (34)..(34)
<223> OTHER INFORMATION: n is TrpdU
<220> FEATURE:
<221> NAME/KEY: misc_feature
<222> LOCATION: (39)..(39)
<223> OTHER INFORMATION: n is TrpdU

<400> SEQUENCE: 35
anacagncnn agngnnagng nncnnnanga gncnagacng                40

<210> SEQ ID NO 36
<211> LENGTH: 40
<212> TYPE: DNA
<213> ORGANISM: Artificial Sequence
<220> FEATURE:
<223> OTHER INFORMATION: Synthetic: Aptamer Nucleotide Sequence
<220> FEATURE:

```
<221> NAME/KEY: misc_feature
<222> LOCATION: (2)..(2)
<223> OTHER INFORMATION: n is TrpdU
<220> FEATURE:
<221> NAME/KEY: misc_feature
<222> LOCATION: (4)..(4)
<223> OTHER INFORMATION: n is TrpdU
<220> FEATURE:
<221> NAME/KEY: misc_feature
<222> LOCATION: (9)..(10)
<223> OTHER INFORMATION: n is TrpdU
<220> FEATURE:
<221> NAME/KEY: misc_feature
<222> LOCATION: (13)..(13)
<223> OTHER INFORMATION: n is TrpdU
<220> FEATURE:
<221> NAME/KEY: misc_feature
<222> LOCATION: (15)..(16)
<223> OTHER INFORMATION: n is TrpdU
<220> FEATURE:
<221> NAME/KEY: misc_feature
<222> LOCATION: (19)..(19)
<223> OTHER INFORMATION: n is TrpdU
<220> FEATURE:
<221> NAME/KEY: misc_feature
<222> LOCATION: (21)..(22)
<223> OTHER INFORMATION: n is TrpdU
<220> FEATURE:
<221> NAME/KEY: misc_feature
<222> LOCATION: (24)..(26)
<223> OTHER INFORMATION: n is TrpdU
<220> FEATURE:
<221> NAME/KEY: misc_feature
<222> LOCATION: (28)..(28)
<223> OTHER INFORMATION: n is TrpdU
<220> FEATURE:
<221> NAME/KEY: misc_feature
<222> LOCATION: (32)..(32)
<223> OTHER INFORMATION: n is TrpdU
<220> FEATURE:
<221> NAME/KEY: misc_feature
<222> LOCATION: (34)..(34)
<223> OTHER INFORMATION: n is TrpdU
<220> FEATURE:
<221> NAME/KEY: misc_feature
<222> LOCATION: (38)..(38)
<223> OTHER INFORMATION: n is TrpdU

<400> SEQUENCE: 36
ananggccnn agngnnaaang nncnnnanga gncnagancg                          40

<210> SEQ ID NO 37
<211> LENGTH: 40
<212> TYPE: DNA
<213> ORGANISM: Artificial Sequence
<220> FEATURE:
<223> OTHER INFORMATION: Synthetic: Aptamer Nucleotide Sequence
<220> FEATURE:
<221> NAME/KEY: misc_feature
<222> LOCATION: (2)..(3)
<223> OTHER INFORMATION: n is TrpdU
<220> FEATURE:
<221> NAME/KEY: misc_feature
<222> LOCATION: (9)..(9)
<223> OTHER INFORMATION: n is TrpdU
<220> FEATURE:
<221> NAME/KEY: misc_feature
<222> LOCATION: (13)..(13)
<223> OTHER INFORMATION: n is TrpdU
<220> FEATURE:
<221> NAME/KEY: misc_feature
<222> LOCATION: (15)..(16)
<223> OTHER INFORMATION: n is TrpdU
<220> FEATURE:
<221> NAME/KEY: misc_feature
<222> LOCATION: (21)..(21)
<223> OTHER INFORMATION: n is TrpdU
```

```
<220> FEATURE:
<221> NAME/KEY: misc_feature
<222> LOCATION: (24)..(26)
<223> OTHER INFORMATION: n is TrpdU
<220> FEATURE:
<221> NAME/KEY: misc_feature
<222> LOCATION: (28)..(29)
<223> OTHER INFORMATION: n is TrpdU
<220> FEATURE:
<221> NAME/KEY: misc_feature
<222> LOCATION: (32)..(32)
<223> OTHER INFORMATION: n is TrpdU
<220> FEATURE:
<221> NAME/KEY: misc_feature
<222> LOCATION: (34)..(34)
<223> OTHER INFORMATION: n is TrpdU

<400> SEQUENCE: 37
anncggccnc agngnnggag nccnnnanna gncnagacag                    40

<210> SEQ ID NO 38
<211> LENGTH: 43
<212> TYPE: DNA
<213> ORGANISM: Artificial Sequence
<220> FEATURE:
<223> OTHER INFORMATION: Synthetic: Aptamer Nucleotide Sequence
<220> FEATURE:
<221> NAME/KEY: misc_feature
<222> LOCATION: (2)..(2)
<223> OTHER INFORMATION: n is TrpdU
<220> FEATURE:
<221> NAME/KEY: misc_feature
<222> LOCATION: (9)..(10)
<223> OTHER INFORMATION: n is TrpdU
<220> FEATURE:
<221> NAME/KEY: misc_feature
<222> LOCATION: (14)..(14)
<223> OTHER INFORMATION: n is TrpdU
<220> FEATURE:
<221> NAME/KEY: misc_feature
<222> LOCATION: (16)..(17)
<223> OTHER INFORMATION: n is TrpdU
<220> FEATURE:
<221> NAME/KEY: misc_feature
<222> LOCATION: (22)..(22)
<223> OTHER INFORMATION: n is TrpdU
<220> FEATURE:
<221> NAME/KEY: misc_feature
<222> LOCATION: (25)..(27)
<223> OTHER INFORMATION: n is TrpdU
<220> FEATURE:
<221> NAME/KEY: misc_feature
<222> LOCATION: (29)..(29)
<223> OTHER INFORMATION: n is TrpdU
<220> FEATURE:
<221> NAME/KEY: misc_feature
<222> LOCATION: (33)..(34)
<223> OTHER INFORMATION: n is TrpdU
<220> FEATURE:
<221> NAME/KEY: misc_feature
<222> LOCATION: (36)..(36)
<223> OTHER INFORMATION: n is TrpdU
<220> FEATURE:
<221> NAME/KEY: misc_feature
<222> LOCATION: (41)..(41)
<223> OTHER INFORMATION: n is TrpdU

<400> SEQUENCE: 38
anacgaccnn acgngnnaga gnccnnnang agnncnaaga ncg                43

<210> SEQ ID NO 39
<211> LENGTH: 40
<212> TYPE: DNA
<213> ORGANISM: Artificial Sequence
<220> FEATURE:
```

```
<223> OTHER INFORMATION: Synthetic: Aptamer Nucleotide Sequence
<220> FEATURE:
<221> NAME/KEY: misc_feature
<222> LOCATION: (2)..(2)
<223> OTHER INFORMATION: n is TrpdU
<220> FEATURE:
<221> NAME/KEY: misc_feature
<222> LOCATION: (6)..(6)
<223> OTHER INFORMATION: n is TrpdU
<220> FEATURE:
<221> NAME/KEY: misc_feature
<222> LOCATION: (9)..(10)
<223> OTHER INFORMATION: n is TrpdU
<220> FEATURE:
<221> NAME/KEY: misc_feature
<222> LOCATION: (13)..(13)
<223> OTHER INFORMATION: n is TrpdU
<220> FEATURE:
<221> NAME/KEY: misc_feature
<222> LOCATION: (15)..(16)
<223> OTHER INFORMATION: n is TrpdU
<220> FEATURE:
<221> NAME/KEY: misc_feature
<222> LOCATION: (19)..(19)
<223> OTHER INFORMATION: n is TrpdU
<220> FEATURE:
<221> NAME/KEY: misc_feature
<222> LOCATION: (21)..(21)
<223> OTHER INFORMATION: n is TrpdU
<220> FEATURE:
<221> NAME/KEY: misc_feature
<222> LOCATION: (24)..(25)
<223> OTHER INFORMATION: n is TrpdU
<220> FEATURE:
<221> NAME/KEY: misc_feature
<222> LOCATION: (28)..(28)
<223> OTHER INFORMATION: n is TrpdU
<220> FEATURE:
<221> NAME/KEY: misc_feature
<222> LOCATION: (32)..(32)
<223> OTHER INFORMATION: n is TrpdU
<220> FEATURE:
<221> NAME/KEY: misc_feature
<222> LOCATION: (34)..(34)
<223> OTHER INFORMATION: n is TrpdU

<400> SEQUENCE: 39
anacanccnn agngnnagng nccnncgnga gncnagaccg                              40

<210> SEQ ID NO 40
<211> LENGTH: 42
<212> TYPE: DNA
<213> ORGANISM: Artificial Sequence
<220> FEATURE:
<223> OTHER INFORMATION: Synthetic: Aptamer Nucleotide Sequence
<220> FEATURE:
<221> NAME/KEY: misc_feature
<222> LOCATION: (2)..(2)
<223> OTHER INFORMATION: n is TrpdU
<220> FEATURE:
<221> NAME/KEY: misc_feature
<222> LOCATION: (7)..(7)
<223> OTHER INFORMATION: n is TrpdU
<220> FEATURE:
<221> NAME/KEY: misc_feature
<222> LOCATION: (9)..(10)
<223> OTHER INFORMATION: n is TrpdU
<220> FEATURE:
<221> NAME/KEY: misc_feature
<222> LOCATION: (13)..(13)
<223> OTHER INFORMATION: n is TrpdU
<220> FEATURE:
<221> NAME/KEY: misc_feature
<222> LOCATION: (15)..(16)
<223> OTHER INFORMATION: n is TrpdU
<220> FEATURE:
<221> NAME/KEY: misc_feature
```

```
<222> LOCATION: (21)..(21)
<223> OTHER INFORMATION: n is TrpdU
<220> FEATURE:
<221> NAME/KEY: misc_feature
<222> LOCATION: (25)..(28)
<223> OTHER INFORMATION: n is TrpdU
<220> FEATURE:
<221> NAME/KEY: misc_feature
<222> LOCATION: (30)..(30)
<223> OTHER INFORMATION: n is TrpdU
<220> FEATURE:
<221> NAME/KEY: misc_feature
<222> LOCATION: (34)..(34)
<223> OTHER INFORMATION: n is TrpdU
<220> FEATURE:
<221> NAME/KEY: misc_feature
<222> LOCATION: (36)..(36)
<223> OTHER INFORMATION: n is TrpdU
<220> FEATURE:
<221> NAME/KEY: misc_feature
<222> LOCATION: (40)..(41)
<223> OTHER INFORMATION: n is TrpdU

<400> SEQUENCE: 40
anacggncnn agngnnagag ncccnnnnan gagncnagan ng                    42

<210> SEQ ID NO 41
<211> LENGTH: 41
<212> TYPE: DNA
<213> ORGANISM: Artificial Sequence
<220> FEATURE:
<223> OTHER INFORMATION: Synthetic: Aptamer Nucleotide Sequence
<220> FEATURE:
<221> NAME/KEY: misc_feature
<222> LOCATION: (2)..(2)
<223> OTHER INFORMATION: n is TrpdU
<220> FEATURE:
<221> NAME/KEY: misc_feature
<222> LOCATION: (9)..(10)
<223> OTHER INFORMATION: n is TrpdU
<220> FEATURE:
<221> NAME/KEY: misc_feature
<222> LOCATION: (15)..(16)
<223> OTHER INFORMATION: n is TrpdU
<220> FEATURE:
<221> NAME/KEY: misc_feature
<222> LOCATION: (21)..(21)
<223> OTHER INFORMATION: n is TrpdU
<220> FEATURE:
<221> NAME/KEY: misc_feature
<222> LOCATION: (24)..(26)
<223> OTHER INFORMATION: n is TrpdU
<220> FEATURE:
<221> NAME/KEY: misc_feature
<222> LOCATION: (32)..(32)
<223> OTHER INFORMATION: n is TrpdU
<220> FEATURE:
<221> NAME/KEY: misc_feature
<222> LOCATION: (34)..(34)
<223> OTHER INFORMATION: n is TrpdU
<220> FEATURE:
<221> NAME/KEY: misc_feature
<222> LOCATION: (38)..(39)
<223> OTHER INFORMATION: n is TrpdU

<400> SEQUENCE: 41
anacggccnn agcgnnagag nccnnnacga gncnaganng c                     41

<210> SEQ ID NO 42
<211> LENGTH: 42
<212> TYPE: DNA
<213> ORGANISM: Artificial Sequence
<220> FEATURE:
<223> OTHER INFORMATION: Synthetic: Aptamer Nucleotide Sequence
<220> FEATURE:
```

<221> NAME/KEY: misc_feature
<222> LOCATION: (2)..(3)
<223> OTHER INFORMATION: n is TrpdU
<220> FEATURE:
<221> NAME/KEY: misc_feature
<222> LOCATION: (10)..(11)
<223> OTHER INFORMATION: n is TrpdU
<220> FEATURE:
<221> NAME/KEY: misc_feature
<222> LOCATION: (14)..(14)
<223> OTHER INFORMATION: n is TrpdU
<220> FEATURE:
<221> NAME/KEY: misc_feature
<222> LOCATION: (16)..(17)
<223> OTHER INFORMATION: n is TrpdU
<220> FEATURE:
<221> NAME/KEY: misc_feature
<222> LOCATION: (22)..(22)
<223> OTHER INFORMATION: n is TrpdU
<220> FEATURE:
<221> NAME/KEY: misc_feature
<222> LOCATION: (25)..(27)
<223> OTHER INFORMATION: n is TrpdU
<220> FEATURE:
<221> NAME/KEY: misc_feature
<222> LOCATION: (29)..(29)
<223> OTHER INFORMATION: n is TrpdU
<220> FEATURE:
<221> NAME/KEY: misc_feature
<222> LOCATION: (31)..(31)
<223> OTHER INFORMATION: n is TrpdU
<220> FEATURE:
<221> NAME/KEY: misc_feature
<222> LOCATION: (35)..(35)
<223> OTHER INFORMATION: n is TrpdU
<220> FEATURE:
<221> NAME/KEY: misc_feature
<222> LOCATION: (37)..(37)
<223> OTHER INFORMATION: n is TrpdU
<220> FEATURE:
<221> NAME/KEY: misc_feature
<222> LOCATION: (41)..(41)
<223> OTHER INFORMATION: n is TrpdU

<400> SEQUENCE: 42
annacggcan nagngnnaga gnccnnnang nagcncnaga ng                42

<210> SEQ ID NO 43
<211> LENGTH: 40
<212> TYPE: DNA
<213> ORGANISM: Artificial Sequence
<220> FEATURE:
<223> OTHER INFORMATION: Synthetic: Aptamer Nucleotide Sequence
<220> FEATURE:
<221> NAME/KEY: misc_feature
<222> LOCATION: (2)..(2)
<223> OTHER INFORMATION: n is TrpdU
<220> FEATURE:
<221> NAME/KEY: misc_feature
<222> LOCATION: (10)..(10)
<223> OTHER INFORMATION: n is TrpdU
<220> FEATURE:
<221> NAME/KEY: misc_feature
<222> LOCATION: (13)..(13)
<223> OTHER INFORMATION: n is TrpdU
<220> FEATURE:
<221> NAME/KEY: misc_feature
<222> LOCATION: (15)..(16)
<223> OTHER INFORMATION: n is TrpdU
<220> FEATURE:
<221> NAME/KEY: misc_feature
<222> LOCATION: (21)..(22)
<223> OTHER INFORMATION: n is TrpdU
<220> FEATURE:
<221> NAME/KEY: misc_feature
<222> LOCATION: (24)..(26)
<223> OTHER INFORMATION: n is TrpdU

```
<220> FEATURE:
<221> NAME/KEY: misc_feature
<222> LOCATION: (28)..(28)
<223> OTHER INFORMATION: n is TrpdU
<220> FEATURE:
<221> NAME/KEY: misc_feature
<222> LOCATION: (32)..(32)
<223> OTHER INFORMATION: n is TrpdU
<220> FEATURE:
<221> NAME/KEY: misc_feature
<222> LOCATION: (34)..(34)
<223> OTHER INFORMATION: n is TrpdU
<220> FEATURE:
<221> NAME/KEY: misc_feature
<222> LOCATION: (38)..(38)
<223> OTHER INFORMATION: n is TrpdU

<400> SEQUENCE: 43
angcgaccan agngnnagag nncnnnanga gncnagancg                            40

<210> SEQ ID NO 44
<211> LENGTH: 33
<212> TYPE: DNA
<213> ORGANISM: Artificial Sequence
<220> FEATURE:
<223> OTHER INFORMATION: Synthetic: Aptamer Nucleotide Sequence
<220> FEATURE:
<221> NAME/KEY: misc_feature
<222> LOCATION: (3)..(3)
<223> OTHER INFORMATION: n is TrpdU
<220> FEATURE:
<221> NAME/KEY: misc_feature
<222> LOCATION: (6)..(6)
<223> OTHER INFORMATION: n is TrpdU
<220> FEATURE:
<221> NAME/KEY: misc_feature
<222> LOCATION: (8)..(9)
<223> OTHER INFORMATION: n is TrpdU
<220> FEATURE:
<221> NAME/KEY: misc_feature
<222> LOCATION: (12)..(12)
<223> OTHER INFORMATION: n is TrpdU
<220> FEATURE:
<221> NAME/KEY: misc_feature
<222> LOCATION: (14)..(15)
<223> OTHER INFORMATION: n is TrpdU
<220> FEATURE:
<221> NAME/KEY: misc_feature
<222> LOCATION: (17)..(19)
<223> OTHER INFORMATION: n is TrpdU
<220> FEATURE:
<221> NAME/KEY: misc_feature
<222> LOCATION: (21)..(21)
<223> OTHER INFORMATION: n is TrpdU
<220> FEATURE:
<221> NAME/KEY: misc_feature
<222> LOCATION: (25)..(25)
<223> OTHER INFORMATION: n is TrpdU
<220> FEATURE:
<221> NAME/KEY: misc_feature
<222> LOCATION: (27)..(27)
<223> OTHER INFORMATION: n is TrpdU

<400> SEQUENCE: 44
ccnagngnna gngnncnnna ngagncnaga ccg                                   33

<210> SEQ ID NO 45
<211> LENGTH: 40
<212> TYPE: DNA
<213> ORGANISM: Artificial Sequence
<220> FEATURE:
<223> OTHER INFORMATION: Synthetic: Aptamer Nucleotide Sequence
<220> FEATURE:
<221> NAME/KEY: misc_feature
<222> LOCATION: (2)..(2)
```

```
<223> OTHER INFORMATION: n is TrpdU
<220> FEATURE:
<221> NAME/KEY: misc_feature
<222> LOCATION: (4)..(4)
<223> OTHER INFORMATION: n is TrpdU
<220> FEATURE:
<221> NAME/KEY: misc_feature
<222> LOCATION: (10)..(10)
<223> OTHER INFORMATION: n is TrpdU
<220> FEATURE:
<221> NAME/KEY: misc_feature
<222> LOCATION: (13)..(13)
<223> OTHER INFORMATION: n is TrpdU
<220> FEATURE:
<221> NAME/KEY: misc_feature
<222> LOCATION: (15)..(16)
<223> OTHER INFORMATION: n is TrpdU
<220> FEATURE:
<221> NAME/KEY: misc_feature
<222> LOCATION: (21)..(22)
<223> OTHER INFORMATION: n is TrpdU
<220> FEATURE:
<221> NAME/KEY: misc_feature
<222> LOCATION: (24)..(25)
<223> OTHER INFORMATION: n is TrpdU
<220> FEATURE:
<221> NAME/KEY: misc_feature
<222> LOCATION: (28)..(28)
<223> OTHER INFORMATION: n is TrpdU
<220> FEATURE:
<221> NAME/KEY: misc_feature
<222> LOCATION: (32)..(32)
<223> OTHER INFORMATION: n is TrpdU
<220> FEATURE:
<221> NAME/KEY: misc_feature
<222> LOCATION: (34)..(34)
<223> OTHER INFORMATION: n is TrpdU

<400> SEQUENCE: 45
ananggcccn agngnnagag nncnncanga gncnagacgg                           40

<210> SEQ ID NO 46
<211> LENGTH: 41
<212> TYPE: DNA
<213> ORGANISM: Artificial Sequence
<220> FEATURE:
<223> OTHER INFORMATION: Synthetic: Aptamer Nucleotide Sequence
<220> FEATURE:
<221> NAME/KEY: misc_feature
<222> LOCATION: (2)..(2)
<223> OTHER INFORMATION: n is TrpdU
<220> FEATURE:
<221> NAME/KEY: misc_feature
<222> LOCATION: (4)..(4)
<223> OTHER INFORMATION: n is TrpdU
<220> FEATURE:
<221> NAME/KEY: misc_feature
<222> LOCATION: (8)..(9)
<223> OTHER INFORMATION: n is TrpdU
<220> FEATURE:
<221> NAME/KEY: misc_feature
<222> LOCATION: (12)..(12)
<223> OTHER INFORMATION: n is TrpdU
<220> FEATURE:
<221> NAME/KEY: misc_feature
<222> LOCATION: (14)..(15)
<223> OTHER INFORMATION: n is TrpdU
<220> FEATURE:
<221> NAME/KEY: misc_feature
<222> LOCATION: (20)..(20)
<223> OTHER INFORMATION: n is TrpdU
<220> FEATURE:
<221> NAME/KEY: misc_feature
<222> LOCATION: (23)..(25)
<223> OTHER INFORMATION: n is TrpdU
<220> FEATURE:
<221> NAME/KEY: misc_feature
```

```
<222> LOCATION: (29)..(29)
<223> OTHER INFORMATION: n is TrpdU
<220> FEATURE:
<221> NAME/KEY: misc_feature
<222> LOCATION: (33)..(33)
<223> OTHER INFORMATION: n is TrpdU
<220> FEATURE:
<221> NAME/KEY: misc_feature
<222> LOCATION: (35)..(35)
<223> OTHER INFORMATION: n is TrpdU
<220> FEATURE:
<221> NAME/KEY: misc_feature
<222> LOCATION: (39)..(39)
<223> OTHER INFORMATION: n is TrpdU

<400> SEQUENCE: 46
anangccnna gngnnagagn ccnnnaacng agncnaganc g                41

<210> SEQ ID NO 47
<211> LENGTH: 42
<212> TYPE: DNA
<213> ORGANISM: Artificial Sequence
<220> FEATURE:
<223> OTHER INFORMATION: Synthetic: Aptamer Nucleotide Sequence
<220> FEATURE:
<221> NAME/KEY: misc_feature
<222> LOCATION: (2)..(2)
<223> OTHER INFORMATION: n is TrpdU
<220> FEATURE:
<221> NAME/KEY: misc_feature
<222> LOCATION: (9)..(9)
<223> OTHER INFORMATION: n is TrpdU
<220> FEATURE:
<221> NAME/KEY: misc_feature
<222> LOCATION: (12)..(12)
<223> OTHER INFORMATION: n is TrpdU
<220> FEATURE:
<221> NAME/KEY: misc_feature
<222> LOCATION: (14)..(15)
<223> OTHER INFORMATION: n is TrpdU
<220> FEATURE:
<221> NAME/KEY: misc_feature
<222> LOCATION: (22)..(22)
<223> OTHER INFORMATION: n is TrpdU
<220> FEATURE:
<221> NAME/KEY: misc_feature
<222> LOCATION: (25)..(27)
<223> OTHER INFORMATION: n is TrpdU
<220> FEATURE:
<221> NAME/KEY: misc_feature
<222> LOCATION: (29)..(29)
<223> OTHER INFORMATION: n is TrpdU
<220> FEATURE:
<221> NAME/KEY: misc_feature
<222> LOCATION: (33)..(33)
<223> OTHER INFORMATION: n is TrpdU
<220> FEATURE:
<221> NAME/KEY: misc_feature
<222> LOCATION: (35)..(35)
<223> OTHER INFORMATION: n is TrpdU
<220> FEATURE:
<221> NAME/KEY: misc_feature
<222> LOCATION: (41)..(41)
<223> OTHER INFORMATION: n is TrpdU

<400> SEQUENCE: 47
anacgaccna gngnnacgag gnccnnnang agncnagacg na               42

<210> SEQ ID NO 48
<211> LENGTH: 44
<212> TYPE: DNA
<213> ORGANISM: Artificial Sequence
<220> FEATURE:
<223> OTHER INFORMATION: Synthetic: Aptamer Nucleotide Sequence
<220> FEATURE:
```

<221> NAME/KEY: misc_feature
<222> LOCATION: (2)..(2)
<223> OTHER INFORMATION: n is TrpdU
<220> FEATURE:
<221> NAME/KEY: misc_feature
<222> LOCATION: (4)..(4)
<223> OTHER INFORMATION: n is TrpdU
<220> FEATURE:
<221> NAME/KEY: misc_feature
<222> LOCATION: (9)..(10)
<223> OTHER INFORMATION: n is TrpdU
<220> FEATURE:
<221> NAME/KEY: misc_feature
<222> LOCATION: (13)..(13)
<223> OTHER INFORMATION: n is TrpdU
<220> FEATURE:
<221> NAME/KEY: misc_feature
<222> LOCATION: (15)..(16)
<223> OTHER INFORMATION: n is TrpdU
<220> FEATURE:
<221> NAME/KEY: misc_feature
<222> LOCATION: (21)..(21)
<223> OTHER INFORMATION: n is TrpdU
<220> FEATURE:
<221> NAME/KEY: misc_feature
<222> LOCATION: (24)..(26)
<223> OTHER INFORMATION: n is TrpdU
<220> FEATURE:
<221> NAME/KEY: misc_feature
<222> LOCATION: (28)..(28)
<223> OTHER INFORMATION: n is TrpdU
<220> FEATURE:
<221> NAME/KEY: misc_feature
<222> LOCATION: (32)..(32)
<223> OTHER INFORMATION: n is TrpdU
<220> FEATURE:
<221> NAME/KEY: misc_feature
<222> LOCATION: (35)..(36)
<223> OTHER INFORMATION: n is TrpdU
<220> FEATURE:
<221> NAME/KEY: misc_feature
<222> LOCATION: (41)..(41)
<223> OTHER INFORMATION: n is TrpdU

<400> SEQUENCE: 48
ananggccnn agngnnagag nccnnnanga gnccnnagac ngac          44

<210> SEQ ID NO 49
<211> LENGTH: 27
<212> TYPE: DNA
<213> ORGANISM: Artificial Sequence
<220> FEATURE:
<223> OTHER INFORMATION: Synthetic: aptamer that binds GDF8
<220> FEATURE:
<221> NAME/KEY: misc_feature
<222> LOCATION: (2)..(3)
<223> OTHER INFORMATION: n is a C-5 modified pyrimidine
<220> FEATURE:
<221> NAME/KEY: misc_feature
<222> LOCATION: (6)..(6)
<223> OTHER INFORMATION: n is a or C-5 modified pyrimidine
<220> FEATURE:
<221> NAME/KEY: misc_feature
<222> LOCATION: (8)..(8)
<223> OTHER INFORMATION: n is a C-5 modified pyrimidine
<220> FEATURE:
<221> NAME/KEY: misc_feature
<222> LOCATION: (9)..(9)
<223> OTHER INFORMATION: may not be present
<220> FEATURE:
<221> NAME/KEY: misc_feature
<222> LOCATION: (10)..(10)
<223> OTHER INFORMATION: n is C-5 modified pyrimidine or c
<220> FEATURE:
<221> NAME/KEY: misc_feature
<222> LOCATION: (12)..(12)
<223> OTHER INFORMATION: n, if present, is C-5 modified pyrimidine

```
<220> FEATURE:
<221> NAME/KEY: misc_feature
<222> LOCATION: (13)..(14)
<223> OTHER INFORMATION: n is C-5 modified pyrimidine
<220> FEATURE:
<221> NAME/KEY: misc_feature
<222> LOCATION: (15)..(15)
<223> OTHER INFORMATION: n is C-5 modified pyrimidine or c
<220> FEATURE:
<221> NAME/KEY: misc_feature
<222> LOCATION: (16)..(16)
<223> OTHER INFORMATION: may not be present
<220> FEATURE:
<221> NAME/KEY: misc_feature
<222> LOCATION: (18)..(18)
<223> OTHER INFORMATION: may not be present
<220> FEATURE:
<221> NAME/KEY: misc_feature
<222> LOCATION: (19)..(19)
<223> OTHER INFORMATION: n is C-5 modified pyrimidine or c
<220> FEATURE:
<221> NAME/KEY: misc_feature
<222> LOCATION: (20)..(20)
<223> OTHER INFORMATION: n is g or C-5 modified pyrimidine
<220> FEATURE:
<221> NAME/KEY: misc_feature
<222> LOCATION: (23)..(23)
<223> OTHER INFORMATION: n is C-5 modified pyrimidine
<220> FEATURE:
<221> NAME/KEY: misc_feature
<222> LOCATION: (25)..(25)
<223> OTHER INFORMATION: n is C-5 modified pyrimidine or c
<220> FEATURE:
<221> NAME/KEY: misc_feature
<222> LOCATION: (26)..(26)
<223> OTHER INFORMATION: n is a or C-5 modified pyrimidine
<220> FEATURE:
<221> NAME/KEY: misc_feature
<222> LOCATION: (27)..(27)
<223> OTHER INFORMATION: n is g, a or C-5 modified pyrimidine

<400> SEQUENCE: 49
gnnrrngncn cnnnnarcnn agncnnn                                              27

<210> SEQ ID NO 50
<211> LENGTH: 109
<212> TYPE: PRT
<213> ORGANISM: Homo sapiens
<220> FEATURE:
<221> NAME/KEY: misc_feature
<222> LOCATION: (1)..(109)
<223> OTHER INFORMATION: nonlimiting exemplary mature human GDF11
      protein

<400> SEQUENCE: 50

Asn Leu Gly Leu Asp Cys Asp Glu His Ser Ser Glu Ser Arg Cys Cys
1               5                   10                  15

Arg Tyr Pro Leu Thr Val Asp Phe Glu Ala Phe Gly Trp Asp Trp Ile
            20                  25                  30

Ile Ala Pro Lys Arg Tyr Lys Ala Asn Tyr Cys Ser Gly Gln Cys Glu
        35                  40                  45

Tyr Met Phe Met Gln Lys Tyr Pro His Thr His Leu Val Gln Gln Ala
    50                  55                  60

Asn Pro Arg Gly Ser Ala Gly Pro Cys Cys Thr Pro Thr Lys Met Ser
65                  70                  75                  80

Pro Ile Asn Met Leu Tyr Phe Asn Asp Lys Gln Gln Ile Ile Tyr Gly
                85                  90                  95

Lys Ile Pro Gly Met Val Val Asp Arg Cys Gly Cys Ser
            100                 105
```

```
<210> SEQ ID NO 51
<211> LENGTH: 109
<212> TYPE: PRT
<213> ORGANISM: Homo sapiens
<220> FEATURE:
<221> NAME/KEY: misc_feature
<222> LOCATION: (1)..(109)
<223> OTHER INFORMATION: Human myostatin (GDF8) Protein ID is O14793;
      exemplary human mature GDF8

<400> SEQUENCE: 51

Asp Phe Gly Leu Asp Cys Asp Glu His Ser Thr Glu Ser Arg Cys Cys
1               5                   10                  15

Arg Tyr Pro Leu Thr Val Asp Phe Glu Ala Phe Gly Trp Asp Trp Ile
            20                  25                  30

Ile Ala Pro Lys Arg Tyr Lys Ala Asn Tyr Cys Ser Gly Glu Cys Glu
        35                  40                  45

Phe Val Phe Leu Gln Lys Tyr Pro His Thr His Leu Val His Gln Ala
    50                  55                  60

Asn Pro Arg Gly Ser Ala Gly Pro Cys Cys Thr Pro Thr Lys Met Ser
65                  70                  75                  80

Pro Ile Asn Met Leu Tyr Phe Asn Gly Lys Glu Gln Ile Ile Tyr Gly
                85                  90                  95

Lys Ile Pro Ala Met Val Val Asp Arg Cys Gly Cys Ser
            100                 105

<210> SEQ ID NO 52
<211> LENGTH: 109
<212> TYPE: PRT
<213> ORGANISM: Mus musculus
<220> FEATURE:
<221> NAME/KEY: misc_feature
<222> LOCATION: (1)..(109)
<223> OTHER INFORMATION: Mouse GDF8 Protein ID is O08689; exemplary
      mouse mature GDF8

<400> SEQUENCE: 52

Asp Phe Gly Leu Asp Cys Asp Glu His Ser Thr Glu Ser Arg Cys Cys
1               5                   10                  15

Arg Tyr Pro Leu Thr Val Asp Phe Glu Ala Phe Gly Trp Asp Trp Ile
            20                  25                  30

Ile Ala Pro Lys Arg Tyr Lys Ala Asn Tyr Cys Ser Gly Glu Cys Glu
        35                  40                  45

Phe Val Phe Leu Gln Lys Tyr Pro His Thr His Leu Val His Gln Ala
    50                  55                  60

Asn Pro Arg Gly Ser Ala Gly Pro Cys Cys Thr Pro Thr Lys Met Ser
65                  70                  75                  80

Pro Ile Asn Met Leu Tyr Phe Asn Gly Lys Glu Gln Ile Ile Tyr Gly
                85                  90                  95

Lys Ile Pro Ala Met Val Val Asp Arg Cys Gly Cys Ser
            100                 105

<210> SEQ ID NO 53
<211> LENGTH: 109
<212> TYPE: PRT
<213> ORGANISM: Rattus norvegicus
<220> FEATURE:
<221> NAME/KEY: misc_feature
<222> LOCATION: (1)..(109)
<223> OTHER INFORMATION: Rat GDF11 Protein ID is O35312; exemplary rat
      mature GDF8
```

<400> SEQUENCE: 53

```
Asp Phe Gly Leu Asp Cys Asp Glu His Ser Thr Glu Ser Arg Cys Cys
1               5                   10                  15
Arg Tyr Pro Leu Thr Val Asp Phe Glu Ala Phe Gly Trp Asp Trp Ile
            20                  25                  30
Ile Ala Pro Lys Arg Tyr Lys Ala Asn Tyr Cys Ser Gly Glu Cys Glu
        35                  40                  45
Phe Val Phe Leu Gln Lys Tyr Pro His Thr His Leu Val His Gln Ala
50                  55                  60
Asn Pro Arg Gly Ser Ala Gly Pro Cys Cys Thr Pro Thr Lys Met Ser
65                  70                  75                  80
Pro Ile Asn Met Leu Tyr Phe Asn Gly Lys Glu Gln Ile Ile Tyr Gly
                85                  90                  95
Lys Ile Pro Ala Met Val Val Asp Arg Cys Gly Cys Ser
            100                 105
```

<210> SEQ ID NO 54
<211> LENGTH: 109
<212> TYPE: PRT
<213> ORGANISM: Homo sapiens
<220> FEATURE:
<221> NAME/KEY: misc_feature
<222> LOCATION: (1)..(109)
<223> OTHER INFORMATION: Human GDF11 Protein ID is O95390; exemplary
      human mature GDF11

<400> SEQUENCE: 54

```
Asn Leu Gly Leu Asp Cys Asp Glu His Ser Ser Glu Ser Arg Cys Cys
1               5                   10                  15
Arg Tyr Pro Leu Thr Val Asp Phe Glu Ala Phe Gly Trp Asp Trp Ile
            20                  25                  30
Ile Ala Pro Lys Arg Tyr Lys Ala Asn Tyr Cys Ser Gly Gln Cys Glu
        35                  40                  45
Tyr Met Phe Met Gln Lys Tyr Pro His Thr His Leu Val Gln Gln Ala
50                  55                  60
Asn Pro Arg Gly Ser Ala Gly Pro Cys Cys Thr Pro Thr Lys Met Ser
65                  70                  75                  80
Pro Ile Asn Met Leu Tyr Phe Asn Asp Lys Gln Gln Ile Ile Tyr Gly
                85                  90                  95
Lys Ile Pro Gly Met Val Val Asp Arg Cys Gly Cys Ser
            100                 105
```

<210> SEQ ID NO 55
<211> LENGTH: 109
<212> TYPE: PRT
<213> ORGANISM: Mus musculus
<220> FEATURE:
<221> NAME/KEY: misc_feature
<222> LOCATION: (1)..(109)
<223> OTHER INFORMATION: Mouse GDF11 Protein ID is Q9Z1W4; exemplary
      mouse mature GDF8

<400> SEQUENCE: 55

```
Asn Leu Gly Leu Asp Cys Asp Glu His Ser Ser Glu Ser Arg Cys Cys
1               5                   10                  15
Arg Tyr Pro Leu Thr Val Asp Phe Glu Ala Phe Gly Trp Asp Trp Ile
            20                  25                  30
Ile Ala Pro Lys Arg Tyr Lys Ala Asn Tyr Cys Ser Gly Gln Cys Glu
        35                  40                  45
```

```
Tyr Met Phe Met Gln Lys Tyr Pro His Thr His Leu Val Gln Gln Ala
            50                  55                  60
Asn Pro Arg Gly Ser Ala Gly Pro Cys Cys Thr Pro Thr Lys Met Ser
 65                  70                  75                  80
Pro Ile Asn Met Leu Tyr Phe Asn Asp Lys Gln Gln Ile Ile Tyr Gly
                 85                  90                  95
Lys Ile Pro Gly Met Val Val Asp Arg Cys Gly Cys Ser
                100                 105
```

<210> SEQ ID NO 56
<211> LENGTH: 103
<212> TYPE: PRT
<213> ORGANISM: Rattus norvegicus
<220> FEATURE:
<221> NAME/KEY: misc_feature
<222> LOCATION: (1)..(103)
<223> OTHER INFORMATION: Rat GDF11 Protein ID is Q9Z217; exemplary rat
      mature GDF8

<400> SEQUENCE: 56

```
Asn Leu Gly Leu Asp Cys Asp Glu His Ser Ser Glu Ser Arg Cys Cys
 1               5                  10                  15
Arg Tyr Pro Leu Thr Val Asp Phe Glu Ala Ser Gly Trp Asp Trp Ile
                20                  25                  30
Ile Ala Pro Lys Arg Tyr Lys Ala Asn Tyr Cys Ser Gly Gln Cys Glu
             35                  40                  45
Tyr Met Phe Met Gln Lys Tyr Pro His Thr His Leu Val Gln Gln Ala
            50                  55                  60
Asn Pro Arg Gly Ser Ala Gly Pro Cys Cys Thr Pro Thr Lys Met Ser
 65                  70                  75                  80
Pro Ile Asn Met Leu Tyr Phe Asn Asp Lys Gln Gln Ile Ile Tyr Gly
                 85                  90                  95
Lys Ile Pro Gly Met Val Val
                100
```

<210> SEQ ID NO 57
<211> LENGTH: 407
<212> TYPE: PRT
<213> ORGANISM: Homo sapiens
<220> FEATURE:
<221> NAME/KEY: misc_feature
<222> LOCATION: (1)..(407)
<223> OTHER INFORMATION: GDF11 (Protein ID O95390; amino acids 1 to 407

<400> SEQUENCE: 57

```
Met Val Leu Ala Ala Pro Leu Leu Leu Gly Phe Leu Leu Leu Ala Leu
 1               5                  10                  15
Glu Leu Arg Pro Arg Gly Glu Ala Ala Glu Gly Pro Ala Ala Ala Ala
                20                  25                  30
Ala Ala Ala Ala Ala Ala Ala Gly Val Gly Gly Glu Arg Ser
             35                  40                  45
Ser Arg Pro Ala Pro Ser Val Ala Pro Glu Pro Asp Gly Cys Pro Val
            50                  55                  60
Cys Val Trp Arg Gln His Ser Arg Glu Leu Arg Leu Glu Ser Ile Lys
 65                  70                  75                  80
Ser Gln Ile Leu Ser Lys Leu Arg Leu Lys Glu Ala Pro Asn Ile Ser
                 85                  90                  95
Arg Glu Val Val Lys Gln Leu Leu Pro Lys Ala Pro Pro Leu Gln Gln
                100                 105                 110
```

```
Ile Leu Asp Leu His Asp Phe Gln Gly Asp Ala Leu Gln Pro Glu Asp
            115                 120                 125

Phe Leu Glu Glu Asp Glu Tyr His Ala Thr Thr Glu Thr Val Ile Ser
130                 135                 140

Met Ala Gln Glu Thr Asp Pro Ala Val Gln Thr Asp Gly Ser Pro Leu
145                 150                 155                 160

Cys Cys His Phe His Phe Ser Pro Lys Val Met Phe Thr Lys Val Leu
                165                 170                 175

Lys Ala Gln Leu Trp Val Tyr Leu Arg Pro Val Pro Arg Pro Ala Thr
            180                 185                 190

Val Tyr Leu Gln Ile Leu Arg Leu Lys Pro Leu Thr Gly Glu Gly Thr
        195                 200                 205

Ala Gly Gly Gly Gly Gly Arg Arg His Ile Arg Ile Arg Ser Leu
    210                 215                 220

Lys Ile Glu Leu His Ser Arg Ser Gly His Trp Gln Ser Ile Asp Phe
225                 230                 235                 240

Lys Gln Val Leu His Ser Trp Phe Arg Gln Pro Gln Ser Asn Trp Gly
                245                 250                 255

Ile Glu Ile Asn Ala Phe Asp Pro Ser Gly Thr Asp Leu Ala Val Thr
            260                 265                 270

Ser Leu Gly Pro Gly Ala Glu Gly Leu His Pro Phe Met Glu Leu Arg
        275                 280                 285

Val Leu Glu Asn Thr Lys Arg Ser Arg Arg Asn Leu Gly Leu Asp Cys
    290                 295                 300

Asp Glu His Ser Ser Glu Ser Arg Cys Cys Arg Tyr Pro Leu Thr Val
305                 310                 315                 320

Asp Phe Glu Ala Phe Gly Trp Asp Trp Ile Ile Ala Pro Lys Arg Tyr
                325                 330                 335

Lys Ala Asn Tyr Cys Ser Gly Gln Cys Glu Tyr Met Phe Met Gln Lys
            340                 345                 350

Tyr Pro His Thr His Leu Val Gln Gln Ala Asn Pro Arg Gly Ser Ala
        355                 360                 365

Gly Pro Cys Cys Thr Pro Thr Lys Met Ser Pro Ile Asn Met Leu Tyr
    370                 375                 380

Phe Asn Asp Lys Gln Gln Ile Ile Tyr Gly Lys Ile Pro Gly Met Val
385                 390                 395                 400

Val Asp Arg Cys Gly Cys Ser
                405

<210> SEQ ID NO 58
<211> LENGTH: 375
<212> TYPE: PRT
<213> ORGANISM: Homo sapiens
<220> FEATURE:
<221> NAME/KEY: misc_feature
<222> LOCATION: (1)..(375)
<223> OTHER INFORMATION: myostatin (Protein ID O14793; amino acids 1 to
      375

<400> SEQUENCE: 58

Met Gln Lys Leu Gln Leu Cys Val Tyr Ile Tyr Leu Phe Met Leu Ile
1               5                   10                  15

Val Ala Gly Pro Val Asp Leu Asn Glu Asn Ser Glu Gln Lys Glu Asn
            20                  25                  30

Val Glu Lys Glu Gly Leu Cys Asn Ala Cys Thr Trp Arg Gln Asn Thr
        35                  40                  45
```

```
Lys Ser Ser Arg Ile Glu Ala Ile Lys Ile Gln Ile Leu Ser Lys Leu
 50                  55                  60
Arg Leu Glu Thr Ala Pro Asn Ile Ser Lys Asp Val Ile Arg Gln Leu
 65                  70                  75                  80
Leu Pro Lys Ala Pro Pro Leu Arg Glu Leu Ile Asp Gln Tyr Asp Val
                 85                  90                  95
Gln Arg Asp Asp Ser Ser Asp Gly Ser Leu Glu Asp Asp Tyr His
                100                 105                 110
Ala Thr Thr Glu Thr Ile Ile Thr Met Pro Thr Glu Ser Asp Phe Leu
                115                 120                 125
Met Gln Val Asp Gly Lys Pro Lys Cys Cys Phe Phe Lys Phe Ser Ser
130                 135                 140
Lys Ile Gln Tyr Asn Lys Val Val Lys Ala Gln Leu Trp Ile Tyr Leu
145                 150                 155                 160
Arg Pro Val Glu Thr Pro Thr Thr Val Phe Val Gln Ile Leu Arg Leu
                165                 170                 175
Ile Lys Pro Met Lys Asp Gly Thr Arg Tyr Thr Gly Ile Arg Ser Leu
                180                 185                 190
Lys Leu Asp Met Asn Pro Gly Thr Gly Ile Trp Gln Ser Ile Asp Val
                195                 200                 205
Lys Thr Val Leu Gln Asn Trp Leu Lys Gln Pro Glu Ser Asn Leu Gly
210                 215                 220
Ile Glu Ile Lys Ala Leu Asp Glu Asn Gly His Asp Leu Ala Val Thr
225                 230                 235                 240
Phe Pro Gly Pro Gly Glu Asp Gly Leu Asn Pro Phe Leu Glu Val Lys
                245                 250                 255
Val Thr Asp Thr Pro Lys Arg Ser Arg Arg Asp Phe Gly Leu Asp Cys
                260                 265                 270
Asp Glu His Ser Thr Glu Ser Arg Cys Cys Arg Tyr Pro Leu Thr Val
                275                 280                 285
Asp Phe Glu Ala Phe Gly Trp Asp Trp Ile Ile Ala Pro Lys Arg Tyr
                290                 295                 300
Lys Ala Asn Tyr Cys Ser Gly Glu Cys Glu Phe Val Phe Leu Gln Lys
305                 310                 315                 320
Tyr Pro His Thr His Leu Val His Gln Ala Asn Pro Arg Gly Ser Ala
                325                 330                 335
Gly Pro Cys Cys Thr Pro Thr Lys Met Ser Pro Ile Asn Met Leu Tyr
                340                 345                 350
Phe Asn Gly Lys Glu Gln Ile Ile Tyr Gly Lys Ile Pro Ala Met Val
                355                 360                 365
Val Asp Arg Cys Gly Cys Ser
370                 375

<210> SEQ ID NO 59
<211> LENGTH: 86
<212> TYPE: DNA
<213> ORGANISM: Artificial Sequence
<220> FEATURE:
<223> OTHER INFORMATION: Synthetic: Template 1
<220> FEATURE:
<221> NAME/KEY: modified_base
<222> LOCATION: (1)..(2)
<223> OTHER INFORMATION: Biotin
<220> FEATURE:
<221> NAME/KEY: misc_feature
<222> LOCATION: (31)..(70)
<223> OTHER INFORMATION: n is a, c, g, or t
```

-continued

```
<400> SEQUENCE: 59 aattttttt ggtctcttgt tctgttgttg nnnnnnnnnn nnnnnnnnnn nnnnnnnnnn    60
nnnnnnnnnn cagagaggga gcggag                                        86

<210> SEQ ID NO 60
<211> LENGTH: 25
<212> TYPE: DNA
<213> ORGANISM: Artificial Sequence
<220> FEATURE:
<223> OTHER INFORMATION: Synthetic: Primer 1

<400> SEQUENCE: 60
atatatattc tccgctccct ctctg                                         25

<210> SEQ ID NO 61
<211> LENGTH: 30
<212> TYPE: DNA
<213> ORGANISM: Artificial Sequence
<220> FEATURE:
<223> OTHER INFORMATION: Synthetic: Primer 2
<220> FEATURE:
<221> NAME/KEY: modified_base
<222> LOCATION: (1)..(2)
<223> OTHER INFORMATION: Biotin

<400> SEQUENCE: 61 aattttttt ggtctcttgt tctgttgttg                                     30

<210> SEQ ID NO 62
<211> LENGTH: 50
<212> TYPE: DNA
<213> ORGANISM: Artificial Sequence
<220> FEATURE:
<223> OTHER INFORMATION: Synthetic: 14583-19
<220> FEATURE:
<221> NAME/KEY: misc_feature
<222> LOCATION: (1)..(50)
<223> OTHER INFORMATION: every n is TrpdU

<400> SEQUENCE: 62
ctctgaacnn cnaangncnc nngcannnna ncgcanngan nncnccaaca              50

<210> SEQ ID NO 63
<211> LENGTH: 109
<212> TYPE: PRT
<213> ORGANISM: Homo sapiens
<220> FEATURE:
<221> NAME/KEY: misc_feature
<222> LOCATION: (1)..(109)
<223> OTHER INFORMATION: nonlimiting exemplary mature human GDF8 protein

<400> SEQUENCE: 63
```

Asp Phe Gly Leu Asp Cys Asp Glu His Ser Thr Glu Ser Arg Cys Cys
1               5                   10                  15

Arg Tyr Pro Leu Thr Val Asp Phe Glu Ala Phe Gly Trp Asp Trp Ile
            20                  25                  30

Ile Ala Pro Lys Arg Tyr Lys Ala Asn Tyr Cys Ser Gly Glu Cys Glu
        35                  40                  45

Phe Val Phe Leu Gln Lys Tyr Pro His Thr His Leu Val His Gln Ala
    50                  55                  60

Asn Pro Arg Gly Ser Ala Gly Pro Cys Cys Thr Pro Thr Lys Met Ser
65                  70                  75                  80

```
Pro Ile Asn Met Leu Tyr Phe Asn Gly Lys Glu Gln Ile Ile Tyr Gly
             85                  90                  95

Lys Ile Pro Ala Met Val Val Asp Arg Cys Gly Cys Ser
            100                 105
```

NUCLEIC ACID COMPOUNDS FOR BINDING GROWTH DIFFERENTIATION FACTOR 8

This application is a national phase entry pursuant to 35 U.S.C. § 371 of International Application No. PCT/US2016/016712, filed Feb. 5, 2016, which claims the benefit of priority of US Provisional Application No. 62/113,866, filed Feb. 9, 2015, each of which is incorporated by reference herein in its entirety for any purpose.

FIELD

The present disclosure relates generally to the field of nucleic acids, and more specifically, to aptamers capable of binding to growth differentiation factor 8 (GDF8) protein; compositions comprising a GDF8 binding aptamer; and methods of making and using the same.

BACKGROUND

Growth differentiation factor 8 (GDF8) or myostatin belongs to the transforming growth factor beta superfamily that controls anterior-posterior patterning during development by regulating the expression of Hox genes. GDF8 is a negative regulator of muscle growth, and has been shown to play a role in the regulation of cardiacmyocyte proliferation.

GDF8 is closely related to GDF11, which is a negative regulator of muscle growth. Like GDF8, GDF11 is involved in the regulation of cardiacmyocyte proliferation. The similarities between myostatin and GDF11 imply a likelihood that the same regulatory mechanisms are used to control tissue size during both muscular and neural development. Mechanistically, the actions of myostatin are likely regulated by WFIKKN2, a large extracellular multidomain protein consisting of follistatin, immunoglobulin, protease inhibitor, and NTR domains. WFIKKN2 has been found to inhibit the biological activities of myostatin and has a high affinity for GDF11.

Both GDF8 (myostatin) and GDF11 play important roles in the course of development, and in the regulation of cell growth and differentiation in adult tissues. The ability to localize and/or measure these two proteins is important to further understand and distinguish their contributions in development and adult tissues (e.g., cardiac and skeletal muscle). However, due to their homology it is difficult to distinguish the presence and/or levels of these proteins with current protein binding reagents (e.g., antibodies). Thus, there is a need for protein binding reagents that are capable of distinguishing the GDF8 and GDF11. The present disclosure meets such needs by providing aptamers having binding specificity to a GDF8 protein.

SUMMARY

The present disclosure describes aptamers capable of binding to growth differentiation factor 8 (GDF8; myostatin) protein. In some embodiment, aptamers that bind GDF8 with an equilibrium binding constant ($K_d$) of less than 100 nM are provided. In another aspect, the $K_d$ is from about 0.1 nM to about 100 nM (or from about 0.1 nM to about 50 nM, or from about 0.1 nM to about 10 nM, or from about 0.5 nM to about 10 nM, or from about 0.5 nM to about 5 nM).

In some embodiments, an aptamer that binds GDF8 with an affinity of less than 10 nM is provided. In some embodiments, the aptamer binds GDF8 with an affinity of less than 10 nM, and, under the same conditions, the aptamer binds GDF11 with an affinity that is at least 10-fold weaker than the affinity for GDF8. In some embodiments, the aptamer does not bind GDF11. In some embodiments, the aptamer binds GDF11 with an affinity that is at least 20-fold weaker, or at least 30-fold weaker, or at least 50-fold weaker than the affinity for GDF8. In some embodiments, the aptamer binds GDF11 with an affinity greater than 50 nM, or greater than 100 nM, or greater than 150 nM, or greater than 200 nM, or greater than 250 nM, or greater than 300 nM. In some embodiments, the aptamer binds GDF8 with an affinity of less than 8 nM, or less than 7 nM, or less than 6 nM, or less than 5 nM, or less than 4 nM, or less than 3 nM, or less than 2 nM, or less than 1 nM. In some embodiments, affinity is determined using a binding assay comprising a polyanionic inhibitor. In some embodiments, the polyanionic inhibitor is selected from dextran sulfate, heparin, Z-block, poly-dI/dC, sonicated or sheared salmon sperm DNA, calf thymus DNA, and dNTPs.

In some embodiments, the aptamer comprises the sequence 5' GWWR$^1$C$_n$R$^2$ZG$_n$GWC$_n$X$^2$CW$_n$WWX$^1$A$_n$ R$^1$ C$_n$X$^1$KW$_n$AGX$^2{}_n$WCX$^1$ZD-3' (SEQ ID NO: 1), wherein:
each W is independently, and for each occurrence, a C-5 modified pyrimidine;
X$^1$ and X$^2$ are each independently selected from W and C;
R$^1$ and R$^2$ are each independently selected from G and A;
each Z is independently selected from A and W;
K is selected from G and W;
D is selected from G, A, and W; and
each n is independently selected from 0 and 1.

In some embodiments, the aptamer comprises the sequence
5'-WGWWAGZGWX$^2$CWWX$^1$AWGAGWCWAD-3'
(SEQ ID NO: 3), wherein:
each W is independently, and for each occurrence, a C-5 modified pyrimidine;
X$^1$ and X$^2$ are each independently selected from W and C;
Z is selected from A and W; and
D is selected from G, A, and W.

In some embodiments, the aptamer comprises the sequence 5'-GWWAGAGWCCWWWAWGAGWCWAG-3' (SEQ ID NO: 4), wherein each W is independently, and for each occurrence, a C-5 modified pyrimidine.

In some embodiments, an aptamer that binds GDF8 is provided, wherein the aptamer comprises the sequence 5'-GWWR$^1$C$_n$R$^2$ZG$_n$GWC$_n$X$^2$CW$_n$WWX$^1$A$_n$R$^1$C$_n$X$^1$KW$_n$ AGX$^2{}_n$WCX$^1$ZD-3' (SEQ ID NO: 1), wherein:
each W is independently, and for each occurrence, a C-5 modified pyrimidine;
X$^1$ and X$^2$ are each independently selected from W and C;
R$^1$ and R$^2$ are each independently selected from G and A;
each Z is independently selected from A and W;
K is selected from G and W;
D is selected from G, A, and W; and
each n is independently selected from 0 and 1.

In some embodiments, an aptamer that binds GDF8 is provided, wherein the aptamer comprises the sequence 5'-GWWR$^1$R$^2$ZGWC$_n$X$^2$CW$_n$WWX$^1$A$_n$R$^1$C$_n$X$^1$KAGWX CX$^1$ZD-3' (SEQ ID NO: 49), wherein:
each W is independently, and for each occurrence, a C-5 modified pyrimidine;
X$^1$ and X$^2$ are each independently selected from W and C;
R$^1$ and R$^2$ are each independently selected from G and A;
each Z is independently selected from A and W;
K is selected from G and W;
D is selected from G, A, and W; and
each n is independently selected from 0 and 1.

In some embodiments, an aptamer that binds GDF8 is provided, wherein the aptamer comprises the sequence 5'-WGWWAGZGWX$^2$CWWX$^1$AWGAGWCWAD-3' (SEQ ID NO: 3), wherein:

each W is independently, and for each occurrence, a C-5 modified pyrimidine;
X$^1$ and X$^2$ are each independently selected from W and C;
Z is selected from A and W; and
D is selected from G, A, and W.

In some embodiments of the sequences above, at least one R$^1$ is A. In some embodiments of the sequences above, each R$^1$ is A. In some embodiments of the sequences above, at least one R$^2$ is G. In some embodiments of the sequences above, each R$^2$ is G. In some embodiments of the sequences above, K is G. In some embodiments of the sequences above, at least 1, at least 2, at least 3, at least 4, at least 5, or at least 6, at least 7 or 8 n are 0. In some embodiments of the sequences above, each n is 0. In some embodiments of the sequences above, 1, 2, or 3 n are 1, and the rest of the n's are 0.

In some embodiments of the sequences above, at least one X$^1$ is W. In some embodiments of the sequences above, each X$^1$ is W. In some embodiments of the sequences above, at least one X$^2$ is C. In some embodiments of the sequences above, each X$^2$ is C.

In some embodiments, an aptamer that binds GDF8 is provided, wherein the aptamer comprises the sequence 5'-GWWAGAGWCCWWWAWGAGWCWAG-3' (SEQ ID NO: 4), wherein each W is independently, and for each occurrence, a C-5 modified pyrimidine.

In some embodiments of the sequences above, each W is independently, and for each occurrence, selected from:
5-(N-benzylcarboxyamide)-2'-deoxyuridine (BndU),
5-(N-benzylcarboxyamide)-2'-O-methyluridine,
5-(N-benzylcarboxyamide)-2'-fluorouridine,
5-(N-phenethylcarboxyamide)-2'-deoxyuridine (PEdU),
5-(N-thiophenylmethylcarboxyamide)-2'-deoxyuridine (ThdU),
5-(N-isobutylcarboxyamide)-2'-deoxyuridine (iBudU),
5-(N-tyrosylcarboxyamide)-2'-deoxyuridine (TyrdU),
5-(N-3,4-methylenedioxybenzylcarboxyamide)-2'-deoxyuridine (MBndU),
5-(N-4-fluorobenzylcarboxyamide)-2'-deoxyuridine (FBndU),
5-(N-3-phenylpropylcarboxyamide)-2'-deoxyuridine (PPdU),
5-(N-imidizolylethylcarboxyamide)-2'-deoxyuridine (ImdU),
5-(N-isobutylcarboxyamide)-2'-O-methyluridine,
5-(N-isobutylcarboxyamide)-2'-fluorouridine,
5-(N-tryptaminocarboxyamide)-2'-deoxyuridine (TrpdU),
5-(N—R-threoninylcarboxyamide)-2'-deoxyuridine (ThrdU),
5-(N-tryptaminocarboxyamide)-2'-O-methyluridine,
5-(N-tryptaminocarboxyamide)-2'-fluorouridine,
5-(N-[1-(3-trimethylammonium) propyl]carboxyamide)-2'-deoxyuridine chloride,
5-(N-naphthylmethylcarboxyamide)-2'-deoxyuridine (NapdU),
5-(N-naphthylmethylcarboxyamide)-2'-O-methyluridine,
5-(N-naphthylmethylcarboxyamide)-2'-fluorouridine,
5-(N-[1-(2,3-dihydroxypropyl)]carboxyamide)-2'-deoxyuridine),
5-(N-2-naphthylmethylcarboxyamide)-2'-deoxyuridine (2NapdU),
5-(N-2-naphthylmethylcarboxyamide)-2'-O-methyluridine,
5-(N-2-naphthylmethylcarboxyamide)-2'-fluorouridine,
5-(N-1-naphthylethylcarboxyamide)-2'-deoxyuridine (NEdU),
5-(N-1-naphthylethylcarboxyamide)-2'-O-methyluridine,
5-(N-1-naphthylethylcarboxyamide)-2'-fluorouridine,
5-(N-2-naphthylethylcarboxyamide)-2'-deoxyuridine (2NEdU),
5-(N-2-naphthylethylcarboxyamide)-2'-O-methyluridine,
5-(N-2-naphthylethylcarboxyamide)-2'-fluorouridine,
5-(N-3-benzofuranylethylcarboxyamide)-2'-deoxyuridine (BFdU),
5-(N-3-benzofuranylethylcarboxyamide)-2'-O-methyluridine,
5-(N-3-benzofuranylethylcarboxyamide)-2'-fluorouridine,
5-(N-3-benzothiophenylethylcarboxyamide)-2'-deoxyuridine (BTdU),
5-(N-3-benzothiophenylethylcarboxyamide)-2'-O-methyluridine, and
5-(N-3-benzothiophenylethylcarboxyamide)-2'-fluorouridine.

In some embodiments, each W is independently, and for each occurrence, selected from:
5-(N-tryptaminocarboxyamide)-2'-deoxyuridine (TrpdU),
5-(N-tryptaminocarboxyamide)-2'-O-methyluridine,
5-(N-tryptaminocarboxyamide)-2'-fluorouridine,
5-(N-1-naphthylmethylcarboxyamide)-2'-deoxyuridine (NapdU),
5-(N-1-naphthylmethylcarboxyamide)-2'-O-methyluridine,
5-(N-1-naphthylmethylcarboxyamide)-2'-fluorouridine,
5-(N-2-naphthylmethylcarboxyamide)-2'-deoxyuridine (2NapdU),
5-(N-2-naphthylmethylcarboxyamide)-2'-O-methyluridine,
5-(N-2-naphthylmethylcarboxyamide)-2'-fluorouridine,
5-(N-1-naphthylethylcarboxyamide)-2'-deoxyuridine (NEdU),
5-(N-1-naphthylethylcarboxyamide)-2'-O-methyluridine,
5-(N-1-naphthylethylcarboxyamide)-2'-fluorouridine,
5-(N-2-naphthylethylcarboxyamide)-2'-deoxyuridine (2NEdU),
5-(N-2-naphthylethylcarboxyamide)-2'-O-methyluridine,
5-(N-2-naphthylethylcarboxyamide)-2'-fluorouridine,
5-(N-3-benzofuranylethylcarboxyamide)-2'-deoxyuridine (BFdU),
5-(N-3-benzofuranylethylcarboxyamide)-2'-O-methyluridine,
5-(N-3-benzofuranylethylcarboxyamide)-2'-fluorouridine,
5-(N-3-benzothiophenylethylcarboxyamide)-2'-deoxyuridine (BTdU),
5-(N-3-benzothiophenylethylcarboxyamide)-2'-O-methyluridine, and
5-(N-3-benzothiophenylethylcarboxyamide)-2'-fluorouridine.

In some embodiments, at least 1, at least 2, at least 3, at least 4, at least 5, or at least 6 W are each independently selected from 5-(N-tryptaminocarboxyamide)-2'-deoxyuridine (TrpdU), 5-(N-tryptaminocarboxyamide)-2'-O-methyluridine, and 5-(N-tryptaminocarboxyamide)-2'-fluorouridine. In some embodiments, each W is independently selected from 5-(N-tryptaminocarboxyamide)-2'-deoxyuridine (TrpdU), 5-(N-tryptaminocarboxyamide)-2'-O-methyluridine, and 5-(N-tryptaminocarboxyamide)-2'-fluorouridine.

In some embodiments, the aptamer comprises a sequence selected from SEQ ID NOs: 5 to 48. In some embodiments, the aptamer comprises a sequence selected from SEQ ID NOs: 5 to 19, 26 to 28, 30 to 32, and 34 to 48.

In any of the embodiments described herein, the aptamer may consist of 18 to 200 nucleotides, or 18 to 150 nucleotides, or 18 to 100 nucleotides, or 18 to 75 nucleotides, or 18 to 50 nucleotides, or 20 to 150 nucleotides, or 20 to 100 nucleotides, or 20 to 75 nucleotides, or 20 to 50 nucleotides, or 23 to 200 nucleotides, or 23 to 150 nucleotides, or 23 to 100 nucleotides, or 23 to 75 nucleotides, or 23 to 50 nucleotides, wherein each nucleotide may, independently, be a modified or unmodified nucleotide. In any of the embodiments described herein, the aptamer may comprise a detectable label.

In some embodiments, GDF8 is human, mouse, or rat GDF8 and GDF11 is human, mouse, or rat GDF11. In some embodiments, GDF8 is mature human GDF8 comprising the sequence of SEQ ID NO: 63 and GDF11 is mature human GDF11 comprising the sequence of SEQ ID NO: 50.

In some embodiments, a method of detecting GDF8 in a sample is provided, comprising contacting proteins from the sample with an aptamer described herein. In some embodiments, the aptamer binds GDF11 with an affinity that is at least 10-fold weaker than the affinity for GDF8. In some embodiments, the aptamer does not bind GDF11.

In some embodiments, a method of determining whether a sample comprises GDF8, comprising contacting proteins from the sample with an aptamer described herein. In some embodiments, the sample comprises GDF11. In some embodiments, the method comprises contacting the sample with the aptamer under stringent conditions. In some embodiments, the stringent conditions comprise a polyanionic inhibitor. In some embodiments, the polyanionic inhibitor is selected from dextran sulfate, heparin, Z-block, poly-dI/dC, sonicated or sheared salmon sperm DNA, calf thymus DNA, and dNTPs.

In some embodiments, the sample is a sample from a human. In some embodiments, the sample is selected from blood, serum, plasma, saliva, urine, and a tissue sample. In some embodiments, the tissue sample is selected from heart muscle tissue, skeletal muscle tissue, pancreatic tissue, cartilage tissue and neural tissue.

In some embodiments, the proteins have been separated from at least one other component of the sample. In some embodiments, the proteins have not been separated from other components of the sample.

In some embodiments, compositions are provided comprising an aptamer described herein and proteins from a sample. In some embodiments, the sample comprises GDF11. In some embodiments, the composition comprises a polyanionic inhibitor. In some embodiments, the polyanionic inhibitor is selected from dextran sulfate, heparin, Z-block, poly-dI/dC, sonicated or sheared salmon sperm DNA, calf thymus DNA, and dNTPs. In some embodiments, the sample is a sample from a human. In some embodiments, the sample is selected from blood, serum, plasma, saliva, urine, and a tissue sample. In some embodiments, the tissue sample is selected from heart muscle tissue, skeletal muscle tissue, pancreatic tissue, cartilage tissue and neural tissue. In some embodiments, the proteins have been separated from at least one other component of the sample. In some embodiments, the proteins have not been separated from other components of the sample.

In another aspect, the aptamer is at least 25 nucleotides in length. In another aspect, the aptamer is at least 30 nucleotides in length. In another aspect, the aptamer is at least 40 nucleotides in length. In another aspect, the aptamer is from about 40 to about 100 nucleotides in length (or from 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 nucleotides in length).

The present disclosure further provides a composition comprising an aptamer and a GDF8 protein, wherein the aptamer and the GDF8 protein are bound by a non-covalent interaction.

The foregoing and other objects, features, and advantages of the invention will become more apparent from the following detailed description, which proceeds with reference to the accompanying figures.

BRIEF DESCRIPTION OF THE DRAWINGS

FIG. 3 shows a truncation analysis of aptamer clone 14583-49_3 (50-mer sequence) and the binding affinity of each sequence for GDF8 in the presence of a polyanionic inhibitor (Z-block).

DETAILED DESCRIPTION

I. Terms and Methods

Figure 1:
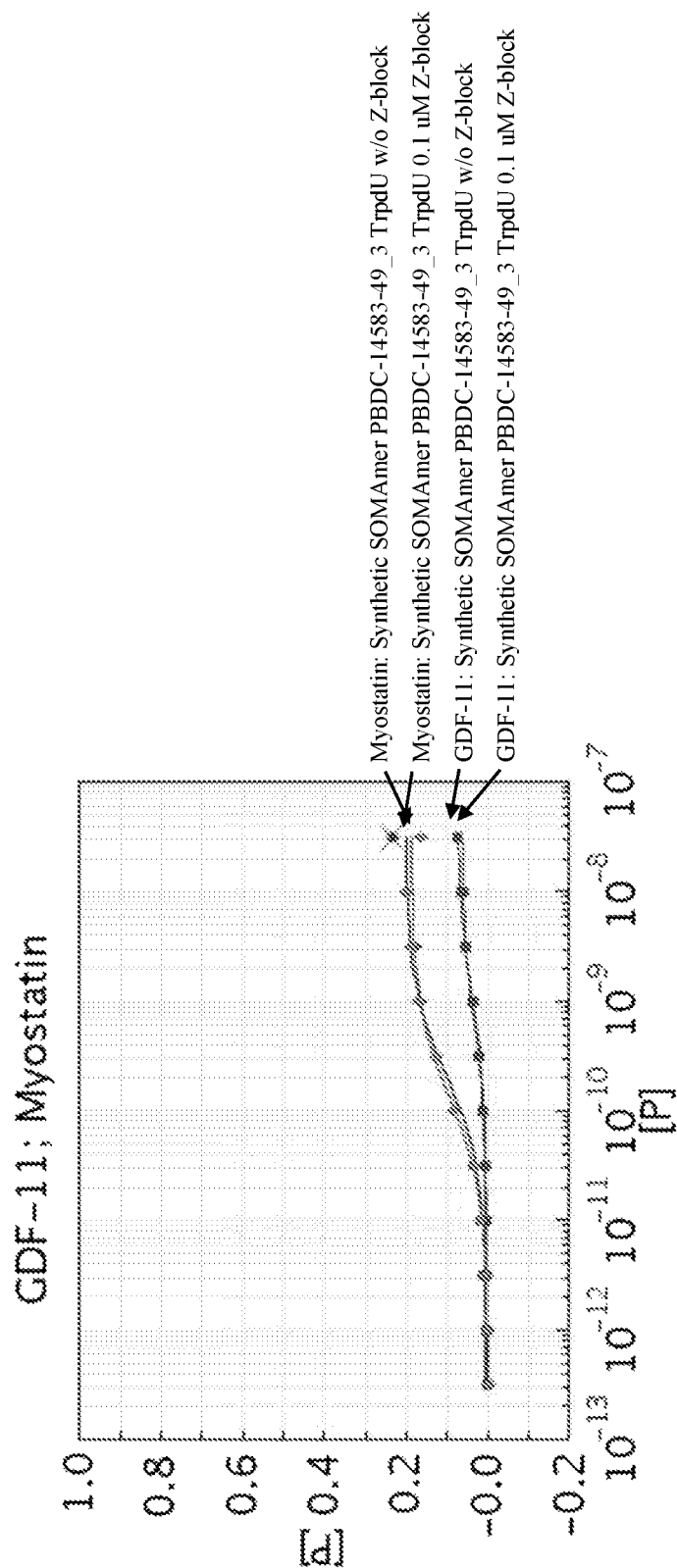
FIG. 1 shows a comparison of the binding affinities of aptamer clone 14583-49_3 for human GDF8 protein and human GDF11 protein in the presence or absence of a polyanionic inhibitor (Z-block). The x-axis shows the concentrations for the respective proteins and the y-axis shows the percent of the aptamer bound to the protein (1.0 is 100%).

While the invention will be described in conjunction with certain representative embodiments, it will be understood that the invention is defined by the claims, and is not limited to those embodiments.

One skilled in the art will recognize many methods and materials similar or equivalent to those described herein may be used in the practice of the present invention. The present invention is in no way limited to the methods and materials described.

Unless defined otherwise, technical and scientific terms used herein have the meaning commonly understood by one of ordinary skill in the art to which this invention belongs. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8). Although any methods, devices, and materials similar or equivalent to those described herein can be used in the practice of the invention, certain methods, devices, and materials are described herein.

All publications, published patent documents, and patent applications cited herein are hereby incorporated by reference to the same extent as though each individual publication, published patent document, or patent application was specifically and individually indicated as being incorporated by reference.

As used in this application, including the appended claims, the singular forms "a," "an," and "the" include the plural, unless the context clearly dictates otherwise, and may be used interchangeably with "at least one" and "one or more." Thus, reference to "an aptamer" includes mixtures of aptamers, reference to "a probe" includes mixtures of probes, and the like.

As used herein, the terms "comprises," "comprising," "includes," "including," "contains," "containing," and any variations thereof, are intended to cover a non-exclusive inclusion, such that a process, method, product-by-process, or composition of matter that comprises, includes, or contains an element or list of elements may include other elements not expressly listed.

It is further to be understood that all base sizes or amino acid sizes, and all molecular weight or molecular mass values, given for nucleic acids or polypeptides are approximate, and are provided for description.

In order to facilitate review of the various embodiments of the disclosure, the following explanations of specific terms are provided:

Aptamer: As used herein, an "aptamer" refers to a nucleic acid that has a specific binding affinity for a target molecule. It is recognized that affinity interactions are a matter of degree; however, in this context, the "specific binding affinity" of an aptamer for its target means that the aptamer binds to its target generally with a much higher degree of affinity than it binds to other components in a test sample. An "aptamer" is a set of copies of one type or species of nucleic acid molecule that has a particular nucleotide sequence. An aptamer can include any suitable number of nucleotides, including any number of chemically modified nucleotides. "Aptamers" refers to more than one such set of molecules. Different aptamers can have either the same or different numbers of nucleotides. Aptamers can be DNA or RNA or chemically modified nucleic acids and can be single stranded, double stranded, or contain double stranded regions, and can include higher ordered structures. An aptamer can also be a photoaptamer, where a photoreactive or chemically reactive functional group is included in the aptamer to allow it to be covalently linked to its corresponding target. Any of the aptamer methods disclosed herein can include the use of two or more aptamers that specifically bind the same target molecule. As further described below, an aptamer may include a tag. If an aptamer includes a tag, all copies of the aptamer need not have the same tag. Moreover, if different aptamers each include a tag, these different aptamers can have either the same tag or a different tag.

An aptamer can be identified using any known method, including the SELEX process. Once identified, an aptamer can be prepared or synthesized in accordance with any known method, including chemical synthetic methods and enzymatic synthetic methods.

GDF8 Aptamer: GDF8 aptamer, as used herein, refers to an aptamer that is capable of binding to a mature GDF8 protein. A nonlimiting exemplary mature human GDF8 protein is shown below (amino acids 267 to 375 of UniProtKB/Swiss-Prot: O14793):
DFGL DCDEHSTESR CCRYPLTVDF EAFGWDWIIA PKRYKANYCS GECEFVFLQK YPHTHLVHQA NPRG-SAGPCC TPTKMSPINM LYFNGKEQII YGKIPAMVVD RCGCS (SEQ ID NO: 63).

In some embodiments, a GDF8 aptamer binds GDF11 with an affinity that is at least 10-fold weaker than the affinity for GDF8. In some embodiments, a GDF8 aptamer does not bind GDF11. A nonlimiting exemplary mature human GDF11 protein is shown below (amino acids 299 to 407 of UniProtKB/Swiss-Prot: O95390):
NL GLDCDEHSSE SRCCRYPLTV DFEAFGWDWI IAP-KRYKANY CSGQCEYMFM QKYPHTHLVQ QANPRG-SAGP CCTPTKMSPI NMLYFNDKQQ IIYGKIPGMV VDRCGCS (SEQ ID NO: 50).

Inhibit: The term inhibit, as used herein, means to prevent or reduce the expression of a peptide or a polypeptide to an extent that the peptide or polypeptide no longer has measurable activity or bioactivity; or to reduce the stability and/or reduce or prevent the activity of a peptide or a polypeptide to an extent that the peptide or polypeptide no longer has measurable activity or bioactivity. As described herein, the protein that may be inhibited is GDF8.

Nucleic acid: As used herein, "nucleic acid," "oligonucleotide," and "polynucleotide" are used interchangeably to refer to a polymer of nucleotides and include DNA, RNA, DNA/RNA hybrids and modifications of these kinds of nucleic acids, oligonucleotides and polynucleotides, wherein the attachment of various entities or moieties to the nucleotide units at any position are included. The terms "polynucleotide," "oligonucleotide," and "nucleic acid" include double- or single-stranded molecules as well as triple-helical molecules. Nucleic acid, oligonucleotide, and polynucleotide are broader terms than the term aptamer and, thus, the terms nucleic acid, oligonucleotide, and polynucleotide include polymers of nucleotides that are aptamers but the terms nucleic acid, oligonucleotide, and polynucleotide are not limited to aptamers.

Modified: As used herein, the terms "modify", "modified", "modification", and any variations thereof, when used in reference to an oligonucleotide, means that at least one of the four constituent nucleotide bases (i.e., A, G, T/U, and C) of the oligonucleotide is an analog or ester of a naturally occurring nucleotide. In some embodiments, the modified nucleotide confers nuclease resistance to the oligonucleotide. In some embodiments, the modified nucleotides lead to predominantly hydrophobic interactions of aptamers with protein targets resulting in high binding efficiency and stable co-crystal complexes. A pyrimidine with a substitution at the C-5 position is an example of a modified nucleotide. Modifications can include backbone modifications, methylations, unusual base-pairing combinations such as the isobases isocytidine and isoguanidine, and the like. Modifications can also include 3' and 5' modifications, such as capping. Other modifications can include substitution of one or more of the naturally occurring nucleotides with an analog, internucleotide modifications such as, for example, those with uncharged linkages (e.g., methyl phosphonates, phosphotriesters, phosphoamidates, carbamates, etc.) and those with charged linkages (e.g., phosphorothioates, phosphorodithioates, etc.), those with intercalators (e.g., acridine, psoralen, etc.), those containing chelators (e.g., metals, radioactive metals, boron, oxidative metals, etc.), those containing alkylators, and those with modified linkages (e.g., alpha anomeric nucleic acids, etc.). Further, any of the hydroxyl groups ordinarily present on the sugar of a nucleotide may be replaced by a phosphonate group or a phosphate group; protected by standard protecting groups; or activated to prepare additional linkages to additional nucleotides or to a solid support. The 5' and 3' terminal OH groups can be phosphorylated or substituted with amines, organic capping group moieties of from about 1 to about 20 carbon atoms, polyethylene glycol (PEG) polymers, in some embodiments, ranging from about 10 to about 80 kDa, PEG polymers, in some embodiments, ranging from about 20 to about 60 kDa, or other hydrophilic or hydrophobic biological or synthetic polymers. In one embodiment, modifications are of the C-5 position of pyrimidines. These modifications can be produced through an amide linkage directly at the C-5 position or by other types of linkages.

Polynucleotides can also contain analogous forms of ribose or deoxyribose sugars that are generally known in the art, including 2'-O-methyl-, 2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside. As noted above, one or more phosphodiester linkages may be replaced by alternative linking groups. These alternative linking groups include embodiments wherein phosphate is replaced by P(O)S ("thioate"), P(S)S ("dithioate"), (O)NR2 ("amidate"), P(O)R, P(O)OR', CO or CH2 ("formacetal"), in which each R or R' is independently H or substituted or unsubstituted alkyl (1-20 C) optionally containing an ether (—O—) linkage, aryl, alkenyl, cycloalky, cycloalkenyl or araldyl. Not all linkages in a polynucleotide need be identical. Substitution of analogous forms of sugars, purines, and pyrimidines can be advantageous in designing a final product, as can alternative backbone structures like a polyamide backbone, for example.

Nuclease: As used herein, the term "nuclease" refers to an enzyme capable of cleaving the phosphodiester bond between nucleotide subunits of an oligonucleotide. As used herein, the term "endonuclease" refers to an enzyme that cleaves phosphodiester bond(s) at a site internal to the oligonucleotide. As used herein, the term "exonuclease" refers to an enzyme which cleaves phosphodiester bond(s) linking the end nucleotides of an oligonucleotide. Biological fluids typically contain a mixture of both endonucleases and exonucleases.

As used herein, the terms "nuclease resistant" and "nuclease resistance" refers to the reduced ability of an oligonucleotide to serve as a substrate for an endo- or exonuclease, such that, when contacted with such an enzyme, the oligonucleotide is either not degraded or is degraded more slowly than an oligonucleotide composed of unmodified nucleotides.

C-5 Modified Pyrimidine: As used herein, the term "C-5 modified pyrimidine" refers to a pyrimidine with a modification at the C-5 position including, but not limited to, those moieties illustrated in FIG. 20 and FIG. 24. Examples of a C-5 modified pyrimidine include those described in U.S. Pat. Nos. 5,719,273 and 5,945,527. Examples of a C-5 modification include substitution of deoxyuridine at the C-5 position with a substituent independently selected from: benzylcarboxyamide (alternatively benzylaminocarbonyl) (Bn), naphthylmethylcarboxyamide (alternatively naphthylmethylaminocarbonyl) (Nap), tryptaminocarboxyamide (alternatively tryptaminocarbonyl) (Trp), phenethylcarboxyamide (alternatively phenethylamino carbonyl) (Pe), thiophenylmethylcarboxyamide (alternatively thiophenylmethylaminocarbonyl) (Th) and isobutylcarboxyamide (alternatively isobutylaminocarbonyl) (iBu) as illustrated immediately below.

Chemical modifications of a C-5 modified pyrimidine can also be combined with, singly or in any combination, 2'-position sugar modifications, modifications at exocyclic amines, and substitution of 4-thiouridine and the like.

Representative C-5 modified pyrimidines include: 5-(N-benzylcarboxyamide)-2'-deoxyuridine (BndU), 5-(N-benzylcarboxyamide)-2'-O-methyluridine, 5-(N-benzylcarboxyamide)-2'-fluorouridine, 5-(N-isobutylcarboxyamide)-2'-deoxyuridine (iBudU), 5-(N-isobutylcarboxyamide)-2'-O-methyluridine, 5-(N-phenethylcarboxyamide)-2'-deoxyuridine (PedU), 5-(N-thiophenylmethylcarboxyamide)-2'-deoxyuridine (ThdU), 5-(N-isobutylcarboxyamide)-2'-fluorouridine, 5-(N-tryptaminocarboxyamide)-2'-deoxyuridine (TrpdU), 5-(N-tryptaminocarboxyamide)-2'-O-methyluridine, 5-(N-tryptaminocarboxyamide)-2'-fluorouridine, 5-(N-[1-(3-trimethylammonium) propyl]carboxyamide)-2'-deoxyuridine chloride, 5-(N-naphthylmethylcarboxyamide)-2'-deoxyuridine (NapdU), 5-(N-naphthylmethylcarboxyamide)-2'-O-methyluridine, 5-(N-naphthylmethylcarboxyamide)-2'-fluorouridine or 5-(N-[1-(2,3-dihydroxypropyl)]carboxyamide)-2'-deoxyuridine).

Nucleotides can be modified either before or after synthesis of an oligonucleotide. A sequence of nucleotides in an oligonucleotide may be interrupted by one or more non-nucleotide components. A modified oligonucleotide may be further modified after polymerization, such as, for example, by conjugation with any suitable labeling component.

As used herein, the term "at least one pyrimidine," when referring to modifications of a nucleic acid, refers to one, several, or all pyrimidines in the nucleic acid, indicating that any or all occurrences of any or all of C, T, or U in a nucleic acid may be modified or not.

Modulate: The term modulate, as used herein, means to alter the expression level of a peptide, protein or polypeptide by increasing or decreasing its expression level relative to a reference expression level, and/or alter the stability and/or activity of a peptide, protein or polypeptide by increasing or decreasing its stability and/or activity level relative to a reference stability and/or activity level.

Pharmaceutically Acceptable: Pharmaceutically acceptable, as used herein, means approved by a regulatory agency of a federal or a state government or listed in the U.S. Pharmacopoeia or other generally recognized pharmacopoeia for use in animals and, more particularly, in humans.

Pharmaceutically Acceptable Salt: Pharmaceutically acceptable salt or salt of a compound (e.g., aptamer), as used herein, refers to a product that contains an ionic bond and is typically produced by reacting the compound with either an acid or a base, suitable for administering to an individual. A pharmaceutically acceptable salt can include, but is not limited to, acid addition salts including hydrochlorides, hydrobromides, phosphates, sulphates, hydrogen sulphates, alkylsulphonates, arylsulphonates, arylalkylsulfonates, acetates, benzoates, citrates, maleates, fumarates, succinates, lactates, and tartrates; alkali metal cations such as Li, Na, K, alkali earth metal salts such as Mg or Ca, or organic amine salts.

Pharmaceutical Composition: Pharmaceutical composition, as used herein, refers to formulation comprising a GDF8 aptamer in a form suitable for administration to an individual. A pharmaceutical composition is typically formulated to be compatible with its intended route of administration. Examples of routes of administration include, but are not limited to, oral and parenteral, e.g., intravenous, intradermal, subcutaneous, inhalation, topical, transdermal, transmucosal, and rectal administration.

SELEX: The terms "SELEX" and "SELEX process" are used interchangeably herein to refer generally to a combination of (1) the selection of aptamers that interact with a target molecule in a desirable manner, for example binding with high affinity to a protein, with (2) the amplification of those selected nucleic acids. The SELEX process can be used to identify aptamers with high affinity to a specific target or biomarker.

Sequence Identity: Sequence identity, as used herein, in the context of two or more nucleic acid sequences is a function of the number of identical nucleotide positions shared by the sequences (i.e., % identity=number of identical positions/total number of positions×100), taking into account the number of gaps, and the length of each gap that needs to be introduced to optimize alignment of two or more sequences. The comparison of sequences and determination of percent identity between two or more sequences can be accomplished using a mathematical algorithm, such as BLAST and Gapped BLAST programs at their default parameters (e.g., Altschul et al., *J. Mol. Biol.* 215:403, 1990; see also BLASTN at www.ncbi.nlm.nih.gov/BLAST). For sequence comparisons, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters. Optimal alignment of sequences for comparison can be conducted, e.g., by the local homology algorithm of Smith and Waterman, Adv. Appl. Math., 2:482, 1981, by the homology alignment algorithm of Needleman and Wunsch, J. Mol. Biol., 48:443, 1970, by the search for similarity method of Pearson and Lipman, Proc. Nat'l. Acad. Sci. USA 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Ausubel, F. M. et al., Current Protocols in Molecular Biology, pub. by Greene Publishing Assoc. and Wiley-Interscience (1987)). As used herein, when describing the percent identity of a nucleic acid, such as a GDF8 aptamer, the sequence of which is at least, for example, about 95% identical to a reference nucleotide sequence, it is intended that the nucleic acid sequence is identical to the reference sequence except that the nucleic acid sequence may include up to five point mutations per each 100 nucleotides of the reference nucleic acid sequence. In other words, to obtain a desired nucleic acid sequence, the sequence of which is at least about 95% identical to a reference nucleic acid sequence, up to 5% of the nucleotides in the reference sequence may be deleted or substituted with another nucleotide, or some number of nucleotides up to 5% of the total number of nucleotides in the reference sequence may be inserted into the reference sequence (referred to herein as an insertion). These mutations of the reference sequence to generate the desired sequence may occur at the 5' or 3' terminal positions of the reference nucleotide sequence or anywhere between those terminal positions, interspersed either individually among nucleotides in the reference sequence or in one or more contiguous groups within the reference sequence.

SOMAmer: The term SOMAmer, as used herein, refers to an aptamer having improved off-rate characteristics. SOMAmers are alternatively referred to as Slow Off-Rate Modified Aptamers, and may be selected via the improved SELEX methods described in U.S. Publication No. 20090004667, entitled "Method for Generating Aptamers with Improved Off-Rates", which is incorporated by reference in its entirety. In some embodiments, a slow off-rate aptamer (including an aptamers comprising at least one nucleotide with a hydrophobic modification) has an off-rate (t½) of ≥2 minutes, ≥4 minutes, ≥5 minutes, ≥8 minutes, ≥10 minutes, ≥15 minutes ≥30 minutes, ≥60 minutes, ≥90 minutes, ≥120 minutes, ≥150 minutes, ≥180 minutes, ≥210 minutes, or ≥240 minutes.

Target Molecule: "Target", "target molecule", and "analyte" are used interchangeably herein to refer to any molecule of interest that may be present in a sample. The term includes any minor variation of a particular molecule, such as, in the case of a protein, for example, minor variations in amino acid sequence, disulfide bond formation, glycosylation, lipidation, acetylation, phosphorylation, or any other manipulation or modification, such as conjugation with a labeling component, which does not substantially alter the identity of the molecule. A "target molecule", "target", or "analyte" refers to a set of copies of one type or species of molecule or multi-molecular structure. "Target molecules", "targets", and "analytes" refer to more than one type or species of molecule or multi-molecular structure. Exemplary target molecules include proteins, polypeptides, nucleic acids, carbohydrates, lipids, polysaccharides, glycoproteins, hormones, receptors, antigens, antibodies, affybodies, antibody mimics, viruses, pathogens, toxic substances, substrates, metabolites, transition state analogs, cofactors, inhibitors, drugs, dyes, nutrients, growth factors, cells, tissues, and any fragment or portion of any of the foregoing. In some embodiments, a target molecule is a protein, in which case the target molecule may be referred to as a "target protein."

Polyanionic inhibitor: A polyanionic inhibitor is an inhibitor molecule that comprises or mimics the polyanionic phosphate backbone of a nucleic acid molecule. In some embodiments, a polyanionic inhibitor is included in a binding reaction with an aptamer to increase the stringency of the binding conditions. Nonlimiting exemplary polyanionic inhibitors include dextran sulfate, heparin, Z-block, poly-dI/dC, sonicated or sheared salmon sperm DNA, calf thymus DNA, dNTPs, and the like.

Z-Block: Z-block as used herein is a single-stranded oligonucleotide of sequence 5'-(AC-BndU-BndU)$_7$-AC-3', where BndU indicates a benzyl-substituted deoxyuridine residue. Z-block may be synthesized using conventional phosphoramidite chemistry Ranges provided herein are understood to be shorthand for all of the values within the range. For example, a range of 1 to 50 is understood to include any number, combination of numbers, or sub-range from 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (as well as fractions thereof unless the context clearly dictates otherwise). Any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, "about" or "consisting essentially of mean±20% of the indicated range, value, or structure, unless otherwise indicated. As used herein, the terms "include" and "comprise" are open ended and are used synonymously. It should be understood that the terms "a" and "an" as used herein refer to "one or more" of the enumerated components. The use of the alternative (e.g., "or") should be understood to mean either one, both, or any combination thereof of the alternatives.

II. Overview

A. Growth Differentiation Factor 8 (GDF8; Myostatin) and GDF11 Proteins

The native mature forms of myostatin and GDF11 are homodimers and are about 90% identical by sequence alignment, with 98 of 109 matching amino acid residues. See amino acid sequence alignment for GDF11 (Protein ID O95390; amino acids 1 to 407; SEQ ID NO: 57) and myostatin (Protein ID O14793; amino acids 1 to 375; SEQ ID NO: 58), mature form indicated by gray bar. The alignment of the amino acid sequences of GDF11 and myostatin prepropeptides are shown below. The mature protein portions are highlighted with the gray bar.

```
---MVLAAPLLLGFLLLALELRPRGEAAEGPAAAAAAAAAAAAAGVGGERSSRPAPSVAP  57    O95390   GDF11_HUMAN
MQKLQLCVYIY-LFMLI--V--------AGPVDL---------------NENSEQKENVE  34    O14793   GDF8_HUMAN
    : *..  :    *:*:              **.               ...  ..

EPDGCPVCVWRQHSRELRLESIKSQILSKLRLKEAPNISREVVKQLLPKAPPLQQILDLH 117    O95390   GDF11_HUMAN
KEGLCNACTWRQNTKSSRIEAIKIQILSKLRLETAPNISKDVIRQLLPKAPPLREIDQY   94    O14793   GDF8_HUMAN
 :  * .*.***.::. *:*:** ********: *****::*:;********:::.*  :

DFQGDALQPEDFLEEDEYHATTETVISMAQETDPAVQTDGSPLCCHFHFSPKVMFTKVLK 177    O95390   GDF11_HUMAN
DVQRDDS-SDGSLEDDDYHATTETIITMPTESDPLMQVDGKPKCCFFKSSKIQYNKVVK  153    O14793   GDF8_HUMAN
*.* *     ::*:.*******:*:*    *:.*   :*.**.* **.*:** *:  :.**:*

AQLWVYLRPVPRPATVYLQILRLKPLTGEGTAGGGGGGRRHIRIRSLKIELHGRSGHWQS 237    O95390   GDF11_HUMAN
AQLWIYLRPVETPTTVFVQILRLIKPMKD--------GTRYTGIRSLKLDMNPGTGIWQS 205    O14793   GDF8_HUMAN
****:***** *:**.:*****    :           * *: *****:::* :* ***

IDFKQVLHSWFRQPQSNWGIEINAFDPSGTDLAVTSLGPGAEGLHPFMELVVLENTKRSR 296    O95390   GDF11_HUMAN
IDVKTVLQNWLKQPESNLGIEIKALDENGHDLAVTFPGPGEDGLNPFLEVKVTDTPKRSR 265    O14793   GDF8_HUMAN
**.*  **:.*::**.** ****.*:*  .* ***** *** :**.**:*:.* :: ****

357    O95390   GDF11_HUMAN
RNLGLDCDEHSSESRCCRYPLTVDFEAFGWDWIIAPKRYKANYCSGQCEYMFMQKYPHTH 325    O14793   GDF8_HUMAN
RDFGLDCDEHSTESRCCRYPLTVDFEAFGWDWIIAPKRYKANYCSGECEFVFLQKYPHTH
*::********:.*********************************.**:.*:*******

357    O95390   GDF11_HUMAN
LVQQANPRGSAGPCCTPTKMSPINMLYFNDMQQIIYGKIPGMVVDRCGCS            325    O14793   GDF8_HUMAN
LVHQANPRGSAGPCCTPTKMSPINMLYFNGKEQIIYGKIPAMVVDRCGCS
**:*******************************  *:********:*********
```

GDF11 and GDF8 are thought to share common ancestry and common regulatory mechanism, yet have diverged with regard to their tissue specificity (primarily heart and muscle, respectively).

Myostatin (GDF8) is 100% identical between human, mouse, and rat. Amino acid sequence alignment of human, mouse and rat myostatin protein (mature) is show below. Human myostatin (GDF8) Protein ID is O14793; an exemplary human mature GDF8 is shown below; SEQ ID NO: 51). Mouse GDF8 Protein ID is O08689; an exemplary mouse mature GDF8 is shown below; SEQ ID NO: 52). Rat GDF11 Protein ID is O35312; an exemplary rat mature GDF8 is shown below; SEQ ID NO: 53).

B. SELEX

SELEX generally includes preparing a candidate mixture of nucleic acids, binding of the candidate mixture to the desired target molecule to form an affinity complex, separating the affinity complexes from the unbound candidate nucleic acids, separating and isolating the nucleic acid from the affinity complex, purifying the nucleic acid, and identifying a specific aptamer sequence. The process may include multiple rounds to further refine the affinity of the selected aptamer. The process can include amplification steps at one or more points in the process. See, e.g., U.S. Pat. No. 5,475,096, entitled "Nucleic Acid Ligands". The SELEX process can be used to generate an aptamer that covalently

```
 1   DFGLDCDEHSTESRCCRYPLTVDFEAFGWDWIIAPKRYKANYCSGECEFVFLQKYPHTHL  60    O14793   GDF8_HUMAN
 1   DFGLDCDEHSTESRCCRYPLTVDFEAFGWDWIIAPKRYKANYCSGECEFVFLQKYPHTHL  60    O08689   GDF8_MOUSE
 1   DFGLDCDEHSTESRCCRYPLTVDFEAFGWDWIIAPKRYKANYCSGECEFVFLQKYPHTHL  60    O35312   GDF8_RAT
     ************************************************************

61   VHQANPRGSAGPCCTPTKMSPINMLYFNGKEQIIYGKIPAMVVDRCGCS            109    O14793   GDF8_HUMAN
61   VHQANPRGSAGPCCTPTKMSPINMLYFNGKEQIIYGKIPAMVVDRCGCS            109    O08689   GDF8_MOUSE
61   VHQANPRGSAGPCCTPTKMSPINMLYFNGKEQIIYGKIPAMVVDRCGCS            109    O35312   GDF8_RAT
     ************************************************
```

Mature GDF11 is 100% identical between human and mouse, and 99% identical in rat. Amino acid sequence alignment of human, mouse and rat GDF11 protein (mature) is show below. Human GDF11 Protein ID is O95390; an exemplary human mature GDF11 is shown below; SEQ ID NO: 54). Mouse GDF11 Protein ID is Q9Z1W4; an exemplary mouse mature GDF8 is shown below; SEQ ID NO: 55). Rat GDF11 Protein ID is Q9Z217; an exemplary rat mature GDF8 is shown below; SEQ ID NO: 56).

binds its target as well as an aptamer that non-covalently binds its target. See, e.g., U.S. Pat. No. 5,705,337 entitled "Systematic Evolution of Nucleic Acid Ligands by Exponential Enrichment: Chemi-SELEX."

The SELEX process can be used to identify high-affinity aptamers containing modified nucleotides that confer improved characteristics on the aptamer, such as, for example, improved in vivo stability or improved delivery characteristics. Examples of such modifications include

```
 1   NLGLDCDEHSSESRCCRYPLTVDFEAFGWDWIIAPKRYKANYCSGQCEYMFKQKYPHTHL  60    O95390   GDF11_HUMAN
 1   NLGLDCDEHSSESRCCRYPLTVDFEAFGWDWIIAPKRYKANYCSGQCEYMFKQKYPHTHL  60    Q9Z1W4   GDF11_MOUSE
 1   NLGLDCDEHSSESRCCRYPLTVDFEASGWDWIIAPKRYKANYCSGQCEYMFKQKYPHTHL  60    Q9Z217   GDF11_RAT
     *************************  *********************************

61   VQQANPRGSAGPCCTPTKMSPINMLYFNDKQQIIYGKIPGMVVDRCGCS            109    O95390   GDF11_HUMAN
61   VQQANPRGSAGPCCTPTKMSPINMLYFNDKQQIIYGKIPGMVVDRCGCS            109    Q9Z1W4   GDF11_MOUSE
61   VQQANPRGSAGPCCTPTKMSPINMLYFNDKQQIIYGKIPGMVV------            103    Q9Z217   GDF11_RAT
     ******************************************
``` chemical substitutions at the ribose and/or phosphate and/or base positions. SELEX process-identified aptamers containing modified nucleotides are described in U.S. Pat. No. 5,660,985, entitled "High Affinity Nucleic Acid Ligands Containing Modified Nucleotides", which describes oligonucleotides containing nucleotide derivatives chemically modified at the 5'- and 2'-positions of pyrimidines. U.S. Pat. No. 5,580,737, see supra, describes highly specific aptamers containing one or more nucleotides modified with 2'-amino (2'-NH2), 2'-fluoro (2'-F), and/or 2'-O-methyl (2'-OMe). See also, U.S. Patent Application Publication 20090098549, entitled "SELEX and PHOTOSELEX", which describes nucleic acid libraries having expanded physical and chemical properties and their use in SELEX and photoSELEX.

SELEX can also be used to identify aptamers that have desirable off-rate characteristics. See U.S. Patent Application Publication 20090004667, entitled "Method for Generating Aptamers with Improved Off-Rates", which describes improved SELEX methods for generating aptamers that can bind to target molecules. As mentioned above, these slow off-rate aptamers are known as "SOMAmers." Methods for producing aptamers or SOMAmers and photoaptamers or SOMAmers having slower rates of dissociation from their respective target molecules are described. The methods involve contacting the candidate mixture with the target molecule, allowing the formation of nucleic acid-target complexes to occur, and performing a slow off-rate enrichment process wherein nucleic acid-target complexes with fast dissociation rates will dissociate and not reform, while complexes with slow dissociation rates will remain intact. Additionally, the methods include the use of modified nucleotides in the production of candidate nucleic acid mixtures to generate aptamers or SOMAmers with improved off-rate performance.

A variation of this assay employs aptamers that include photoreactive functional groups that enable the aptamers to covalently bind or "photocrosslink" their target molecules. See, e.g., U.S. Pat. No. 6,544,776 entitled "Nucleic Acid Ligand Diagnostic Biochip". These photoreactive aptamers are also referred to as photoaptamers. See, e.g., U.S. Pat. Nos. 5,763,177, 6,001,577, and 6,291,184, each of which is entitled "Systematic Evolution of Nucleic Acid Ligands by Exponential Enrichment: Photoselection of Nucleic Acid Ligands and Solution SELEX"; see also, e.g., U.S. Pat. No. 6,458,539, entitled "Photoselection of Nucleic Acid Ligands". After the microarray is contacted with the sample and the photoaptamers have had an opportunity to bind to their target molecules, the photoaptamers are photoactivated, and the solid support is washed to remove any non-specifically bound molecules. Harsh wash conditions may be used, since target molecules that are bound to the photoaptamers are generally not removed, due to the covalent bonds created by the photoactivated functional group(s) on the photoaptamers.

In both of these assay formats, the aptamers or SOMAmers are immobilized on the solid support prior to being contacted with the sample. Under certain circumstances, however, immobilization of the aptamers or SOMAmers prior to contact with the sample may not provide an optimal assay. For example, pre-immobilization of the aptamers or SOMAmers may result in inefficient mixing of the aptamers or SOMAmers with the target molecules on the surface of the solid support, perhaps leading to lengthy reaction times and, therefore, extended incubation periods to permit efficient binding of the aptamers or SOMAmers to their target molecules. Further, when photoaptamers or photoSOMAmers are employed in the assay and depending upon the material utilized as a solid support, the solid support may tend to scatter or absorb the light used to effect the formation of covalent bonds between the photoaptamers or photoSOMAmers and their target molecules. Moreover, depending upon the method employed, detection of target molecules bound to their aptamers or photoSOMAmers can be subject to imprecision, since the surface of the solid support may also be exposed to and affected by any labeling agents that are used. Finally, immobilization of the aptamers or SOMAmers on the solid support generally involves an aptamer or SOMAmer-preparation step (i.e., the immobilization) prior to exposure of the aptamers or SOMAmers to the sample, and this preparation step may affect the activity or functionality of the aptamers or SOMAmers.

SOMAmer assays that permit a SOMAmer to capture its target in solution and then employ separation steps that are designed to remove specific components of the SOMAmer-target mixture prior to detection have also been described (see U.S. Patent Application Publication 20090042206, entitled "Multiplexed Analyses of Test Samples"). The described SOMAmer assay methods enable the detection and quantification of a non-nucleic acid target (e.g., a protein target) in a test sample by detecting and quantifying a nucleic acid (i.e., a SOMAmer). The described methods create a nucleic acid surrogate (i.e., the SOMAmer) for detecting and quantifying a non-nucleic acid target, thus allowing the wide variety of nucleic acid technologies, including amplification, to be applied to a broader range of desired targets, including protein targets.

Embodiments of the SELEX process in which the target is a peptide are described in U.S. Pat. No. 6,376,190, entitled "Modified SELEX Processes Without Purified Protein." In the instant case, the target is the GDF8 protein.

C. Chemically Modified Aptamers

Aptamers may contain modified nucleotides that improve it properties and characteristics. Non-limiting examples of such improvements include, in vivo stability, stability against degradation, binding affinity for its target, and/or improved delivery characteristics.

Examples of such modifications include chemical substitutions at the ribose and/or phosphate and/or base positions of a nucleotide. SELEX process-identified aptamers containing modified nucleotides are described in U.S. Pat. No. 5,660,985, entitled "High Affinity Nucleic Acid Ligands Containing Modified Nucleotides," which describes oligonucleotides containing nucleotide derivatives chemically modified at the 5'- and 2'-positions of pyrimidines. U.S. Pat. No. 5,580,737, see supra, describes highly specific aptamers containing one or more nucleotides modified with 2'-amino (2'-NH$_2$), 2'-fluoro (2'-F), and/or 2'-O-methyl (2'-OMe). See also, U.S. Patent Application Publication No. 20090098549, entitled "SELEX and PHOTOSELEX," which describes nucleic acid libraries having expanded physical and chemical properties and their use in SELEX and photoSELEX.

Specific examples of a C-5 modification include substitution of deoxyuridine at the C-5 position with a substituent independently selected from: benzylcarboxyamide (alternatively benzylaminocarbonyl) (Bn), naphthylmethylcarboxyamide (alternatively naphthylmethylaminocarbonyl) (Nap), tryptaminocarboxyamide (alternatively tryptaminocarbonyl) (Trp), and isobutylcarboxyamide (alternatively isobutylaminocarbonyl) (iBu) as illustrated immediately below.

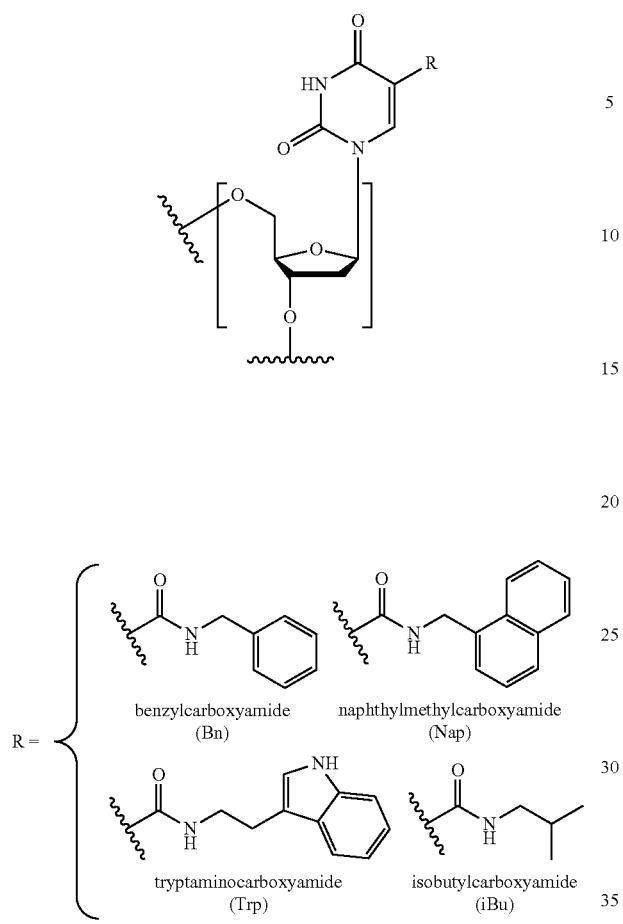

nucleotide components. A polynucleotide can be further modified after polymerization, such as by conjugation with a labeling component.

Additional non-limiting examples of modified nucleotides (e.g., C-5 modified pyrimidine) that may be incorporated into the nucleic acid sequences of the present disclosure include the following:

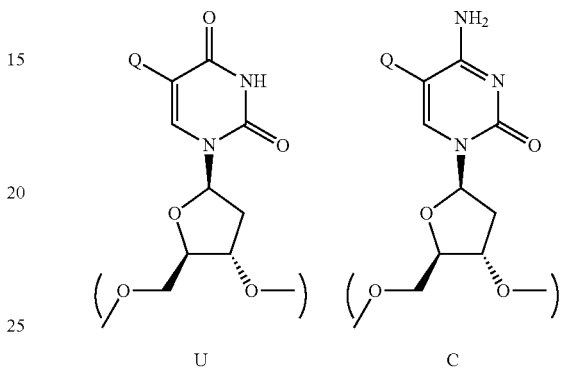

Chemical modifications of a C-5 modified pyrimidine can also be combined with, singly or in any combination, 2'-position sugar modifications, modifications at exocyclic amines, and substitution of 4-thiouridine and the like.

Representative C-5 modified pyrimidines include: 5-(N-benzylcarboxamide)-2'-deoxyuridine (BndU), 5-(N-benzylcarboxamide)-2'-0-methyluridine, 5-(N-benzylcarboxamide)-2'-fluorouridine, 5-(N-isobutylcarboxamide)-2'-deoxyuridine (iBudU), 5-(N-isobutylcarboxamide)-2'-0-methyluridine, 5-(N-isobutylcarboxamide)-2'-fluorouri- dine, 5-(N-tryptaminocarboxamide)-2'-deoxyuridine (TrpdU), 5-(N-tryptaminocarboxamide)-2'-0-methyluridine, 5-(N-tryptaminocarboxamide)-2'-fluorouridine, 5-(N-[1-(3-trimethylammonium) propyl]carboxamide)-2'-deoxyuridine chloride, 5-(N-naphthylmethylcarboxamide)-2'-deoxyuridine (NapdU), 5-(N-naphthylmethylcarboxamide)-2'-0-methyluridine, 5-(N-naphthylmethylcarboxamide)-2'-fluorouridine or 5-(N-[1-(2,3-dihydroxypropyl)]carboxamide)-2'-deoxyuridine).

If present, a modification to the nucleotide structure can be imparted before or after assembly of the polynucleotide. A sequence of nucleotides can be interrupted by non-

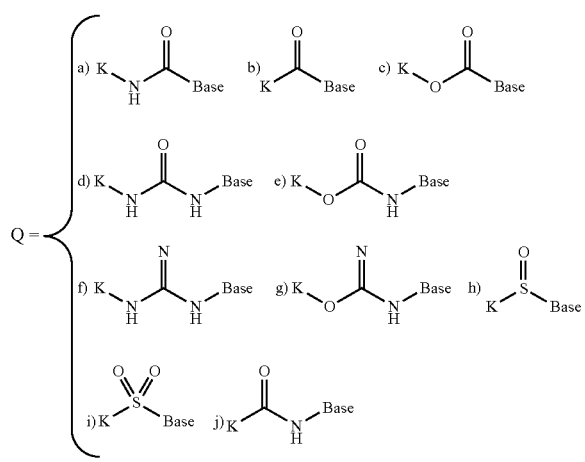

Base = Uridine (U) or Cytidine (C) (attachment is to the 5 position)
K = R' group plus (CH$_2$)$_n$ connecting group, where n = 0-3

R' is defined as follows:

R' = 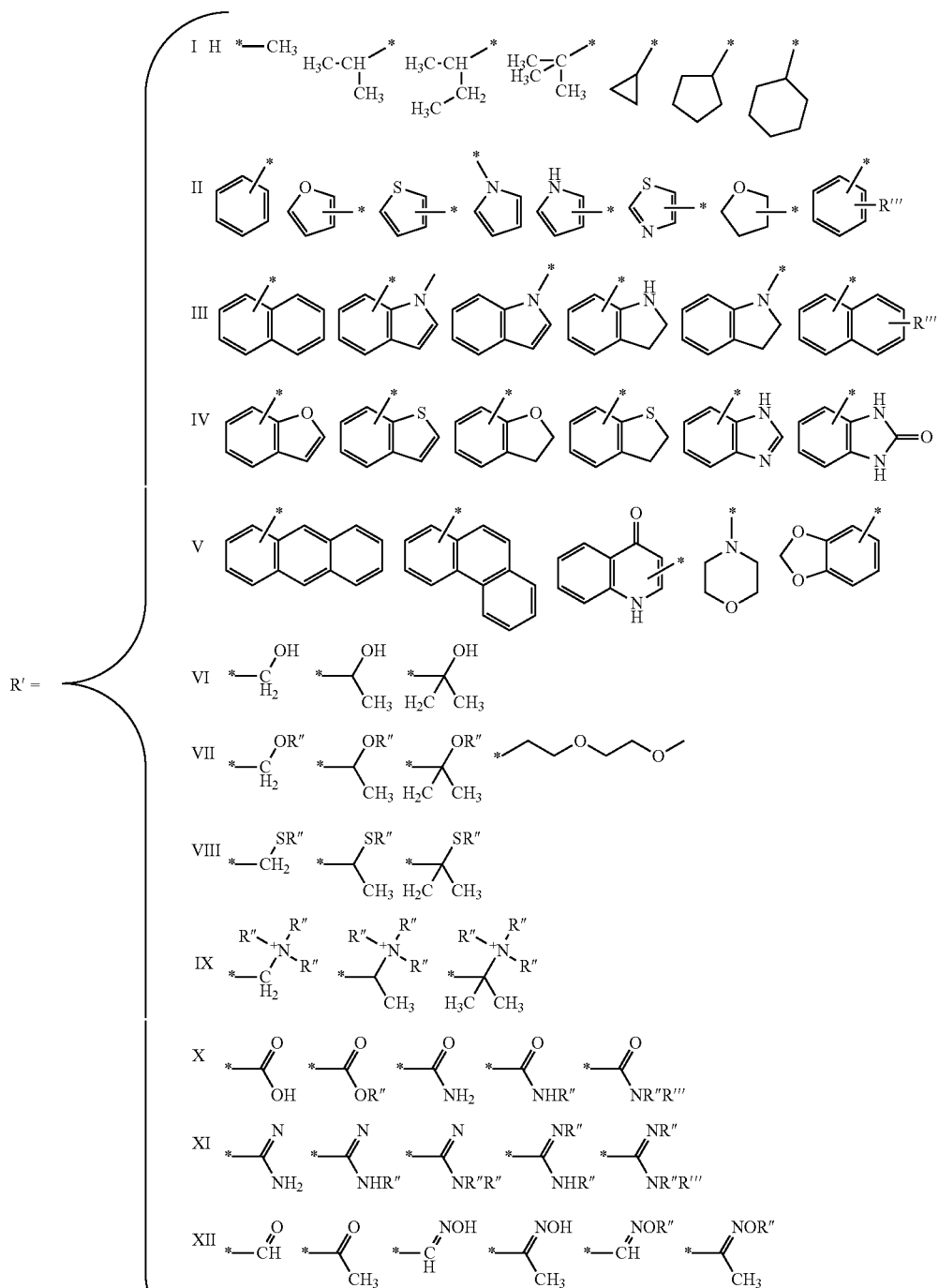

*Denotes point of attachment of the R' group to (CH$_2$)$_n$ connecting group

And, R'', R''' and R'''' are defined as follows:
  wherein
    R'''' is selected from the group consisting of a branched or linear lower alkyl (C1-C20); halogen (F, Cl, Br, I); nitrite (CN); boronic acid (BO$_2$H$_2$); carboxylic acid (COOH); carboxylic acid ester (COOR''); primary amide (CONH$_2$); secondary amide (CONHR''); tertiary amide (CONR''R'''); sulfonamide (SO$_2$NH$_2$); N-alkyl-sulfonamide (SONHR''),
  wherein
    R'', R''' are independently selected from a group consisting of a branched or linear lower alkyl (C1-C2); phenyl (C$_6$H$_5$); an R'''' substituted phenyl ring (R''''C$_6$H$_4$); wherein R'''' is defined above; a carboxylic acid (COOH); a carboxylic acid ester (COOR''''); wherein R'''' is a branched or linear lower alkyl (C1-C20); and cycloalkyl; wherein R''=R'''=(CH$_2$)$_n$; wherein n=2-10.

Further C-5 modified pyrimidine nucleotides include the following:

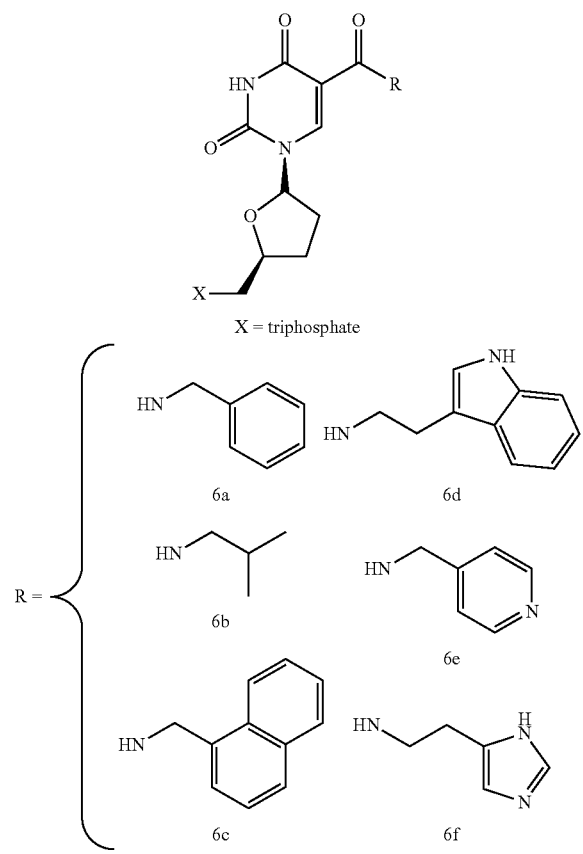

In some embodiments, the modified nucleotide confers nuclease resistance to the aptamer. A pyrimidine with a substitution at the C-5 position is an example of a modified nucleotide. Modifications can include backbone modifications, methylations, unusual base-pairing combinations such as the isobases isocytidine and isoguanidine, and the like. Modifications can also include 3' and 5' modifications, such as capping. Other modifications can include substitution of one or more of the naturally occurring nucleotides with an analog, internucleotide modifications such as, for example, those with uncharged linkages (e.g., methyl phosphonates, phosphotriesters, phosphoamidates, carbamates, etc.) and those with charged linkages (e.g., phosphorothioates, phosphorodithioates, etc.), those with intercalators (e.g., acridine, psoralen, etc.), those containing chelators (e.g., metals, radioactive metals, boron, oxidative metals, etc.), those containing alkylators, and those with modified linkages (e.g., alpha anomeric nucleic acids, etc.). Further, any of the hydroxyl groups ordinarily present on the sugar of a nucleotide may be replaced by a phosphonate group or a phosphate group; protected by standard protecting groups; or activated to prepare additional linkages to additional nucleotides or to a solid support. The 5' and 3' terminal OH groups can be phosphorylated or substituted with amines, organic capping group moieties of from about 1 to about 20 carbon atoms, polyethylene glycol (PEG) polymers in one embodiment ranging from about 10 to about 80 kDa, PEG polymers in another embodiment ranging from about 20 to about 60 kDa, or other hydrophilic or hydrophobic biological or synthetic polymers. In one embodiment, modifications are of the C-5 position of pyrimidines. These modifications can be produced through an amide linkage directly at the C-5 position or by other types of linkages.

Aptamers can also contain analogous forms of ribose or deoxyribose sugars that are generally known in the art, including 2'-O-methyl-, 2'-O-allyl, 2'-fluoro- or 2'-azido-ribose, carbocyclic sugar analogs, a-anomeric sugars, epimeric sugars such as arabinose, xyloses or lyxoses, pyranose sugars, furanose sugars, sedoheptuloses, acyclic analogs and abasic nucleoside analogs such as methyl riboside. As noted above, one or more phosphodiester linkages may be replaced by alternative linking groups. These alternative linking groups include embodiments wherein phosphate is replaced by P(O)S ("thioate"), P(S)S ("dithioate"), (O)NR$_2$ ("amidate"), P(O)R, P(O)OR', CO or CH$_2$ ("formacetal"), in which each R or R' is independently H or substituted or unsubstituted alkyl (1-20 C) optionally containing an ether (-O-) linkage, aryl, alkenyl, cycloalky, cycloalkenyl or araldyl. Not all linkages in an aptamer need be identical. Substitution of analogous forms of sugars, purines, and pyrimidines can be advantageous in designing a final product, as can alternative backbone structures like a polyamide backbone, for example.

Specific examples of C-5 modified pyrimidines that may be included or incorporated into an aptamer include, but are not limited to the structures herein. While the naming convention used for the structure assumes X is —H (i.e., DNA), they also encompass structures where X may be —OH (RNA), or other substituents described herein (e.g., —OCH$_3$; —O-allyl; —F, —OEt; —OPr, —NH$_2$; -azido or —OCH$_2$CH$_2$OCH$_3$), R' may —H; —OAc; —OBz; —OCH$_2$CH$_2$OCH$_3$ and —OSiMe$_2$tBu and R" may be —H; DMT and triphosphate (—P(O)(OH)—O—P(O)(OH)—O—P(O)(OH)$_2$), and salts thereof.

Exemplary NapdU Structure (5-[N-(1-naphthylmethyl) carboxamide]-2'-deoxyuridine) (wherein X is H):

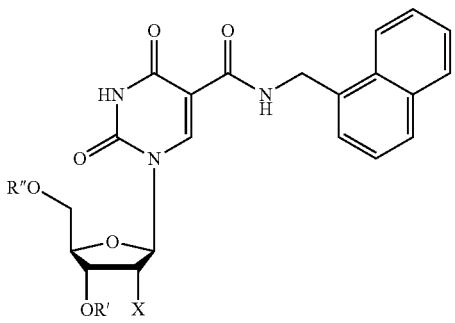

Exemplary 2NapdU structure (5-[N-(2-naphthylmethyl) carboxamide]-2'-deoxyuridine) (wherein X is H):

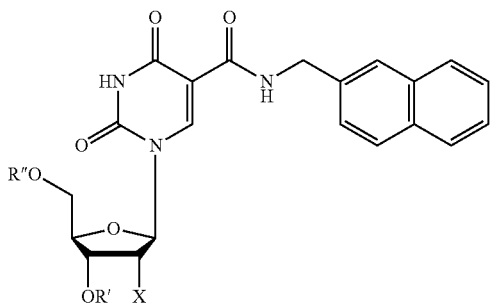

Exemplary PPdU structure (5-[N-(phenyl-3-propyl)carboxamide]-2'-deoxyuridine) (wherein X is H):

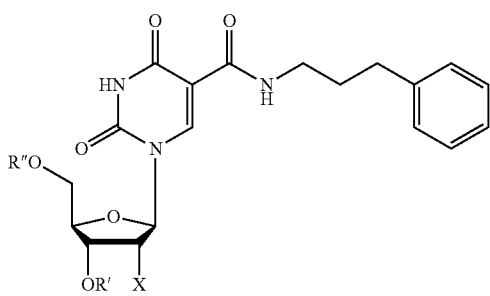

Exemplary TrpdU structure (5-[N-(3-indole-2-ethyl)carboxamide]-2'-deoxyuridine) (wherein X is H):

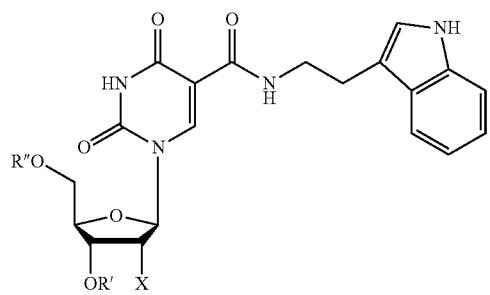

Exemplary 2NEdU structure 5-[N-(2-naphthyl-2-ethyl) carboxamide]-2'-deoxyuridine) (wherein X is H):

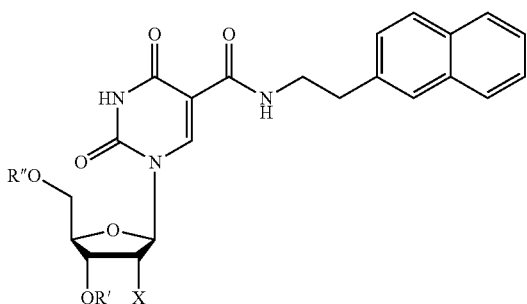

The following examples are provided to illustrate certain particular features and/or embodiments. These examples should not be construed to limit the disclosure to the particular features or embodiments described.

D. Exemplary GDF8 Aptamers

Provided herein are aptamers that bind GDF8. In some embodiments, an aptamer binds GDF8 with an affinity of less than 10 nM. In some such embodiments, the aptamer binds GDF11 with an affinity that is at least 10-fold weaker than the affinity for GDF8, when both affinities are measured under the same binding conditions. In some embodiments, the aptamer binds GDF8 with an affinity of between 0.5 nM and 10 nM and binds GDF11 with an affinity of greater than 50 nM, or greater than 100 nM, or greater than 150 nM, or greater than 200 nM, or greater than 300 nM. In some embodiments, the aptamer does not bind GDF11 under the same conditions under which the aptamer binds GDF8 with an affinity of less than 10 nM. In some embodiments, the aptamer binds GDF8 with an affinity of less than 8 nM, or less than 7 nM, or less than 6 nM, or less than 5 nM, or less than 4 nM, or less than 3 nM, or less than 2 nM, or less than 1 nM; or between 0.1 nM and 10 nM, between 0.1 nM and 8 nM, or between 0.1 nM and 5 nM.

In some embodiments, affinity determined using an assay described herein. In some embodiments, affinity is determined in the presence of a polyanionic inhibitor. Nonlimiting exemplary polyanionic inhibitors are described herein. In some embodiments, affinity is determined in the presence of Z block.

In some embodiments, an aptamer that binds GDF8 comprises the sequence:
5'-GWWR$^1$C$_n$R$^2$ZG$_n$GWC$_n$X$^2$CW$_n$WWX$^1$A$_n$R$^1$C$_n$X$^1$K W$_n$AGX$^2$$_n$WCX$^1$ZD-3' (SEQ ID NO: 1), wherein:
each W is independently, and for each occurrence, a C-5 modified pyrimidine;
X$^1$ and X$^2$ are each independently selected from W and C;
R$^1$ and R$^2$ are each independently selected from G and A;
each Z is independently selected from A and W;
K is selected from G and W;
D is selected from G, A, and W; and
each n is independently selected from 0 and 1.

In some embodiments, an aptamer that binds GDF8 is provided, wherein the aptamer comprises the sequence 5'-GWWR$^1$R$^2$ZGWC$_n$X$^2$CW$_n$WWX$^1$A$_n$R$^1$C$_n$X$^1$KAGWX CX$^1$ZD-3' (SEQ ID NO: 49), wherein:
each W is independently, and for each occurrence, a C-5 modified pyrimidine;
X$^1$ and X$^2$ are each independently selected from W and C;
R$^1$ and R$^2$ are each independently selected from G and A;
each Z is independently selected from A and W;
K is selected from G and W;
D is selected from G, A, and W; and
each n is independently selected from 0 and 1.

In some embodiments, an aptamer that binds GDF8 comprises a sequence selected from:

a)
(SEQ ID NO: 2)
5'-X$^1$GWWR$^1$C$_n$R$^2$ZG$_n$GWC$_n$X$^2$CW$_n$WWX$^1$A$_n$R$^1$C$_n$X$^1$KW$_n$AGX$^2$$_n$WCX$^1$ZD-3';
or b)
(SEQ ID NO: 3)
5'-WGWWAGZGWX$^2$CWWX$^1$AWGAGWCWAD-3' wherein W, Z, R$^1$, R$^2$, X$^1$, X$^2$, K, D, and n are defined as above.

In some embodiments, at least one X$^1$ is W. In some embodiments, each X$^1$ is W. In some embodiments, at least one or both R$^1$ is A. In some embodiments, at least one or both R$^2$ is G. In some embodiments, at least one or both Z is A. In some embodiments, K is G. In some embodiments, D is G. In some embodiments, at least 1, at least 2, at least 3, at least 4, at least 5, at least 6, at least 7, or 8 n are 0. In some embodiments, all n are 0. In some embodiments, at least 1, at least 2, at least 3, at least 4, at least 5, at least 6, at least 7, or 8 n are 1.

In some embodiments, a GDF8 aptamer is provided, wherein the aptamer comprises the sequence 5'-GWWA-GAGWCCWWWAWGAGWCWAG-3' (SEQ ID NO: 4), wherein each W is independently, and for each occurrence, a C-5 modified pyrimidine.

In any of the embodiments described herein, each W is independently selected from the C-5 modified pyrimidines described herein. In some embodiments, each P is selected from:
5-(N-tryptaminocarboxyamide)-2'-deoxyuridine (TrpdU),
5-(N-tryptaminocarboxyamide)-2'-O-methyluridine,
5-(N-tryptaminocarboxyamide)-2'-fluorouridine,
5-(N-1-naphthylmethylcarboxyamide)-2'-deoxyuridine (NapdU),
5-(N-1-naphthylmethylcarboxyamide)-2'-O-methyluridine,
5-(N-1-naphthylmethylcarboxyamide)-2'-fluorouridine,
5-(N-2-naphthylmethylcarboxyamide)-2'-deoxyuridine (2NapdU),
5-(N-2-naphthylmethylcarboxyamide)-2'-O-methyluridine,
5-(N-2-naphthylmethylcarboxyamide)-2'-fluorouridine,
5-(N-1-naphthylethylcarboxyamide)-2'-deoxyuridine (NEdU),
5-(N-1-naphthylethylcarboxyamide)-2'-O-methyluridine,
5-(N-1-naphthylethylcarboxyamide)-2'-fluorouridine,
5-(N-2-naphthylethylcarboxyamide)-2'-deoxyuridine (2NEdU),
5-(N-2-naphthylethylcarboxyamide)-2'-O-methyluridine,
5-(N-2-naphthylethylcarboxyamide)-2'-fluorouridine,
5-(N-3-benzofuranylethylcarboxyamide)-2'-deoxyuridine (BFdU),
5-(N-3-benzofuranylethylcarboxyamide)-2'-O-methyluridine,
5-(N-3-benzofuranylethylcarboxyamide)-2'-fluorouridine,
5-(N-3-benzothiophenylethylcarboxyamide)-2'-deoxyuridine (BTdU),
5-(N-3-benzothiophenylethylcarboxyamide)-2'-O-methyluridine, and
5-(N-3-benzothiophenylethylcarboxyamide)-2'-fluorouridine.

In some embodiments, at least 1, at least 2, at least 3, at least 4, at least 5, or at least 6 W are each independently selected from 5-(N-tryptaminocarboxyamide)-2'-deoxyuridine (TrpdU), 5-(N-tryptaminocarboxyamide)-2'-O-methyluridine, and 5-(N-tryptaminocarboxyamide)-2'-fluorouridine.

In some embodiments, a GDF8 aptamer comprises a sequence selected from SEQ ID NOs: 5 to 48. In some embodiments, a GDF8 aptamer comprises a sequence selected from SEQ ID NOs: 5 to 19, 26 to 28, 30 to 32, and 34 to 48. In some embodiments, a GDF8 aptamer comprises a sequence selected from SEQ ID NOs: 5 to 19, 26 to 28, and 30 to 32

In some embodiments, a GDF8 aptamer may include up to about 100 nucleotides, up to about 95 nucleotides, up to about 90 nucleotides, up to about 85 nucleotides, up to about 80 nucleotides, up to about 75 nucleotides, up to about 70 nucleotides, up to about 65 nucleotides, up to about 60 nucleotides, up to about 55 nucleotides, up to about 50 nucleotides, up to about 45 nucleotides, up to about 40 nucleotides, up to about 35 nucleotides, up to about 30 nucleotides, up to about 25 nucleotides, and up to about 20 nucleotides.

In some embodiments, the GDF8 aptamer may be at least about 95% identical, at least about 90% identical, at least about 85% identical, at least about 80% identical, or at least about 75% identical to a sequence selected from SEQ ID NOs: 5 to 19, 26 to 28, 30 to 32, and 34 to 48. In another embodiment, the GDF8 aptamer includes a sequence selected from SEQ ID NOs: 5 to 19, 26 to 28, 30 to 32, and 34 to 48. In another embodiment, the GDF8 aptamer includes a fragment of a sequence from SEQ ID NOs: 5 to 19, 26 to 28, 30 to 32, and 34 to 48 that binds GDF8 with an affinity (Kd) of less than 100 nM, less than 50 nM, less than 20 nM, or less than 10 nM. In a related aspect, the fragments thereof are from about 25 to 49 nucleotides in length (or from about 23, 24, 25, 26, 27, 28, 29, 30, 31, 32, 33, 34, 35, 36, 37, 38, 39, 40, 41, 42, 43, 44, 45, 46, 47, 48 or 49 nucleotides in length).

In some embodiments, the GDF8 aptamer may a dissociation constant ($K_d$) for GDF8 of about 10 nM or less. In another exemplary embodiment, the GDF8 aptamer has a dissociation constant ($K_d$) for the GDF8 protein of about 15 nM or less. In yet another exemplary embodiment, the GDF8 aptamer has a dissociation constant ($K_d$) for the GDF8 protein of about 20 nM or less. In yet another exemplary embodiment, the GDF8 aptamer has a dissociation constant ($K_d$) for the GDF8 protein of about 25 nM or less. In yet another exemplary embodiment, the GDF8 aptamer has a dissociation constant ($K_d$) for the GDF8 protein of about 30 nM or less. In yet another exemplary embodiment, the GDF8 aptamer has a dissociation constant ($K_d$) for the GDF8 protein of about 35 nM or less. In yet another exemplary embodiment, the GDF8 aptamer has a dissociation constant ($K_d$) for the GDF8 protein of about 40 nM or less. In yet another exemplary embodiment, the GDF8 aptamer has a dissociation constant ($K_d$) for the GDF8 protein of about 45 nM or less. In yet another exemplary embodiment, the GDF8 aptamer has a dissociation constant ($K_d$) for the GDF8 protein of about 50 nM or less. In yet another exemplary embodiment, the GDF8 aptamer has a dissociation constant ($K_d$) for the GDF8 protein in a range of about 3-10 nM (or 3, 4, 5, 6, 7, 8, 9 or 10 nM. A suitable dissociation constant can be determined with a binding assay using a multi-point titration and fitting the equation $y=(max-min)(Protein)/(K_d+Protein)+min$ as described herein. In other embodiments, the GDF8 aptamer is an aptamer with a $K_d$ that is less than or equal to the $K_d$ of an aptamer comprising the sequence of SEQ ID NO: 5.

In some embodiments, an aptamer comprises a detectable label.

Methods of Detecting GDF8

In some embodiments, methods of detecting GDF8 in a sample are provided, comprising contacting the sample with an aptamer described herein. In some embodiments, methods of detecting or quantifying GDF8 in the presence of GDF11 are provided, comprising contacting the sample suspected of containing both GDF8 and GDF11 with an aptamer described herein. In some embodiments, methods of distinguishing GDF8 from GDF11 in a sample are provided, comprising contacting the sample with an aptamer described herein. In some embodiments, the method comprises contacting the sample with a GDF8 aptamer described herein in the presence of a polyanionic inhibitor.

Detecting and/or quantifying GDF8 bound by the GDF8 aptamer can be accomplished using methods in the art and/or methods described herein. In some embodiments, the GDF8 aptamer comprises a detectable label. In some embodiments, the GDF8 aptamer is bound to a solid support, or comprises a member of a binding pair that may be captured on a solid support (for example, a biotinylated aptamer may be bound to a solid support comprising streptavidin).

Kits Comprising GDF8 Aptamer Compositions

The present disclosure provides kits comprising any of the GDF8 aptamers described herein. Such kits can comprise, for example, (1) at least one GDF8 aptamer; and (2) at least one pharmaceutically acceptable carrier, such as a solvent or solution. Additional kit components can optionally include, for example: (1) any of the pharmaceutically acceptable excipients identified herein, such as stabilizers, buffers, etc., (2) at least one container, vial or similar apparatus for holding and/or mixing the kit components; and (3) delivery apparatus.

EXAMPLES

Example 1

Selection and Identification of Aptamers Having GDF8 Binding Specificity

This example provides the representative method for the selection and production of aptamers that bind the mature GDF8 protein.

Previous attempts to select aptamers having specificity to GDF8 have been challenging. A comparison of protein binding affinity for myostatin (GDF8) and GDF11 of several aptamers selected using the SELEX process are shown in Table 1 below.

TABLE 1

| Aptamer Identifier | Affinity $K_d$ (nM) | | $K_d$ Ratio GDF8/GDF11 |
|---|---|---|---|
| | GDF8 | GDF11 | |
| 4 | 0.09 | 0.12 | 0.80 |
| 32 | 0.41 | 2.34 | 0.17 |
| 203 | 0.63 | 0.29 | 2.22 |

As shown in Table 1, the aptamers selected to bind GDF8 generally also had affinity for GDF11. The ratio of binding affinity for GDF8 to GDF11 for each aptamer is also shown in Table 1. The ratios vary from below one (1) (i.e., the aptamer had better affinity for myostatin compared to GDF11), to ratios of greater than one (i.e., the aptamer had a better affinity for GDF11 compared to myostatin). However, these affinity differences are not sufficient to discriminate between myostatin and GDF11 in a protein binding assay. As a result, the presence and/or levels of GDF11 and GDF8 cannot be distinguished. In light of the challenges of identifying a GDF8 aptamer that can discriminate GDF8 from GDF11, a counter-selection strategy was introduced into the SELEX process.

Aptamer Selection with Slow Off-Rate Enrichment Process

SELEX with GDF8 was performed using the SELEX methods described herein. In addition, protocol modifications involving passive counter-selections were applied to select GDF8 aptamers that do not bind GDF11 or have a greater affinity for GDF8 than GDF11.

Passive counter-selection was done with the unwanted target (GDF11) in untagged form by adding it to PCB (protein competitor buffer containing prothrombin, casein and albumin) during selection, removing sequences that lack preference for GDF8 over GDF11. The ratio of GDF11 to GDF8 was 1:1 in the first round (100 pmol each), 2:1 in the second round (20 pmol GDF11 and 10 pmol GDF8), and increased in subsequent rounds of SELEX as the GDF8 target concentration was reduced (20 pmol GDF11 and 0.1 pmol GDF8 or about 200:1).

Preparation of Candidate Mixture

A candidate mixture of partially randomized ssDNA oligonucleotides was prepared by polymerase extension of a DNA primer annealed to a biotinylated ssDNA template (shown in Table 2 below). The candidate mixture contained a 40 nucleotide randomized cassette containing dATP, dGTP, dCTP and 5-(N-tryptaminocarboxyamide)-2'-deoxyuridine (TrpdU).

TABLE 2

Sequences of Template and Primers

| Oligo Designation | Sequence (5'→3') | SEQ ID NO: |
|---|---|---|
| Template 1 | AB'AB'TTTTTTTTGGTCTCT TGTTCTGTTGTTG-(N)$_{40}$-CA GAGAGGGAGCGGAG | 59 |
| Primer 1 | ATATATATTCTCCGCTCCCTC TCTG | 60 |
| Primer 2 | AB'AB'TTTTTTTTGGTCTCT TGTTCTGTTGTTG | 61 |

B'=biotin

Five milliliters of a 50% slurry of Streptavidin Plus UltraLink Resin (PIERCE) was washed once with 2.5 mL of 20 mM NaOH, twice with 2.5 mL of SB18T0.05 (40 mM HEPES (4-(2-Hydroxyethyl)piperazine-1-ethanesulfonic acid) buffer adjusted to pH 7.5 with NaOH, 102 mM NaCl, 5 mM KCl, 5 mM MgCl2 and 0.05% TWEEN 20) and twice with 2.5 mL of 16 mM NaCl. One hundred and eighty nanomoles of template 1 (SEQ ID NO: 59) possessing two biotin residues (designated as B' in the sequence) and 40 randomized positions (designated as $N_{40}$ in the sequence) were added to the washed UltraLink SA beads and rotated at 37° C. for 2.5 hours. The beads were then washed three times with 16 mM NaCl. Between each wash, the beads were recovered by centrifugation.

One fourth of the beads, now containing the 45 nmol captured template, were suspended in 1.5 mL of extension reaction buffer (containing 45 nmol of primer (SEQ ID NO: 60), 1×SQ20 buffer (120 mM Tris-HCl, pH7.8, 10 mM KCl, 7 mM MgSO$_4$, 6 mM (NH$_4$)$_2$SO$_4$, 0.001% BSA and 0.1% Triton X-100), 470 units of KOD XL DNA Polymerase (EMD MILLIPORE), and 1 mM each of dATP, dCTP, dGTP and TrpdUTP). The beads were allowed to incubate with rotation at 68° C. for 2 hours. The beads were then washed once with SB18T0.01 (SB18 as above, but with 0.01% TWEEN-20) and twice with 16 mM NaCl.

The aptamer library was eluted from the beads with 1.0 mL of 40 mM NaOH. The eluted library was immediately neutralized with 15 μL of neutralizer (700 mM HCl, 180 mM HEPES, 0.45% TWEEN-20). Elution was repeated twice more, and the eluates were pooled. The library was concentrated with an AMICON Ultracel YM-10 filter to approximately 0.4 mL and the concentration of library determined by ultraviolet absorbance spectroscopy.

Biotin Labeling of Human GDF8

Untagged recombinant human GDF8-Protein purified in homodimeric form after over-expression in *E. coli* (Peprotech, catalog number 120-11) was biotinylated by covalent coupling of NHS-PEO4-biotin (PIERCE, EZ-Link NHS- PEG4-Biotin) to residues containing primary amines. Protein (1600 pmol in 80 µL) was mixed with a 4-fold molar excess of NHS-PEG4-biotin and the reaction was allowed to incubate at 20° C. for 1 hour. After the reaction was completed, unreacted NHS-PEG4-biotin was removed using a Zeba™ spin desalting column (PIERCE) where the buffer had been exchanged to SB18T0.05.

Aptamer Selection with Slow Off-Rate Enrichment Process

A total of 9 rounds of the SELEX process were completed with selection for affinity and slow off-rate. Prior to each round a counter selection was performed to reduce background and to reduce the likelihood of obtaining aptamers with nonspecific binding to protein. In addition, separate types of counter-selections were applied to force selection of GDF8 aptamers that do not bind the closely related, 90% identical protein GDF11. Counter selections were performed as follows.

For round 1, 100 µL of the DNA candidate mixture containing approximately 1 nmole of DNA in SB18T0.05 was heated at 95° C. for 5 minutes and then cooled to 70° C. for 5 minutes, then to 48° C. for 5 minutes and then transferred to a 37° C. block for 5 minutes. The sample was then combined with 10 µL of protein competitor mixture (0.1% HSA, 10 µM casein, 10 µM prothrombin, and 10 µM unlabeled GDF11 in SB18T0.05) and 1 mg (100 µL) of streptavidin beads.

For Rounds 2-9, a 68 µL aliquot of the DNA candidate mixture obtained from the previous round (68% of eDNA obtained from previous round) was mixed with 13 µL of 5×SB18T0.05. The sample was heated to 95° C. for 3 minutes and cooled to 37° C. at a rate of 0.1° C./second. The sample was then combined with 9 µL of protein competitor mixture (0.1% HSA, 10 µM prothrombin in SB18T0.05, and 10 µM unlabeled GDF11 in SB18T0.05), and 0.1 mg (10 µL) of SA beads and incubated at 37° C. for 10 minutes with mixing (standard SELEX). Beads were removed by magnetic separation.

Following the first counter selection the target protein was pre-immobilized on SA beads for the Round 1 selection process. To accomplish this, 0.5 mg of SA beads was mixed with 50 pmoles of biotin labeled target protein (myostatin homodimer) and incubated with shaking for 30 minutes at 37° C. Unbound target was removed by washing the beads twice with SB18T0.05. The counter-selected-DNA candidate mixture (100 µL) was added to the beads and incubated at 37° C. for 60 minutes with mixing. No slow off-rate enrichment process was employed in the first round and beads were simply washed 5 times for 2 min each with 100 µL SB18T0.05. Following the washes, the bound aptamer was eluted from the beads by adding 45 µL of 8 mM NaOH, and incubating at 37° C. for 5 minutes with mixing. The aptamer-containing-eluate (40 µL) was transferred to a new tube after magnetic separation of the beads. Elution was repeated once more with 45 µL of 8 mM NaOH, and incubating at 37° C. for 5 minutes with mixing. The eluates were combined (80 uL) and the solution neutralized by addition of 20 µL of 32 mM HCl and 2 µL Tris-HCl pH 7.5.

For Rounds 2-9, selections were performed with the DNA candidate mixture and target protein as described below while, in parallel, an identical selection was performed with the DNA candidate mixture, but without the target protein. Comparison of the Ct values obtained from PCR for the sample with target protein (signal S) and sample without target protein (background B) were used as a guide to reduce the target concentration in the next round. If the delta Ct value was greater than 4, but less than 8, the target protein was reduced three fold in the next round. If the delta Ct value was greater than 8, the target was reduced 10-fold in the next round.

Following these scheme, reductions in myostatin concentrations after the rounds of standard SELEX were 3-fold (Round 6), 10-fold (Round 7), 30-fold (Round 8), and 100-fold (Round 9).

For Round 2, labeled target protein (5 pmoles of myostatin homodimer in 10 µL) was mixed with 40 µL of counter selected DNA candidate mixture and incubated at 37° C. for 15 minutes. A slow off-rate enrichment process was begun by adding 50 µL of 10 mM dextran sulfate followed by the immediate addition of 0.1 mg of SA beads. This was allowed to incubate for 15 minutes at 37° C. with mixing. Beads were then washed 5 times with 100 µL of SB18T0.05. The aptamer strand was eluted from the beads by adding 105 µL of sodium perchlorate elution buffer (1.8 M NaClO4, 40 mM PIPES pH 6.8, 1 mM EDTA, 0.05% Triton X-100), and incubating at 37° C. for 10 minutes with mixing. Beads were removed by magnetic separation and 100 µL of aptamer eluate was transferred to a new tube containing primer capture beads (25 µL of 2.5 mg/mL SA beads with 12.5 pmol primer 2 (SEQ ID NO: 61) attached) and allowed to incubate for 30 minutes at 50° C. with mixing. Beads were then washed three times with 100 µL of SB18T0.05. The aptamer strand was eluted from the beads by adding 85 µL of 40 mM NaOH, and the eluate (80 µL) was neutralized with 20 µL of 160 mM HCl and 2 µL of 500 mM Tris-HCl pH 7.5.

Rounds 3 through 9 selections were performed as described for Round 2 except dextran sulfate was added 15 minutes (rounds 3-4), 30 minutes (round 5), 45 minutes (round 6), 60 minutes (round 7), 75 min (round 8), or 90 minutes (rounds 9-11) prior to the addition of beads. Partitioning was done with 0.1 mg Neutravidin Coated Sera-Mag SpeedBeads (Fisher Scientific, Catalog No. 09-981-155, or hereinafter referred to as NA beads, rounds 3, 5, 7, 9) or with 0.1 mg of SA beads (rounds 4, 6, 8).

The pool obtained after 9 rounds of SELEX showed good activity to warrant Ion Torrent ePCR and sequencing (Table 3). From each pool, 384 sequences were obtained for comparative sequence analysis followed by binding assays of the lead candidates.

TABLE 3

Affinity data for myostatin aptamer pools obtained with standard SELEX, and with passive counter-selection with GDF11.

| Target Protein | SELEX method | Passive Counter-selection | TrpdU Pool | $K_d$ (nM) |
|---|---|---|---|---|
| GDF8 | Modified | PCB + GDF11 | 14583 | 0.11 |

Aptamer Amplification and Purification

Selected aptamer DNA from each round was amplified and quantified by QPCR. 48 µL DNA was added to 12 µL QPCR Mix (10×KOD DNA Polymerase Buffer; Novagen #71157, diluted to 5×, 25 mM MgCl$_2$, 10 µM forward PCR primer (Primer 1, SEQ ID NO: 60), 10 µM biotinylated reverse PCR primer (Primer 2, SEQ ID NO: 61), 5×SYBR Green I, 0.075 U/µL KOD XL DNA Polymerase, and 1 mM each dATP, dCTP, dGTP, and dTTP) and thermal cycled in A BIO-RAD MyIQ QPCR instrument with the following protocol: 1 cycle of 96° C. for 15 seconds, 55° C. for 10 seconds, and 68° C. for 30 minutes; followed by 30 cycles of 96° C. for 15 seconds, 68° C. for 1 minute. Quantification was done with the instrument software and the number of copies of DNA selected, with and without target protein, was compared to determine signal/background ratios.

Following amplification, the PCR product was captured on SA beads via the biotinylated antisense strand. 1.25 mL SA beads (10 mg/mL) were washed once with 14 mL 20 mM NaOH, twice with 14 mL SB18T0.05, resuspended in 1.25 mL 3 M NaCl+0.05% TWEEN, and stored at 4° C. 25 μL SA beads (10 mg/mL in 3 M NaCl) were added to 50 μL double-stranded QPCR products and incubated at 25° C. for 5 minutes with mixing. The "sense" strand was eluted from the beads by adding 100 μL of 40 mM NaOH, and incubating at 37° C. for 5 minutes with mixing. The eluted strand was discarded and the beads were washed twice with SB18T and once with 16 mM NaCl.

Aptamer sense strand containing TrpdUTP was prepared by primer extension from the immobilized antisense strand. The beads were suspended in 40 μL primer extension reaction mixture (1× Primer Extension Buffer (120 mM Tris-HCl pH 7.8, 10 mM KCl, 7 mM MgSO$_4$, 6 mM (NH$_4$)$_2$SO$_4$, 0.1% TRITON X-100 and 0.001% bovine serum albumin), 2.5 μM forward primer (Primer 1, SEQ ID NO: 60), 0.5 mM each dATP, dCTP, dGTP, and TrpdUTP, and 0.015 U/μL KOD XL DNA Polymerase) and incubated at 68° C. for 60 minutes with mixing. The beads were washed 3 times with SB18T0.05, and the aptamer strand was eluted from the beads by adding 45 μL of 40 mM NaOH, and incubating at 37° C. for 5 minutes with mixing. 40 μL aptamer eluate was transferred to a new tube after magnetic separation, and elution was repeated once more with 45 μL of 40 mM NaOH, and incubating at 37° C. for 5 minutes with mixing. The eluates were combined (80 uL) and the solution neutralized with 20 μL of 160 mM HCl and buffered with 10 μL of 0.1 M HEPES, pH 7.5.

Selection Stringency and Feedback

The relative target protein concentration of the selection step was lowered each round in response to the QPCR signal (ΔCt) following the rule below:

If $\Delta Ct < 4$, $[P]_{(i+1)} = [P]_{(i)}$
If $4 \leq \Delta Ct < 8$, $[P]_{(i+1)} = [P]_{(i)}/3.2$
If $\Delta Ct \geq 8$, $[P]_{(i+1)} = [P]_{(i)}/10$ Where [P]=protein concentration and i=current round number.

After each selection round, the convergence state of the enriched DNA mixture was determined. 10 μL double-stranded QPCR product was diluted to 200 μL with 4 mM MgCl$_2$ containing 1×SYBR Green I. Samples were analyzed for convergence using a C$_0$t analysis which measures the hybridization time for complex mixtures of double stranded oligonucleotides. Samples were thermal cycled with the following protocol: 3 cycles of 98° C. for 1 minute, 85° C. for 1 minute; 2 cycles of 98° C. for 1 minute, then 85° C. for 30 minutes. During the 30 minutes at 85° C., fluorescent images were measured at 5-second intervals. The fluorescence intensity was plotted as a function of the logarithm of time, and an increased rate of hybridization with each SELEX round was observed, indicating sequence convergence.

Enriched Pool Sequencing & Aptamer Identification

After 9 rounds of SELEX, the converged pool was sequenced. Sequence preparation was performed as follows. The pool was amplified by PCR using SELEX library-specific primers containing a unique barcode/index sequence (unique sequence identifier for each pool). Individual PCR products were quantified using a Quant-iT™ PicoGreen® dsDNA Reagent (LIFE TECHNOLOGIES) assay, combined at equimolar concentrations, and concentrated/buffer exchanged using an AMICON Ultra-0.5 Centrifugal Filter Device (MILLIPORE). The mixture was then purified by SDS-polyacrylamide gel electrophoresis (PAGE), and the eluate concentrated using an Amicon Ultra-0.5 Centrifugal Filter Device and visualized by PAGE to confirm the size, purity and yield of the final mix. The sample was submitted to SeqWright Genomic Services (GE HEALTHCARE, Houston, Tex.) for Ion Torrent PGM sequencing. From a sequence pool containing over 40,000 sequences, 384 were randomly selected and analyzed for convergence using custom software that determines sequence counts/copy number and identifies common convergence patterns using a local-alignment algorithm. Sequences with the greatest representation/copy number in the pool and at least one sequence from every convergence pattern were chosen for further characterization. Of note, those sequence reads from the SELEX aptamer pools that had a sequence quality score that was "low" (i.e., a Phred quality score of 20 or below) were removed from the sequence analysis and motif identification.

Aptamer Identification by Functional Assay

Sequence pattern 1 was originally identified from sequence 14583-49_3 (SEQ ID NO: 5) via comparative binding assays with myostatin and GDF11 (see Example 2). The letter "W" in the sequences indicate a TrpdU.

```
Aptamer ID 14583-49_3:
                                   (SEQ ID NO: 5)
5'-ctctg AWACGGCCWWAGWGWWAGAGWCCWWWAWGAGWCWAGACCA
caaca-3'
```

In parallel, sequence pattern 1 was identified in silico through analysis of the abundance of related sequences among 384 sequences in pool 14583 and through comparative analysis with sequences obtained using GDF11 in SELEX with the same TrpdU library. Sequence pattern 1 was highly enriched in pool 14583 from myostatin SELEX with passive counter-selection (9%) and was absent in pool 14582 from GDF11 SELEX. See Table 4.

TABLE 4

Sequence abundance in myostatin and GDF SELEX

|  | Pool 14583 (myostatin, passive counter-selection) | | Pool 14582 (GDF11, passive counter-selection) | |
| --- | --- | --- | --- | --- |
| Pattern | # seq | % seq | # seq | % seq |
| A | 15 | 3.9 | 43 | 11.2 |
| Pattern 1 | 35 | 9.1 | 0 | 0.0 |

Example 2

Equilibrium Binding Constant (K$_d$) for Aptamers to Myostatin (GDF8) Protein Versus GDF11

This example provides the protein binding affinities (K$_d$) for aptamer-GDF8 and aptamer-GDF11 protein, and the identification of aptamers that preferentially bind GDF8 over GDF11.

Several aptamer clones selected via the counter-selection SELEX method described herein were further characterized and selected for preferential binding to GDF8 over GDF11 (see Table 5). Binding assays were done in the absence and in the presence of 0.1-1 µM Z-block (random oligonucleotide sequence) as a non-specific competitor. An aptamer having BndU as the C-5 modified pyrimidine (BndU GDF11 aptamer), which was previously selected via SELEX without counter-selection steps and was used as a control for binding to both GDF11 and GDF8. Previous binding experiments with the BndU GDF11 aptamer showed that it is generally non-discriminatory for GDF11 and GDF8.

TABLE 5

Aptamer Binding Affinity Comparison: GDF8 (myostatin) and GDF11

| Aptamer ID | Counter-selection SELEX Method | Mod. base | Myostatin $K_d$ (nm) | GDF-11 $K_d$ (nM) | $K_d$ ratio |
|---|---|---|---|---|---|
| BndU GDF11 Aptamer | Standard | BndU | 0.11 | 0.05 | 0.45 |
| 14583-19* | Passive (GDF11 in buffer) | TrpdU | 1.16 | 0.42 | 0.36 |
| 14583-49 (SEQ ID NO: 5) | | TrpdU | 0.13 | 1.11 low plateau | 8.5 |

*5'-CTCTGAACWWCWAAWGWCWCWWGCAWWWWAWCGCAWWGAWWWCWCCAACA-3' (SEQ ID NO: 62)

Aptamer pool 14583 (TrpdU aptamers), which had been obtained by SELEX with passive counter-selection, contained few nucleotide sequences with high affinity, and a varying degree of selectivity, for myostatin (see $K_d$ ratio where a larger number indicates greater specificity for myostatin over GDF11). In particular, aptamer clone 14583-49_3 (TrpdU) showed about a 8.5-fold differential $K_d$ for myostatin over GDF11 (i.e., $K_d$ of 0.13 nM vs. 1.11 nM) when tested in the presence of 0.1 µM Z-block, and exhibit a low binding plateau for GDF-11 (FIG. 1).

Figure 2:
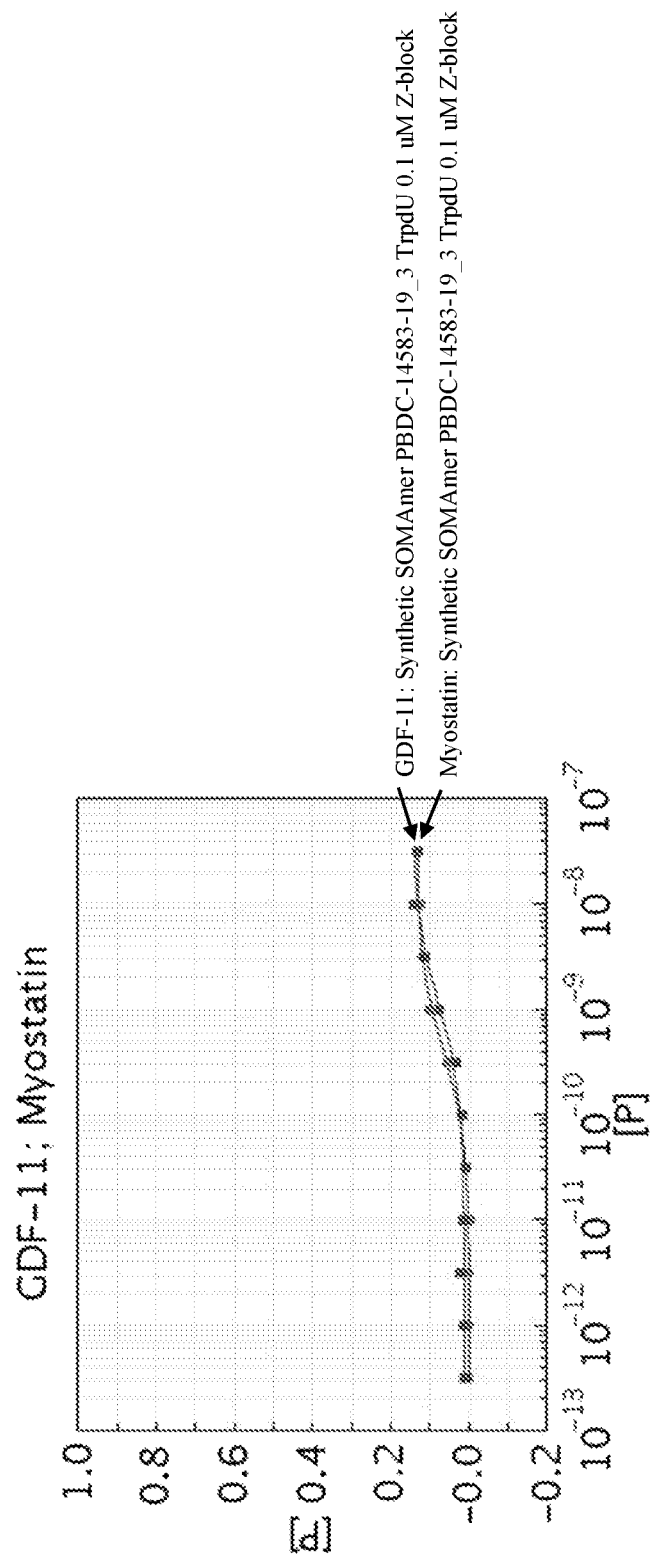
FIG. 2 shows a comparison of the binding affinities of aptamer 14583-19_3 for human GDF11 protein and human myostatin (GDF8) protein in the presence of a polyanionic inhibitor (Z-block). The x-axis shows the concentrations for the respective proteins and the y-axis shows the percent of the aptamer clone bound to the protein (1.0 is 100%).

The other aptamer clone of Table 5 is representative of highly abundant sequences with pattern A (see Table 4 above). Aptamer clone 14583-19 had a $K_d$ of 1.16 nM for myostatin, but also had a $K_d$ of 0.42 nM for GDF11 (FIG. 2).

Example 3

Post-SELEX Truncation and Analysis of Myostatin Aptamer 14583-49

This example provides post-SELEX myostatin binding affinities for truncated sequences of the 14583-49_3 aptamer and the identification of a core minimal sequence length that is capable of binding to myostatin.

Figure 3:
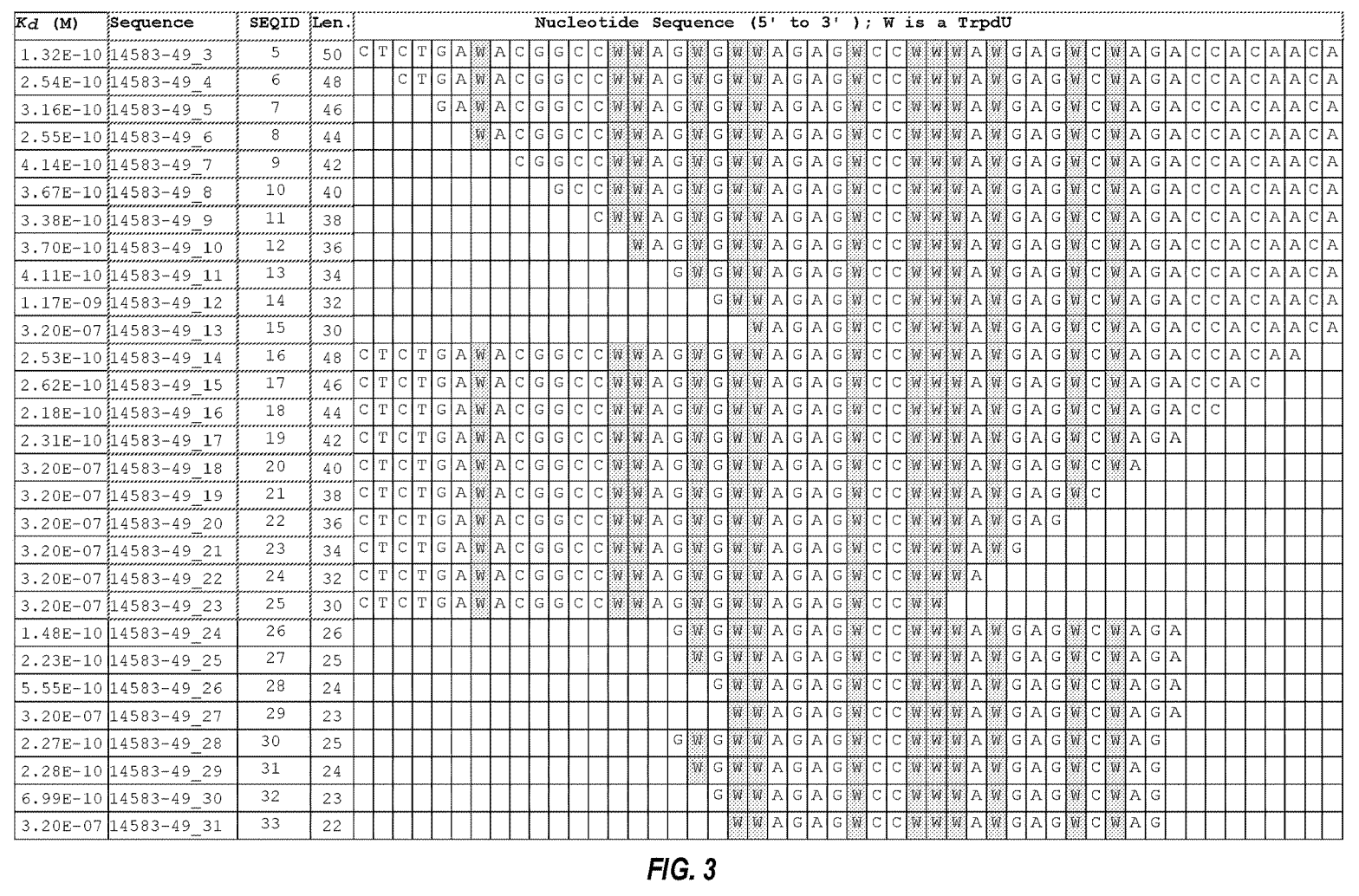

Aptamer 14583-49 (containing TrpdU) truncations indicated that the 23-mer sequence 5'-GWWAGAGWCCWW-WAWGAGWCWAG-3' (Aptamer 14583-49_30; SEQ ID NO: 32) was capable of binding myostatin. However, the activity of the 24-mer sequence 5'-WGWWAGAGWCCW-WWAWGAGWCWAG-3' (Aptamer clone 14583-49_29; SEQ ID NO: 31) showed slightly better binding to myostatin ($K_d$ of 2.28E-10) (see FIG. 3). This is consistent with the conserved motif 5'-WGWWAGAGWCCWWWWAWGAGW-CWAG-3' (SEQ ID NO: 31) found in a family of active clones related to 14583-49.

Figure 4:
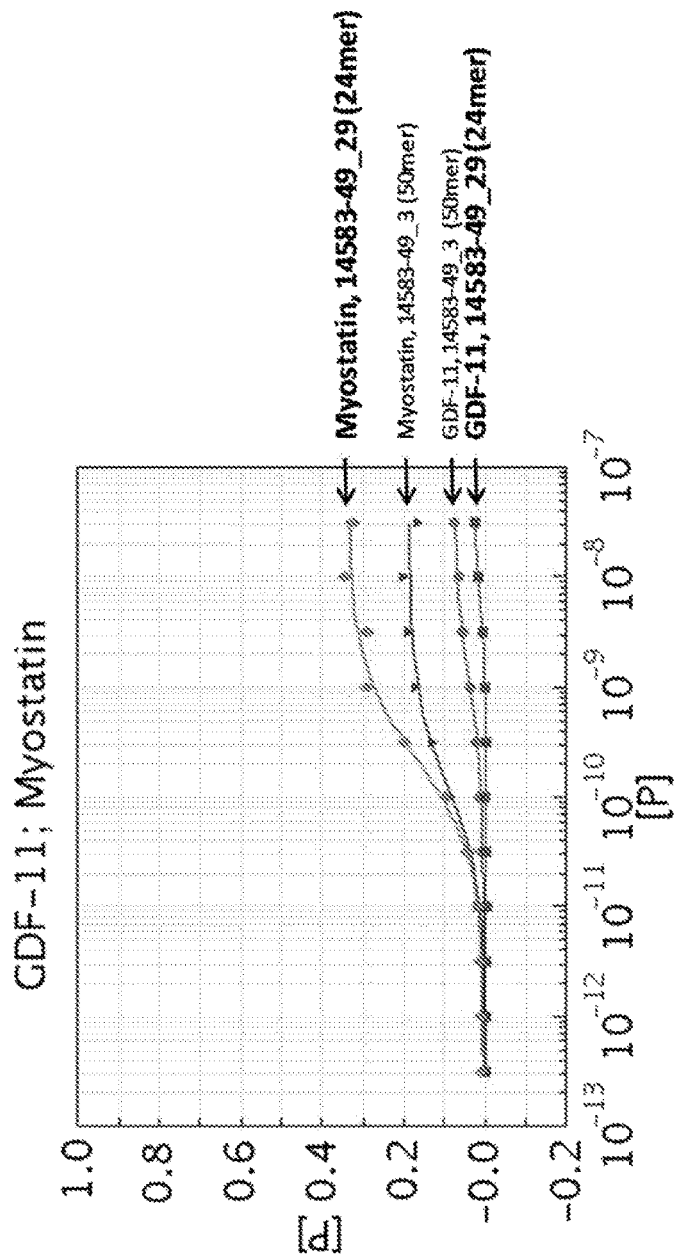
FIG. 4 shows a comparison of the binding affinities of aptamer clones 14583-49_29 and 14583-49_3 for human GDF8 protein and human GDF11 protein in the presence of a polyanionic inhibitor (Z-block). The x-axis shows the concentrations for the respective proteins and the y-axis shows the percent of the aptamer bound to the protein (1.0 is 100%).

The 24-mer truncated aptamer clone 14583-49_29; SEQ ID NO: 31) was equally active to the full-length 50mer aptamer 14583-49_3; SEQ ID NO: 5) ($K_d$ of 2.28E-10 for 24-mer and $K_d$ of 1.32E-10 for 50mer), but showed relatively better discrimination between binding of myostatin vs. GDF11 ($K_d$ of 2.28E-10 for myostatin and $K_d$ of >3.20E-07 for GDF-11) (FIG. 4).

Example 4

Additional GDF8 Aptamer Sequences

This example provides the results of a BLAST analysis of the SELEX aptamer pool using a lead GDF8 selective aptamer binder sequence (14583-49_3). This analysis resulted in the identification of additional aptamer sequences that also contained a common or core motif See Table 6 for the alignment of sequences.

From the alignment of the sequences in Table 6, several motif sequences may be derived, where each motif maintains overlap with the motif (or common sequence) identified from the alignment of the 14583-49_3 aptamer sequence in Examples 3 and 4.

The following motif may be defined from the motifs in Table 6:

(SEQ ID NO: 1)
5'-GWWR$^1$C$_n$R$^2$ZG$_n$GWC$_n$X$^2$CW$_n$WWX$^1$A$_n$R$^1$C$_n$X$^1$KW$_n$AGX$^2$$_n$WCX$^1$ZD-3', wherein:

each W is independently, and for each occurrence, a C-5 modified pyrimidine;

X$^1$ and X$^2$ are each independently selected from W and C;

R$^1$ and R$^2$ are each independently selected from G and A;

each Z is independently selected from A and W;

K is selected from G and W;

D is selected from G, A, and W; and each n is independently selected from 0 and 1. The affinity of certain sequences shown in Table 6 for myostatin was determined. Aptamer 14583-49_35 (SEQ ID NO: 35) was found to have an affinity (Kd) of 9.8 nM for myostatin and aptamer 14583-49_36 (SEQ ID NO: 40) was found to have an affinity (Kd) of 17.3 nM for myostatin. In contrast, aptamers 14583-49_37 (SEQ ID NO: 42) and 14583-49_38 (SEQ ID NO: 47) were found to have affinities (Kd) of greater than 320 nM for myostatin.

From that data, a submotif may be defined from the motifs in Table 6:

5'-GWWR$^1$R$^2$ZGWC$_n$X$^2$CW$_n$WWX$^1$A$_n$R$^1$C$_n$X$^1$KAGW XCX$^1$ZD-3' (SEQ ID NO: 49), wherein:

each W is independently, and for each occurrence, a C-5 modified pyrimidine;

X$^1$ and X$^2$ are each independently selected from W and C;

R$^1$ and R$^2$ are each independently selected from G and A;

each Z is independently selected from A and W;

K is selected from G and W;

D is selected from G, A, and W; and each n is independently selected from 0 and 1.

TABLE 6

Alignment of Aptamer Nucleotide Sequences with
GDF8 Binder Aptamer 14583-49_3 (SEQ ID NO: 5)

| SEQ ID NO: | Nucleotide Sequence (5' to 3') (each W is a TrpdU) |
|---|---|
| 34 | AWACGGCCWWAG WGWWA-GA-GW-CC-WWW-A-WG-AG-WCWAG ACCA |
| 35 | AWACAGWCWWAG WGWWA-GW-GW-WC-WWW-A-WG-AG-WCWAG ACWG |
| 36 | AWAWGGCCWWAG WGWWA-AW-GW-WC-WWW-A-WG-AG-WCWAG AWCG |
| 37 | AWWCGGCCWCAG WGWWG-GA-GW-CC-WWW-A-WW-AG-WCWAG ACAG |
| 38 | AWACGACCWWACG WGWWA-GA-GW-CC-WWW-A-WG-AGWWCWAA GAWCG |
| 39 | AWACAWCCWWAG WGWWA-GW-GW-CC-WWC-G-WG-AG-WCWAG ACCG |
| 40 | AWACGGWCWWAG WGWWA-GA-GWCCCWWWW-A-WG-AG-WCWAG AWWG |
| 41 | AWACGGCCWWAG CGWWA-GA-GW-CC-WWW-A-CG-AG-WCWAG AWWGC |
| 42 | AWWACGGCAWWAG WGWWA-GA-GW-CC-WWW-A-WGWAGCWCWAG AWG |
| 43 | AWGCGACCAWAG WGWWA-GA-GW-WC-WWW-A-WG-AG-WCWAG AWCG |
| 44 | CCWAG WGWWA-GW-GW-WC-WWW-A-WG-AG-WCWAG ACCG |
| 45 | AWAWGGCCCWAG WGWWA-GA-GW-WC-WWC-A-WG-AG-WCWAG ACGG |
| 46 | AWAWGCCWWAG WGWWA-GA-GW-CC-WWWAACWG-AG-WCWAG AWCG |
| 47 | AWACGACCWAG WGWWACGAGGW-CC-WWW-A-WG-AG-WCWAG ACGWA |
| 48 | AWAWGGCCWWAG WGWWA-GA-GW-CC-WWW-A-WG-AG-WCCWW AGACWGAC |

The invention claimed is:

1. An aptamer that binds GDF8, wherein the aptamer comprises the sequence:

5'-GWWR$^1$C$_n$R$^2$ZG$_n$GWC$_n$X$^2$CW$_n$WWX$^1$A$_n$R$^1$C$_n$X$^1$K W$_n$AGX$^2$$_n$WCX$^1$ZD-3' (SEQ ID NO: 1), wherein:
each W is independently, and for each occurrence, a C-5 modified pyrimidine;
X$^1$ and X$^2$ are each independently selected from W and C;
R$^1$ and R$^2$ are each independently selected from G and A;
each Z is independently selected from A and W;
K is selected from G and W;
D is selected from G, A, and W; and
each n is independently selected from 0 and 1;

or wherein the aptamer comprises the sequence:

5'-X$^1$GWWR$^1$C$_n$R$^2$ZG$_n$GWC$_n$X$^2$CW$_n$WWX$^1$A$_n$R$^1$C$_n$ X$^1$KW$_n$AGX$^2$$_n$WCX$^1$ZD-3' (SEQ ID NO: 2), wherein:
each W is independently, and for each occurrence, a C-5 modified pyrimidine;
X$^1$ and X$^2$ are each independently selected from W and C;
R$^1$ and R$^2$ are each independently selected from G and A;
each Z is independently selected from A and W;
K is selected from G and W;
D is selected from G, A, and W; and
each n is independently selected from 0 and 1;

or wherein the aptamer comprises the sequence:

5'-GWWR$^1$R$^2$ZGWC$_n$X$^2$CW$_n$WWX$^1$A$_n$R$^1$C$_n$X$^1$KAGW CX$^1$ZD-3' (SEQ ID NO: 49), wherein:

each W is independently, and for each occurrence, a C-5 modified pyrimidine;
X$^1$ and X$^2$ are each independently selected from W and C;
R$^1$ and R$^2$ are each independently selected from G and A;
each Z is independently selected from A and W;
K is selected from G and W;
D is selected from G, A, and W; and
each n is independently selected from 0 and 1;

or wherein the aptamer comprises the sequence:

5'-WGWWAGZGWX$^2$CWWX$^1$AWGAGWCWAD-3' (SEQ ID NO: 3), wherein:

each W is independently, and for each occurrence, a C-5 modified pyrimidine;
X$^1$ and X$^2$ are each independently selected from W and C;
Z is selected from A and W; and
D is selected from G, A, and W;

or wherein the aptamer comprises the sequence:

5'-GWWAGAGWCCWWWAWGAGWCWAG-3' (SEQ ID NO: 4), wherein each W is independently, and for each occurrence, a C-5 modified pyrimidine.

2. The aptamer of claim 1, wherein the aptamer binds GDF8 with an affinity of less than 10 nM, wherein, under the same conditions, the aptamer binds GDF11 with an affinity that is at least 10-fold weaker than the affinity for GDF8 or does not bind GDF 11.

3. The aptamer of claim 2, wherein the aptamer binds GDF8 with an affinity of less than 8 nM and binds GDF11 with an affinity greater than 100 nM.

4. The aptamer of claim 2, wherein affinity is determined using a binding assay comprising a polyanionic inhibitor selected from dextran sulfate, heparin, Z-block, poly-dI/dC, sonicated or sheared salmon sperm DNA, calf thymus DNA, and dNTPs.

5. The aptamer of claim 1, wherein at least one R$^1$ is A.
6. The aptamer of claim 1, wherein at least one R$^2$ is G.
7. The aptamer of claim 1, wherein K is G.
8. The aptamer of claim 1, wherein at least 1 n is 0.
9. The aptamer of claim 1, wherein at least one X$^1$ is W.
10. The aptamer of claim 1, wherein at least one X$^2$ is C.
11. The aptamer of claim 1, wherein each W is independently, and for each occurrence, selected from:

5-(N-benzylcarboxyamide)-2'-deoxyuridine (BndU),
5-(N-benzylcarboxyamide)-2'-O-methyluridine,
5-(N-benzylcarboxyamide)-2'-fluorouridine,
5-(N-phenethylcarboxyamide)-2'-deoxyuridine (PEdU),
5-(N-thiophenylmethylcarboxyamide)-2'-deoxyuridine (ThdU),
5-(N-isobutylcarboxyamide)-2'-deoxyuridine (iBudU),
5-(N-tyrosylcarboxyamide)-2'-deoxyuridine (TyrdU),
5-(N-3,4-methylenedioxybenzylcarboxyamide)-2'-deoxyuridine (MBndU),
5-(N-4-fluorobenzylcarboxyamide)-2'-deoxyuridine (FBndU),
5-(N-3-phenylpropylcarboxyamide)-2'-deoxyuridine (PPdU),
5-(N-imidizolylethylcarboxyamide)-2'-deoxyuridine (ImdU),
5-(N-isobutylcarboxyamide)-2'-O-methyluridine,
5-(N-isobutylcarboxyamide)-2'-fluorouridine,
5-(N-tryptaminocarboxyamide)-2'-deoxyuridine (TrpdU),
5-(N-R-threoninylcarboxyamide)-2'-deoxyuridine (ThrdU),
5-(N-tryptaminocarboxyamide)-2'-O-methyluridine,
5-(N-tryptaminocarboxyamide)-2'-fluorouridine,
5-(N-[1-(3-trimethylamonium) propyl]carboxyamide)-2'-deoxyuridine chloride,
5-(N-naphthylmethylcarboxyamide)-2'-deoxyuridine (NapdU),
5-(N-naphthylmethylcarboxyamide)-2'-O-methyluridine,
5-(N-naphthylmethylcarboxyamide)-2'-fluorouridine,
5-(N-[1-(2,3-dihydroxypropyl)]carboxyamide)-2'-deoxyuridine),
5-(N-2-naphthylmethylcarboxyamide)-2'-deoxyuridine (2NapdU),
5-(N-2-naphthylmethylcarboxyamide)-2'-O-methyluridine,
5-(N-2-naphthylmethylcarboxyamide)-2'-fluorouridine,
5-(N-1-naphthylethylcarboxyamide)-2'-deoxyuridine (NEdU),
5-(N-1-naphthylethylcarboxyamide)-2'-O-methyluridine,
5-(N-1-naphthylethylcarboxyamide)-2'-fluorouridine,
5-(N-2-naphthylethylcarboxyamide)-2'-deoxyuridine (2NEdU),
5-(N-2-naphthylethylcarboxyamide)-2'-O-methyluridine,
5-(N-2-naphthylethylcarboxyamide)-2'-fluorouridine, 5-(N-3-benzofuranylethylcarboxyamide)-2'-deoxyuridine (BF dU),
5-(N-3-benzofuranylethylcarboxyamide)-2'-O-methyluridine,
5-(N-3-benzofuranylethylcarboxyamide)-2'-fluorouridine,
5-(N-3-benzothiophenylethylcarboxyamide)-2'-deoxyuridine (BTdU),
5-(N-3-benzothiophenylethylcarboxyamide)-2'-O-methyluridine, and
5-(N-3-benzothiophenylethylcarboxyamide)-2'-fluorouridine.

12. The aptamer of claim 1, wherein at least 1, at least 2, at least 3, at least 4, at least 5, or at least 6 W are each independently selected from 5-(N-tryptaminocarboxyamide)-2'-deoxyuridine (TrpdU), 5-(N-tryptaminocarboxyamide)-2'-O-methyluridine, and 5-(N-tryptaminocarboxyamide)-2'-fluorouridine.

13. The aptamer of claim 12, wherein each W is independently selected from 5-(N-tryptaminocarboxyamide)-2'-deoxyuridine (TrpdU), 5-(N-tryptaminocarboxyamide)-2'-O-methyluridine, and 5-(N-tryptaminocarboxyamide)-2'-fluorouridine.

14. The aptamer of claim 1, wherein the aptamer consists of 18 to 200 nucleotides, wherein each nucleotide may, independently, be a modified or unmodified nucleotide.

15. The aptamer of claim 1, wherein the aptamer comprises a detectable label.

16. The aptamer of claim 2, wherein GDF8 is mature human GDF8 comprising the sequence of SEQ ID NO: 63 and GDF11 is mature human GDF11 comprising the sequence of SEQ ID NO: 50.

17. A method of detecting GDF8 in a sample, comprising contacting proteins from the sample with an aptamer of claim 1.

18. An aptamer that binds GDF 8, wherein the aptamer comprises a sequence selected from SEQ ID NOs: 5 to 48.

19. The aptamer of claim 1, wherein each $R^1$ is A.

20. The aptamer of claim 1, wherein each $R^2$ is G.

21. The aptamer of claim 1, wherein each n is 0.

22. The aptamer of claim 1, wherein each $X^1$ is W.

23. The aptamer of claim 1, wherein each $X^2$ is C.

* * * * *